United States Patent
Frederich et al.

(10) Patent No.: US 12,221,419 B2
(45) Date of Patent: Feb. 11, 2025

(54) ABIETANES AND METHODS OF MAKING AND USING THE SAME

(71) Applicant: Florida State University Research Foundation, Incorporated., Tallahassee, FL (US)

(72) Inventors: James H. Frederich, Tallahassee, FL (US); Megan M. Solans, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 46 days.

(21) Appl. No.: 18/192,703

(22) Filed: Mar. 30, 2023

(65) Prior Publication Data

US 2024/0140912 A1 May 2, 2024

Related U.S. Application Data

(60) Provisional application No. 63/362,160, filed on Mar. 30, 2022.

(51) Int. Cl.
| | |
|---|---|
| C07C 13/68 | (2006.01) |
| C07C 22/08 | (2006.01) |
| C07C 25/22 | (2006.01) |
| C07C 35/44 | (2006.01) |
| C07C 43/215 | (2006.01) |
| C07C 49/753 | (2006.01) |
| C07C 49/755 | (2006.01) |
| C07D 215/06 | (2006.01) |
| C07D 215/227 | (2006.01) |
| C07D 307/79 | (2006.01) |

(52) U.S. Cl.
CPC .......... *C07D 215/227* (2013.01); *C07C 13/68* (2013.01); *C07C 22/08* (2013.01); *C07C 25/22* (2013.01); *C07C 35/44* (2013.01); *C07C 43/215* (2013.01); *C07C 49/753* (2013.01); *C07C 49/755* (2013.01); *C07D 215/06* (2013.01); *C07D 307/79* (2013.01); *C07C 2603/40* (2017.05)

(58) Field of Classification Search
CPC .............. C07D 215/227; C07D 215/06; C07D 307/79; C07C 13/68; C07C 22/08; C07C 25/22; C07C 35/44; C07C 43/215; C07C 49/753; C07C 49/755; C07C 2603/40
See application file for complete search history.

(56) References Cited

U.S. PATENT DOCUMENTS

| | | | |
|---|---|---|---|
| 3,976,684 A | * | 8/1976 | Barcza .................. C07C 59/90 514/569 |
| 2018/0353457 A1 | | 12/2018 | Jabbarzadeh et al. |

OTHER PUBLICATIONS

González MA. Aromatic abietane diterpenoids: their biological activity and synthesis. Nat Prod Rep. May 2015;32(5):684-704. doi: 10.1039/c4np00110a. PMID: 25643290. (Year: 2015).*
Valenzuela L, Vila R, Cañigueral S, Adzet T. The Essential Oil of Sphacele chamaedryoides. Planta Med. Jun. 1992;58(3):273-4. doi: 10.1055/s-2006-961452. PMID: 17226468. (Year: 1992).*
Parham, William E. and Leonard J. Czuba. "Evidence for the geometric requirements of phenyl migration." Journal of the American Chemical Society 90 (1968): 4030-4038. (Year: 1968).*
Zhou Q, Xie H, Zhang L, Stewart JK, Gu XX, Ryan JJ. cis-Terpenones as an effective chemopreventive agent against aflatoxin B1-induced cytotoxicity and TCDD-induced P450 1A/B activity in HepG2 cells. Chem Res Toxicol. Nov. 2006;19(11):1415-9. doi: 10.1021/tx0601307. PMID: 17112227; PMCID: PMC2527748. (Year: 2006).*
Gülaçti Topcu and Ayhan Ulubelen Abietane and Rearranged Abietane Diterpenes from Salvia montbretii Journal of Natural Products 1996 59 (8), 734-737 DOI: 10.1021/np9602224 (Year: 1996).*
Schmid, J.M., Uchida, M., Ruedi, P. and Eugster, C.H. (1982), Partialsynthesen und Reaktionen von Abietanderivaten (Lanugonen) aus Plectranthus lanuginosus und verwandten Verbindungen. HCA, 65: 2164-2180. https://doi.org/10.1002/hlca.19820650722 (Year: 1982).*
Miguel A. Zuniga, Jifeng Dai, Mark P. Wehunt, and Qibing Zhou DNA Oxidative Damage by Terpene Catechols as Analogues of Natural Terpene Quinone Methide Precursors in the Presence of Cu(II) and/or NADH Chemical Research in Toxicology 2006 19 (6), 828-836 (Year: 2006).*
Areche C, Schmeda-Hirschmann G, Theoduloz C, Rodríguez JA. Gastroprotective effect and cytotoxicity of abietane diterpenes from the Chilean Lamiaceae *Sphacele chamaedryoides* (Balbis) Briq. J Pharm Pharmacol. Dec. 2009;61(12):1689-97. doi: 10.1211/jpp/61. 12.0015. PMID: 19958593. (Year: 2009).*
Kuźma L, Wysokińska H, Różalski M, Budzyńska A, Więckowska-Szakiel M, Sadowska B, Paszkiewicz M, Kisiel W, Różalska B. Antimicrobial and anti-biofilm properties of new taxodione derivative from hairy roots of Salvia austriaca. Phytomedicine. Nov. 15, 2012;19(14):1285-7. doi: 10.1016 (Year: 2012).*
National Center for Biotechnology Information: 5,6,7,8,8a, 10-hexahydro-4bH-phenanthren-9-one: Pubchem CID 318258 p. 1-13 Mar. 26, 2005.

(Continued)

*Primary Examiner* — Matthew P Coughlin
*Assistant Examiner* — Anna Grace Kuckla
(74) *Attorney, Agent, or Firm* — Thomas | Horstemeyer, LLP

(57) ABSTRACT

In accordance with the purpose(s) of the present disclosure, as embodied and broadly described herein is versatile polyene cyclization strategy that exploits conjugated β-ionyl derivatives. Photomediated disruption of the extended π-system within these chromophores unveils a contra-thermodynamic polyene that engages in a Heck-type cyclization to afford [4.4.1]-propellanes. The connectivity of overbred polycycles generated from this process is controlled by the position of the requisite C-Halide bond. Thus, compared to conventional biomimetic polyene cyclization, this approach allows for complete control of regiochemistry and facilitates incorporation of both electron-rich and electron-deficient (hetero)aryl groups. This strategy was successfully applied to the total synthesis of abietanes such as, for example, taxodione and salviasperanol, two isomeric abietane-type diterpenes that previously could not be prepared along the same synthetic pathway.

30 Claims, 6 Drawing Sheets

(56) References Cited

OTHER PUBLICATIONS

Sitarek, P et al., Insight the Biological Activities of Selected Abietane Diterpenes Isolated from *Plectranthus* spp., Biomolecules 10,.194, pp. 1-13, 2020; Retrieved on Jul. 12, 2023 from the Internet: [URL: https://www.ncbi.nlm.nih.gov/pmc/articles/PMC7072155/]; abstract; p. 2, figure 1; p. 3, first paragraph; p. 11, second paragraph.

National Center for Biotechnology Information: 9-Fluorobenzo[h]isoquinoline-5,6-dione:Pubchem CID 90921330n Pubchem entry (online), pp. 1-10, Mar. 17, 2015.

National Center for Biotechnology Information: Benzo[f]quinoline-5,6-dione: Pubchem CID 12394151 Pubchem entry (online), pp. 1-15, Feb. 8, 2007.

National Center for Biotechnology Information: (5aS, 9aS)-6,6,9a-Trimethyl-4,5,5a,6, 7,8,9,9a-octahydronaphtho[2, 1-b] furan: Pubchem CID 11401707 Pubchem entry (online),pp. 1-11, Oct. 26, 2006.

National Center for Biotechnology Information: 3,6-Dimethylnaphtho[1,2-b]furan-4,5-dione:Pubchem CID 607838 Pubchem entry (online), pp. 1-13, Mar. 27, 2005.

National Center for Biotechnology Information: 9beta, 9abeta-Dimethyl-4,5,5abeta,6,7,8,9,9a-octahydronaphtho[1,2-b] furan-4-one: Pubchem CID 100974655 Pubchem entry (online), pp. 1-11, Dec. 15, 2015.

National Center for Biotechnology Information: Phenanthrene-3,9-dione: Pubchem CID 21311035 Pubchem entry (online), pp. 1-11, Dec. 5, 2007.

National Center for Biotechnology Information: (4aR)-8-but-3-enyl-4a, 7, 7-trimethyl-10-methylidene-4b,5,6,8,8a,9-hexahydrophenanthren-2-on e: Pubchem CID 89177351 Pubchem entry (online), pp. 1-11, Feb. 13, 2015.

National Center for Biotechnology Information: 9-methyl-3H-phenanthren-2-one: Pubchem CID 154213178 Pubchem entry (online), pp. 1-11, Aug. 14, 2020.

National Center for Biotechnology Information: Tricyclo[4.4.1. 0(1,6)]undecane: Pubchem CID 585259 Pubchem entry (online), pp. 1-12, Mar. 27, 2005.

National Center for Biotechnology Information: 4, 17, 17-Trimethyl-18-methylidene pentacyclo{12.4.1.01, 14.02,11.05,10]nonadeca-2(11), 3,5,7,9-pentaene-12,13-dione: Pubchem CID 143993728 Pubchem entry (online), pp. 1-10, Dec. 7, 2019.

National Center for Biotechnology Information: 3-Methylidene-8-azatetracyclo[9.3.2.01,10.04, 9]hexadeca-4(9),5,7-triene: Pubchem CID 126542580 Pubchem entry (ontine), pp. 1-10, Apr. 22, 2017.

International Search Report for PCT/US/2023/065122 dated Nov. 8, 2023.

\* cited by examiner

ABIETANES AND METHODS OF MAKING AND USING THE SAME

CROSS-REFERENCE TO RELATED APPLICATIONS

This application claims the benefit of and priority to U.S. Provisional Patent Application No. 63/362,160, filed on Mar. 30, 2022, the contents of which are incorporated by reference herein in their entireties.

STATEMENT REGARDING FEDERALLY SPONSORED RESEARCH OR DEVELOPMENT

This invention was made with government support under grant number R01 GM125926, awarded by the National Institutes of Health. The government has certain rights in the invention.

BACKGROUND

Diterpenes are a rich source of biologically active molecular scaffolds.[1,2] Members of this family harboring a fused [6-6-6] carbocyclic nucleus have gained significant attention for their valuable pharmacological profiles.[3-5] This subgroup of natural products includes abietane, pimarane, and kaurane diterpenes, which all share copalyl diphosphate as a common biosynthetic progenitor (FIG. 1).[6] Although the skeletal diversity of these diterpenes is localized within the C-ring, each motif is further differentiated through late-stage oxidative tailoring.[7] This added layer of complexity hinders the design of unified synthetic entry to this diverse collection of targets. Recent advances in synthetic biology have streamlined entry to this subgroup from more accessible terpenoid starting points.[8] In contrast, polyene cyclization provides a generalized platform for de novo diterpene synthesis. This bioinspired strategy seeks to reorganize isolated polyenes (1) to polycycles (2) through a series of concerted C—C bond formations.[9] Both cationic and radical reaction modalities are known, as are enantioselective adaptations catalyzed by Lewis acids,[10] organocatalysts,[11] and transition metals.[12] The outcomes of polyene cyclization are predictable and governed by explicit aspects of alkene stereochemistry and electronics.[9a] This powerful feature is often exploited in total synthesis;[9c] however, it also makes it difficult to extend this strategy to diversified substrates (e.g. 1a-1c) that deviate from biogenic isoprenoid precursors.[13,14]

SUMMARY

In accordance with the purpose(s) of the present disclosure, as embodied and broadly described herein is versatile polyene cyclization strategy that exploits conjugated β-ionyl derivatives. Photomediated disruption of the extended π-system within these chromophores unveils a contra-thermodynamic polyene that engages in a Heck-type cyclization to afford [4.4.1]-propellanes. The connectivity of overbred polycycles generated from this process is controlled by the position of the requisite C-Halide bond. Thus, compared to conventional biomimetic polyene cyclization, this approach allows for complete control of regiochemistry and facilitates incorporation of both electron-rich and electron-deficient (hetero)aryl groups. This strategy was successfully applied to the total synthesis of abietanes such as, for example, taxodione and salviasperanol, two isomeric abietane-type diterpenes that previously could not be prepared along the same synthetic pathway.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1:
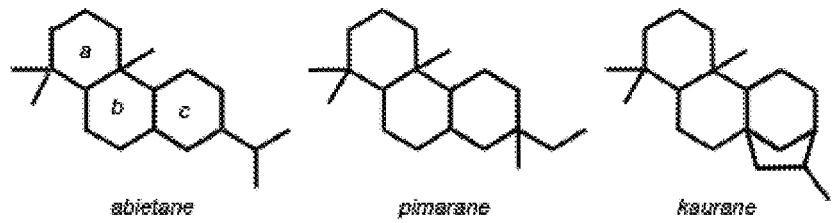
FIG. 1 shows a polyene cyclization strategy enabled by photoinduced disruption of the extended π-system to produce a [4.4.41]-propellane.
Figure 1:
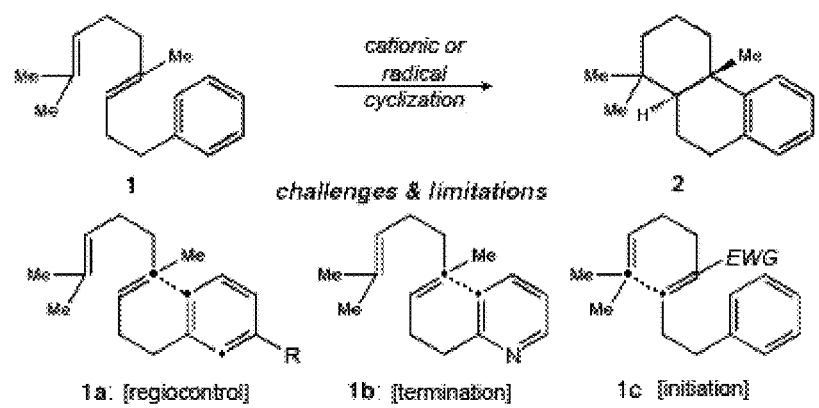
Figure 1:
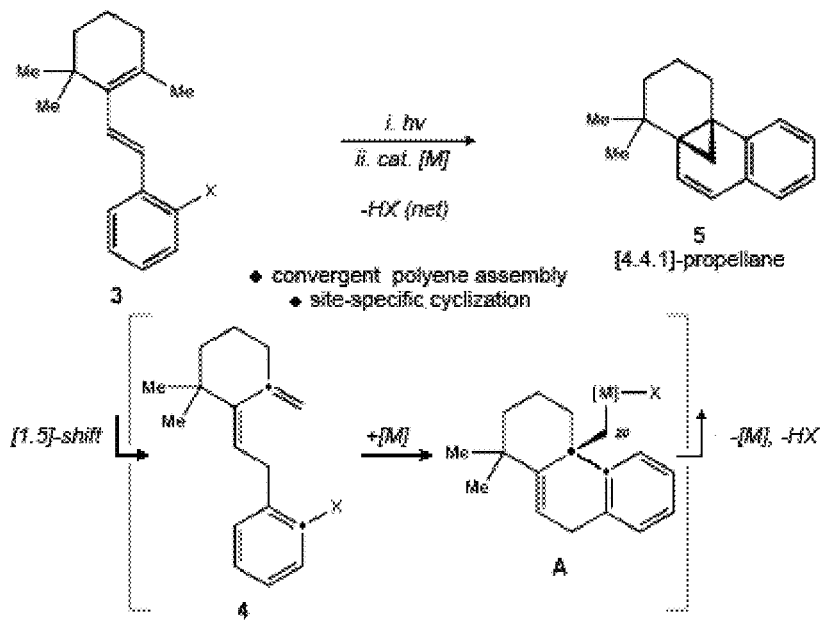

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "an excipient" include, but are not limited to, mixtures or combinations of two or more such excipients, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "IC$_{50}$," is intended to refer to the concentration of a substance (e.g., a compound or a drug) that is required for 50% inhibition of a biological process, or component of a process. For example, IC$_{50}$ refers to the half maximal (50%) inhibitory concentration (IC) of a substance as determined in a suitable assay. For example, an IC$_{50}$ for an abietane described herein can be determined in an in vitro or cell-based assay system. Frequently, receptor assays make use of a suitable cell-line, e.g. a cell line that either expresses endogenously a target of interest, or has been transfected with a suitable expression vector that directs expression of a recombinant form of the target. For example, the IC$_{50}$ for a compound disclosed herein can be determined using cancer cells contacted with a compound described herein.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The position of a substituent can be defined relative to the positions of other substituents in an aromatic ring. For example, as shown below in relationship to the "R" group, a second substituent can be "ortho," "para," or "meta" to the R group, meaning that the second substituent is bonded to a carbon labeled ortho, para, or meta as indicated below. Combinations of ortho, para, and meta substituents relative to a given group or substituent are also envisioned and should be considered to be disclosed.

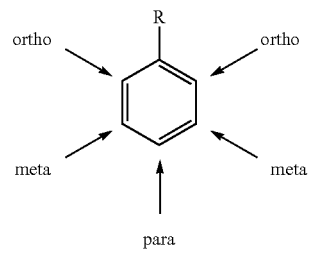

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, carboxylic acid, ester, nitro, silyl, sulfo-oxo, orthiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, and —$CH_2CH_2CH_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl. Fused aryl groups including, but not limited to, indene and naphthalene groups are also contemplated.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," ... "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

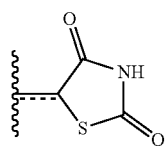

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thiohaloal-kyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}$H, $^{3}$H, $^{13}$C, $^{14}$C, $^{15}$N, $^{18}$O, $^{17}$O, $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

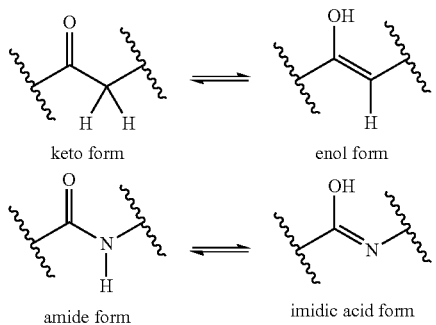

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

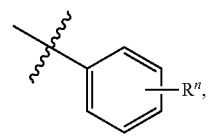

which is understood to be equivalent to a formula:

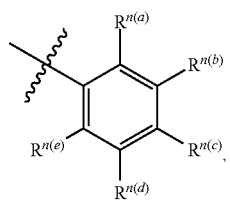

wherein n is typically an integer. That is, R″ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

As used herein, the terms "optional" or "optionally" means that the subsequently described event or circumstance can or cannot occur, and that the description includes instances where said event or circumstance occurs and instances where it does not.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a hematological malignancy, breast cancer, and/or another solid malignancy. The effect can be therapeutic in terms of a partial or complete cure of a disease, condition, symptom or adverse effect attributed to the disease, disorder, or condition. The term "treatment" as used herein can include any treatment of a hematological malignancy, breast cancer, and/or another solid tumor in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Unless otherwise specified, temperatures referred to herein are based on atmospheric pressure (i.e. one atmosphere).

Compounds and Methods of Making the Same

Described herein is an atypical polyene cyclization strategy that converts easily accessible β-ionyl derivatives into polycyclic [4.4.1]-propellanes. Unlike canonical biomimetic polyene cyclization, this strategy allows for complete control of regiochemistry and tolerates a range of electron-rich and electron-deficient (hetero)aryl groups. The polycyclic [4.4.1]-propellanes produced by the methods described herein can be used to generate a wide variety of non-canonical abeo-abietane scaffolds that would be difficult or impossible to prepare using conventional biomimetic logic.

In one aspect, the polycyclic [4.4.1]-propellanes are produced by the method comprising (a) exposing the compound having the structure XXI to light to produce a first intermediate

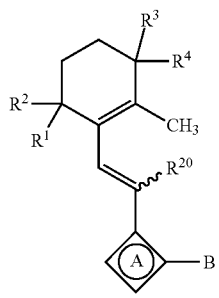

XXI wherein $R^1$-$R^4$ and $R^{20}$ are independently hydrogen, a halide, a substituted or unsubstituted alkyl group, an alkoxy group, or a hydroxy group, and A is a substituted or unsubstituted aryl group or a substituted or unsubstituted heteroaryl group;

B is a halide; and (b) reacting the first intermediate with a transition metal catalyst to produce the [4.4.1]-propellane.

In one aspect, the compound having the structure IX is dissolved in an organic solvent (e.g., THF, dioxane, MeCN) then exposed to light having a wavelength of about 250 nm to about 350 nm, about 275 nm to about 325 nm, or about 300 nm. The compound having the structure IX can be exposed to light from 1 hour to 10 hours, 2 hours to 8 hours, 4 hours to 6 hours, or about 5 hours.

The first intermediate produced after exposing the compound having the structure IX to light is subsequently reacted with a transition metal catalysts that will perform a Heck reaction. In one aspect, the transition metal catalyst comprises a palladium(II) catalyst. In another aspect, the transition metal catalyst is $Pd_2dba_3$ and $(t\text{-}Bu)_3P\cdot HBF_4$, where the molar ratio is from 1:2 to 2:1, or 1:1. Non-limiting methods for producing the [4.4.1]-propellane using the methods described herein are provided in the Examples.

In one aspect, A in structure IX has the structure XXII

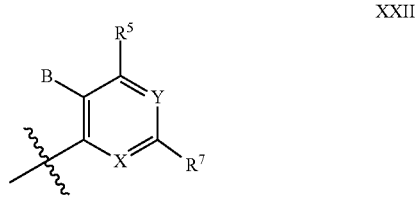

XXII wherein X is $CR^3$ or N;

Y is $CR^6$ or N; and $R^5$-$R^8$ are independently hydrogen, an alkyl group, an alkoxy group, or a hydroxy group.

In one aspect, wherein X is $CR^8$ and Y is $CR^6$. In another aspect, B in structures IX and X is bromide or iodide.

In one aspect, the [4.4.1]-propellane has the structure XVIII

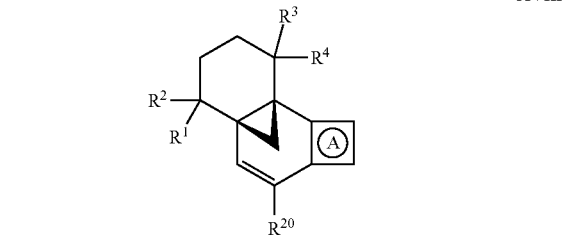

XVIII wherein $R^1$-$R^4$ and $R^{20}$ are independently hydrogen, a halide, a substituted or unsubstituted alkyl group, an alkoxy group, r a hydroxy group, and A is a substituted or unsubstituted aryl group or a substituted or unsubstituted heteroaryl group.

In one aspect, the [4.4.1]-propellane has the structure XIX

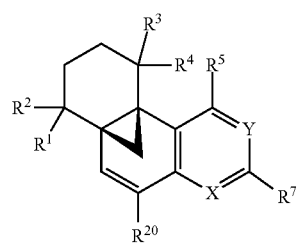

XIX wherein X is $CR^8$ or N;

Y is $CR^6$ or N; and $R^5$-$R^3$ are independently hydrogen, an alkyl group, an alkoxy group, or a hydroxy group.

In one aspect, X is $CR^8$ and Y is $CR^6$ in structure XVIII and XIX. In another aspect, $R^6$ and $CR^8$ in structure VI and VII are an alkoxy group.

In one aspect, the [4.4.1]-propellane has the structure XX

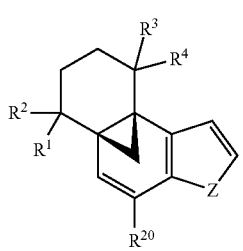

XX wherein Z is O, S, $CR^{11}$, or $NR^{12}$, and
$R^{11}$ and $R^{12}$ are hydrogen, an alkyl group, or an aryl group.

In one aspect, $R^1$ and $R^2$ in structure VIII are each an alkyl group. In one aspect, $R^1$ and $R^2$ in structure VIII are each a methyl group. In another aspect, $R^3$ and $R^4$ in structure VIII are each hydrogen.

The [4.4.1]-propellanes produced by the methods described herein can produce compounds that are precursors to biologically active compounds.

In one aspect, the [4.4.1]-propellanes produced herein can be used to synthesize compounds having the structure XXII

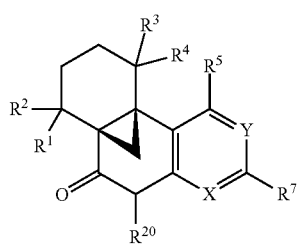

XXIII wherein X is $CR^3$ or N;
Y is $CR^6$ or N; and
$R^1$-$R^8$ and $R^{20}$ are independently hydrogen, a substituted or unsubstituted alkyl group, an alkoxy group, or a hydroxy group.

In one aspect, the [4.4.1]-propellanes produced herein can be used to synthesize compounds having the structure X or the pharmaceutically acceptable salt or ester thereof

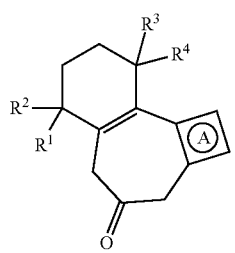

X wherein $R^1$-$R^4$ are independently hydrogen, a halide, a substituted or unsubstituted alkyl group, an alkoxy group, or a hydroxy group, and
A is a substituted or unsubstituted aryl group or a substituted or unsubstituted heteroaryl group.

In one aspect, the [4.4.1]-propellanes produced herein can be used to synthesize compounds having the structure XI or XII or the pharmaceutically acceptable salt or ester thereof

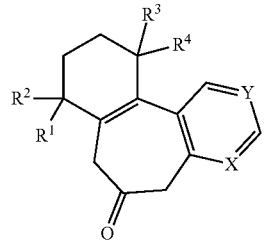

XI

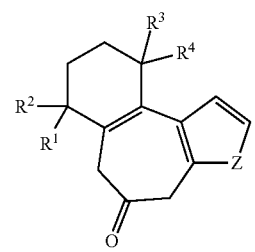

XII wherein X is N or $CR^9$,
Y is N or $CR^{10}$, and
Z is O, S, $CR^{11}$, or $NR^{12}$,
wherein $R^9$-$R^{12}$ are hydrogen, an alkyl group, or an aryl group.

In one aspect, the [4.4.1]-propellanes produced herein can be used to synthesize compounds having the structure XIII or the pharmaceutically acceptable salt or ester thereof

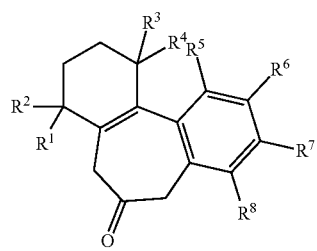

XIII wherein $R^1$-$R^8$ are independently hydrogen, a halide, an alkyl group, an alkoxy group, or
a hydroxy group.

In one aspect, the [4.4.1]-propellanes produced herein can be used to synthesize compounds having the structure V or the pharmaceutically acceptable salt or ester thereof

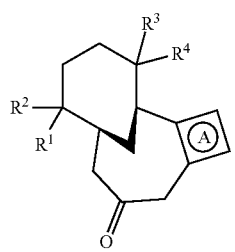

V wherein R¹-R⁴ are independently hydrogen, a halide, a substituted or unsubstituted alkyl group, an alkoxy group, or a hydroxy group, and A is a substituted or unsubstituted aryl group or a substituted or unsubstituted heteroaryl group.

In one aspect, the [4.4.1]-propellanes produced herein can be used to synthesize compounds having the structure VI or VII or the pharmaceutically acceptable salt or ester thereof

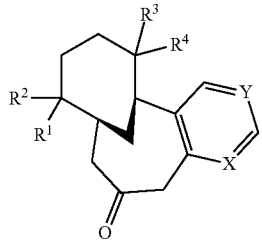

VI

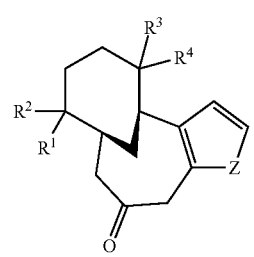

VII wherein X is N or CR⁹,
Y is N or CR¹⁰, and
Z is O, S, CR¹¹, or NR¹²,
wherein R⁹-R¹² are hydrogen, an alkyl group, or an aryl group.

In one aspect, the [4.4.1]-propellanes produced herein can be used to synthesize compounds having the structure VIII or IX or the pharmaceutically acceptable salt or ester thereof

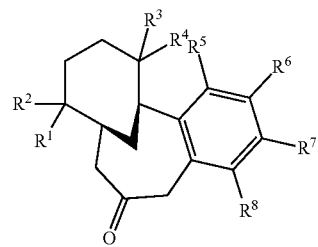

VIII

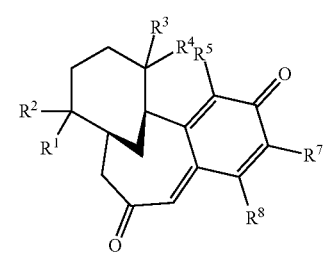

IX wherein R¹-R⁸ are independently hydrogen, a halide, an alkyl group, an alkoxy group, or a hydroxy group.

In one aspect, the [4.4.1]-propellanes produced herein can be used to synthesize compounds having the structure I or the pharmaceutically acceptable salt or ester thereof

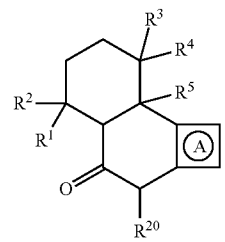

I wherein R¹-R⁵ and R²⁰ are independently hydrogen, a halide, a substituted or unsubstituted alkyl group, an alkoxy group, or a hydroxy group, A is a substituted or unsubstituted aryl group or a substituted or unsubstituted heteroaryl group, and wherein the compound is not taxodione.

In one aspect, the [4.4.1]-propellanes produced herein can be used to synthesize compounds having the structure II or III or the pharmaceutically acceptable salt or ester thereof

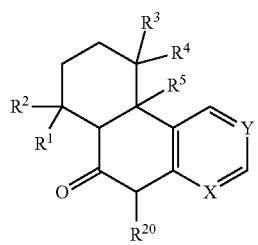

II

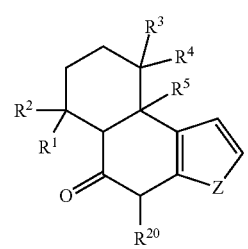

III wherein X is N or CR⁹,
Y is N or CR¹⁰, and
Z is O, S, CR¹¹, or NR¹²,
wherein R⁹-R¹² are hydrogen, an alkyl group, or an aryl group.

In one aspect, the [4.4.1]-propellanes produced herein can be used to synthesize compounds having the structure IV or the pharmaceutically acceptable salt or ester thereof

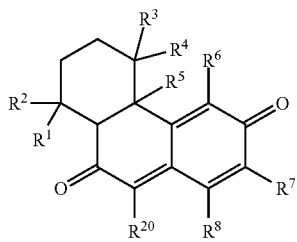

IV wherein $R^1$-$R^8$ are independently hydrogen, a halide, a substituted or unsubstituted alkyl group, an alkoxy group, or a hydroxy group.

In one aspect, the compound is

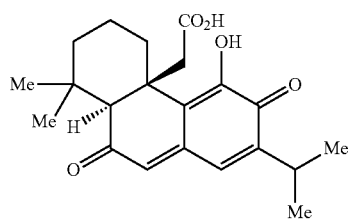

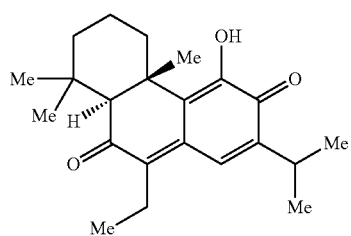

In one aspect, the [4.4.1]-propellanes produced herein can be used to synthesize compounds having the structure XIV or the pharmaceutically acceptable salt or ester thereof

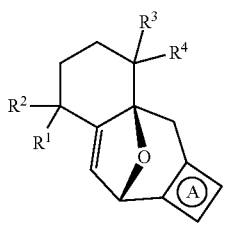

XIV wherein $R^1$-$R^4$ are independently hydrogen, a halide, a substituted or unsubstituted alkyl group, an alkoxy group, or a hydroxy group, A is a substituted or unsubstituted aryl group or a substituted or unsubstituted heteroaryl group, and wherein the compound is not salviasperanol.

In one aspect, the [4.4.1]-propellanes produced herein can be used to synthesize compounds having the structure XV or XVI or the pharmaceutically acceptable salt or ester thereof

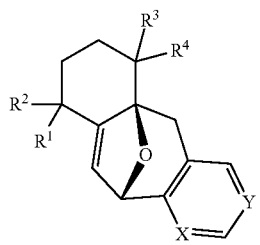

XV

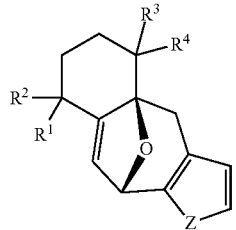

XVI wherein X is N or $CR^9$,
Y is N or $CR^{10}$, and
Z is O, S, $CR^{11}$, or $NR^{12}$,
wherein $R^9$-$R^{12}$ are hydrogen, an alkyl group, or an aryl group.

In one aspect, the [4.4.1]-propellanes produced herein can be used to synthesize compounds having the structure XVII or the pharmaceutically acceptable salt or ester thereof

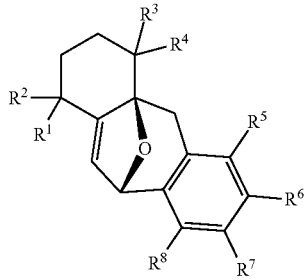

XVII wherein $R^1$-$R^8$ are independently hydrogen, a halide, an alkyl group, an alkoxy group, or
a hydroxy group.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Therapeutic Applications
Methods for Treatment of Cancers in Subjects

In one aspect, disclosed herein is a method for the treatment of a cancer in a subject, the method including the step of administering to the subject a therapeutically effective amount of at least one disclosed compound, or a pharmaceutically acceptable salt thereof, or the disclosed pharmaceutical composition. In some aspects, the subject is a human. In another aspect, the subject has been diagnosed with a need for treatment of the cancer prior to the administering step. In some aspects, the method further includes the step of identifying a subject in need of treatment of the cancer. In one aspect, the cancer is selected from multiple myeloma, lymphoma, mantle cell lymphoma, acute leukemia, cancers associated with human papillomavirus, colorectal cancer, gastric cancer, ovarian cancer, liver cancer, breast cancer, cervical cancer, pancreatic cancer, prostate cancer, brain cancer, or any combination thereof. In another aspect, the compounds described herein can inhibit the growth of glioblastoma cells in a subject.

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitoneally, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{13}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxy-ethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, Iinolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In one aspect, an appropriate dosage level will generally be about 0.01 to 1000 mg of a compound described herein per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

Kits

In a further aspect, the present disclosure relates to kits comprising (a) at least one disclosed compound, or a pharmaceutically acceptable salt, hydrate, solvate, or polymorph thereof and one of (b) instructions for treating a cancer or (c) instructions for administering the compound in connection with another cancer therapy.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered aspects, which should not be confused with the claims.

Aspect 1. A compound having the structure I or the pharmaceutically acceptable salt or ester thereof

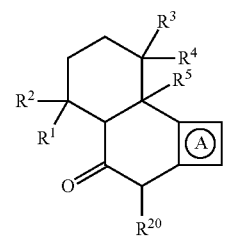

wherein $R^1$-$R^5$ and $R^{20}$ are independently hydrogen, a halide, a substituted or unsubstituted alkyl group, an alkoxy group, or a hydroxy group, A is a substituted or unsubstituted aryl group or a substituted or unsubstituted heteroaryl group, and wherein the compound is not taxodione.

Aspect 2. The compound of Aspect 1, wherein the compound has the structure II or III or the pharmaceutically acceptable salt or ester thereof

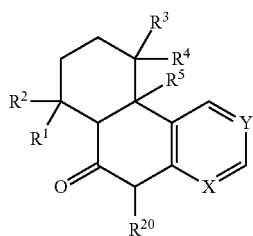

II

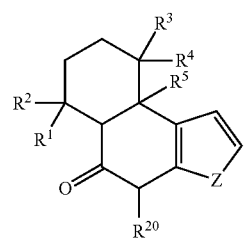

III wherein X is N or CR$^9$,
Y is N or CR$^{10}$, and
Z is O, S, CR$^{11}$, or NR$^{12}$,
wherein R$^9$-R$^{12}$ are hydrogen, an alkyl group, or an aryl group.

Aspect 3. The compound of Aspect 2, wherein X is CH and Y is N.

Aspect 4. The compound of Aspect 2, wherein X is N and Y is CH.

Aspect 5. The compound of Aspect 2, wherein Z is O.

Aspect 6. The compound of Aspect 1, wherein the compound has the structure IV or the pharmaceutically acceptable salt or ester thereof

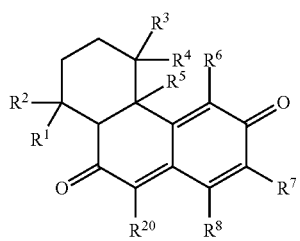

IV wherein R$^1$-R$^8$ are independently hydrogen, a halide, a substituted or unsubstituted alkyl group, an alkoxy group, or a hydroxy group.

Aspect 7. The compound of Aspect 6, wherein R$^1$ and R$^2$ are each an alkyl group.

Aspect 8. The compound of Aspect 7, wherein R$^1$ and R$^2$ are each a methyl group.

Aspect 9. The compound of anyone of Aspects 6-8, wherein R$^3$ and R$^4$ are each hydrogen.

Aspect 10. The compound of anyone of Aspects 6-9, wherein R$^5$ is an alkyl group.

Aspect 11. The compound of anyone of Aspects 6-9, wherein R$^5$ is a methyl group.

Aspect 12. The compound of anyone of Aspects 6-11, wherein R$^6$ is an alkoxy group.

Aspect 13. The compound of anyone of Aspects 6-11, wherein R$^6$ is a methoxy group.

Aspect 14. The compound of anyone of Aspects 6-11, wherein R$^6$ is a hydroxy group.

Aspect 15. The compound of anyone of Aspects 6-14, wherein R$^7$ is an alkyl group.

Aspect 16. The compound of anyone of Aspects 6-14, wherein R$^7$ is an isopropyl group.

Aspect 17. The compound of anyone of Aspects 6-16, wherein R$^8$ is hydrogen and R$^{20}$ is hydrogen or an unsubstituted alkyl group.

Aspect 18. A compound having the structure V or the pharmaceutically acceptable salt or ester thereof

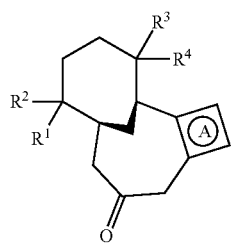

V wherein R$^1$-R$^4$ are independently hydrogen, a halide, a substituted or unsubstituted alkyl group, an alkoxy group, or a hydroxy group, and
A is a substituted or unsubstituted aryl group or a substituted or unsubstituted heteroaryl group.

Aspect 19. The compound of Aspect 18, wherein the compound has the structure VI or VII or the pharmaceutically acceptable salt or ester thereof

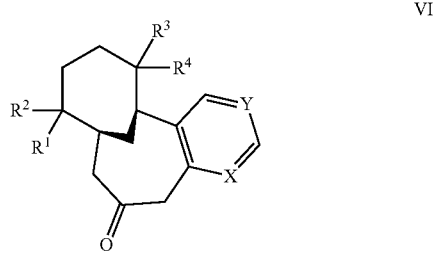

VI

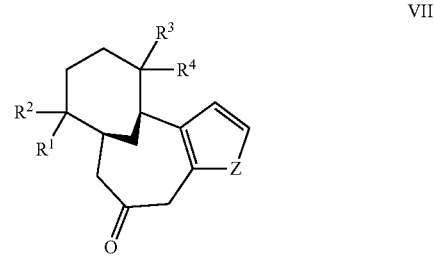

VII wherein X is N or CR$^9$,
Y is N or CR$^{10}$, and
Z is O, S, CR$^{11}$, or NR$^{12}$,
wherein R$^9$-R$^{12}$ are hydrogen, an alkyl group, or an aryl group.

Aspect 20. The compound of Aspect 19, wherein X is CH and Y is N.

Aspect 21. The compound of Aspect 19, wherein X is N and Y is CH.

Aspect 22. The compound of Aspect 19, wherein Z is O.

Aspect 23. The compound of Aspect 18, wherein the compound has the structure VIII or IX or the pharmaceutically acceptable salt or ester thereof

VIII

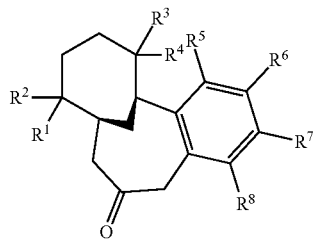

IX

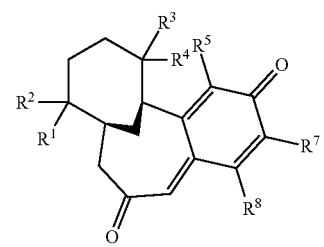

XI

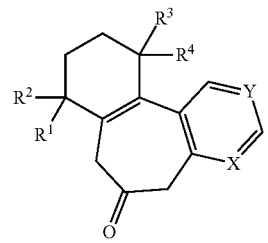

XII

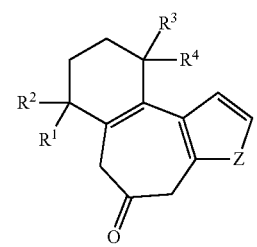

wherein $R^1$-$R^8$ are independently hydrogen, a halide, an alkyl group, an alkoxy group, or a hydroxy group.

Aspect 24. The compound of Aspect 23, wherein $R^1$ and $R^2$ are each an alkyl group.

Aspect 25. The compound of Aspect 23, wherein $R^1$ and $R^2$ are each a methyl group.

Aspect 26. The compound of anyone of Aspects 23-25, wherein $R^3$ and $R^4$ are each hydrogen.

Aspect 27. The compound of anyone of Aspects 23-26, wherein $R^5$ and $R^6$ are each an alkoxy group.

Aspect 28. The compound of Aspect 27, wherein $R^5$ and $R^6$ are each a methoxy group.

Aspect 29. The compound of anyone of Aspects 23-28, wherein $R^5$ is a hydroxy group.

Aspect 30. The compound of anyone of Aspects 23-29, wherein $R^7$ is an alkyl group.

Aspect 31. The compound of Aspect 30, wherein $R^7$ is an isopropyl group.

Aspect 32. The compound of anyone of Aspects 23-31, wherein $R^8$ is hydrogen.

Aspect 33. A compound having the structure X or the pharmaceutically acceptable salt or ester thereof

X

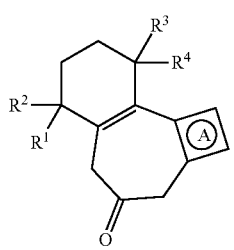

wherein $R^1$-$R^4$ are independently hydrogen, a halide, a substituted or unsubstituted alkyl group, an alkoxy group, or a hydroxy group, and A is a substituted or unsubstituted aryl group or a substituted or unsubstituted heteroaryl group.

Aspect 34. The compound of Aspect 33, wherein the compound has the structure XI or XII or the pharmaceutically acceptable salt or ester thereof wherein X is N or $CR^9$,
Y is N or $CR^{10}$, and
Z is O, S, $CR^{11}$, or $NR^{12}$,
wherein $R^9$-$R^{12}$ are hydrogen, an alkyl group, or an aryl group.

Aspect 35. The compound of Aspect 34, wherein X is CH and Y is N.

Aspect 36. The compound of Aspect 34, wherein X is N and Y is CH.

Aspect 37. The compound of Aspect 34, wherein Z is O.

Aspect 38. The compound of Aspect 33, wherein the compound has the structure XIII or the pharmaceutically acceptable salt or ester thereof

XIII

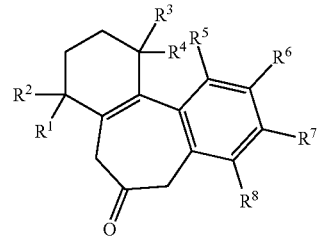

wherein $R^1$-$R^8$ are independently hydrogen, a halide, an alkyl group, an alkoxy group, or a hydroxy group.

Aspect 39. The compound of Aspect 38, wherein $R^1$ and $R^2$ are each an alkyl group.

Aspect 40. The compound of Aspect 38, wherein $R^1$ and $R^2$ are each a methyl group.

Aspect 41. The compound of anyone of Aspects 38-40, wherein $R^3$ and $R^4$ are each hydrogen.

Aspect 42. The compound of anyone of Aspects 38-41, wherein $R^5$ and $R^6$ are each an alkoxy group.

Aspect 43. The compound of Aspect 42, wherein $R^5$ and $R^6$ are each a methoxy group.

Aspect 44. The compound of anyone of Aspects 37-43, wherein $R^7$ is an alkyl group.

Aspect 45. The compound of Aspect 44, wherein $R^7$ is an isopropyl group.

Aspect 46. The compound of anyone of Aspects 37-45, wherein $R^8$ is hydrogen.

Aspect 47. A compound having the structure XIV or the pharmaceutically acceptable salt or ester thereof

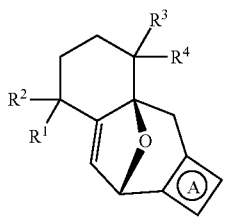

XIV wherein $R^1$-$R^4$ are independently hydrogen, a halide, a substituted or unsubstituted alkyl group, an alkoxy group, or a hydroxy group, A is a substituted or unsubstituted aryl group or a substituted or unsubstituted heteroaryl group, and wherein the compound is not salviasperanol.

Aspect 48. The compound of Aspect 47, wherein the compound has the structure XV or XVI or the pharmaceutically acceptable salt or ester thereof

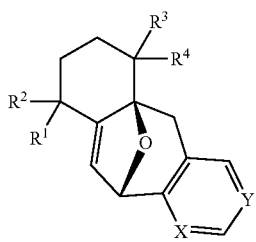

XV

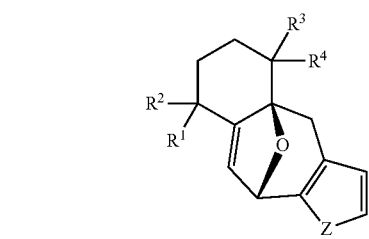

XVI wherein X is N or $CR^9$,

Y is N or $CR^{10}$, and

Z is O, S, $CR^{11}$, or $NR^{12}$, wherein $R^9$-$R^{12}$ are hydrogen, an alkyl group, or an aryl group.

Aspect 49. The compound of Aspect 48, wherein X is CH and Y is N.

Aspect 50. The compound of Aspect 48, wherein X is N and Y is CH.

Aspect 51. The compound of Aspect 48, wherein Z is O.

Aspect 52. The compound of Aspect 47, wherein the compound has the structure XVII or the pharmaceutically acceptable salt or ester thereof

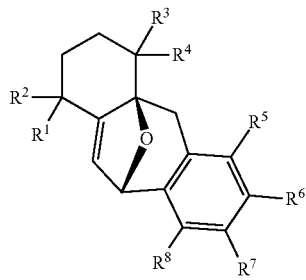

XVII wherein $R^1$-$R^8$ are independently hydrogen, a halide, an alkyl group, an alkoxy group, or a hydroxy group.

Aspect 53. The compound of Aspect 52, wherein $R^1$ and $R^2$ are each an alkyl group.

Aspect 54. The compound of Aspect 52, wherein $R^1$ and $R^2$ are each a methyl group.

Aspect 55. The compound of anyone of Aspects 52-54, wherein $R^3$ and $R^4$ are each hydrogen.

Aspect 56. The compound of anyone of Aspects 52-55, wherein $R^5$ and $R^6$ are each an alkoxy group.

Aspect 57. The compound of anyone of Aspects 52-55, wherein $R^5$ and $R^6$ are each a hydroxy group.

Aspect 58. The compound of anyone of Aspects 52-57, wherein $R^7$ is an alkyl group.

Aspect 59. The compound of anyone of Aspects 52-57, wherein $R^7$ is an isopropyl group.

Aspect 60. The compound of anyone of Aspects 52-59, wherein $R^8$ is hydrogen.

Aspect 61. A pharmaceutical composition comprising a compound in any one of Aspects 1-60.

Aspect 62. A method of treating cancer in a subject, the method comprising administering to the subject a compound in any one of Aspects 1-60.

Aspect 63. A method of inhibiting the growth of glioblastoma cells in a subject, the method comprising administering to the subject a compound in any one of Aspects 1-60.

Aspect 64. A compound having the structure XVIII

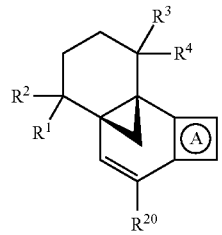

XVIII wherein $R^1$-$R^4$ and $R^{20}$ are independently hydrogen, a halide, a substituted or unsubstituted alkyl group, an alkoxy group, r a hydroxy group, and A is a substituted or unsubstituted aryl group or a substituted or unsubstituted heteroaryl group.

Aspect 65. The compound of Aspect 64, wherein the compound has the structure XIX

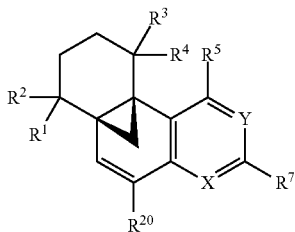

XIX wherein X is CR³ or N;
Y is CR⁶ or N; and
R⁵-R³ are independently hydrogen, an alkyl group, an alkoxy group, or a hydroxy group.

Aspect 66. The compound of Aspect 65, wherein X is CR³ and Y is CR⁶.

Aspect 67. The compound of Aspect 65 or 66, wherein R⁶ and CR³ are an alkoxy group.

Aspect 68. The compound of Aspect 64, wherein the compound has the structure XX

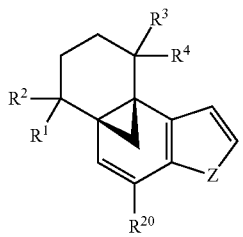

XX wherein Z is O, S, CR¹¹, or NR¹², and
R¹¹ and R¹² are hydrogen, an alkyl group, or an aryl group.

Aspect 69. The compound of anyone of Aspects 64-68, wherein R¹ and R² are each an alkyl group.

Aspect 70. The compound of anyone of Aspects 64-68, wherein R¹ and R² are each a methyl group.

Aspect 71. The compound of anyone of Aspects 64-70, wherein R³ and R⁴ are each hydrogen.

Aspect 72. A method for making the compound in any one of Aspects 64-71, the method comprising
(a) exposing the compound having the structure XXI to light to produce a first intermediate

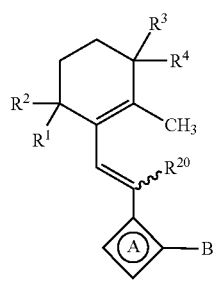

XXI wherein R¹-R⁴ and R²⁰ are independently hydrogen, a halide, a substituted or unsubstituted alkyl group, an alkoxy group, or a hydroxy group, and A is a substituted or unsubstituted aryl group or a substituted or unsubstituted heteroaryl group;
B is a halide; and
(b) reacting the first intermediate with a transition metal catalyst to produce the compound in any one of Aspects 64-71.

Aspect 73. The method of Aspect 72, wherein the light has a wavelength of about 250 nm to about 350 nm, preferably about 275 nm to about 325 nm, or about 300 nm.

Aspect 74. The method of Aspect 72 or 73, wherein the transition metal catalyst comprises a palladium(II) catalyst.

Aspect 75. The method in any one of Aspects 72-74, wherein A has the structure XXII

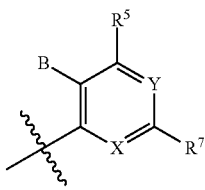

XXII wherein X is CR³ or N;
Y is CR⁶ or N; and
R⁵-R⁸ are independently hydrogen, an alkyl group, an alkoxy group, or a hydroxy group.

Aspect 76. The method of Aspect 75, wherein X is CR⁸ and Y is CR⁶.

Aspect 77. The method in any one of Aspects 72-76, wherein B is bromide or iodide.

Aspect 78. A compound having the structure XXIII

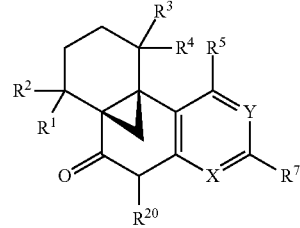

XXIII wherein X is CR⁸ or N;
Y is CR⁶ or N; and
R¹-R⁸ and R²⁰ are independently hydrogen, a substituted or unsubstituted alkyl group, an alkoxy group, or a hydroxy group.

Aspect 79. The compound of Aspect 78, wherein X is CR⁸ and Y is CR⁶.

Aspect 80. The compound of Aspect 78 or 79, wherein R⁶ and CR⁸ are an alkoxy group.

Aspect 81. The compound of anyone of Aspects 78-79, wherein R¹ and R² are each an alkyl group.

Aspect 82. The compound of anyone of Aspects 78-81, wherein R¹ and R² are each a methyl group.

Aspect 83. The compound of anyone of Aspects 78-82, wherein R³ and R⁴ are each hydrogen.

Aspect 84. The compound of anyone of Aspects 78-83, wherein R⁵ is an alkoxy group.

Aspect 85. The compound of anyone of Aspects 78-84, wherein R⁷ is an alkyl group.

Aspect 86. The compound of anyone of Aspects 78-85, wherein R⁷ is an isopropyl group.

Aspect 87. The compound of anyone of Aspects 78-86, wherein $R^8$ is hydrogen.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure.

Materials and Methods

General. Unless otherwise stated, reactions were conducted in oven-dried glassware (140° C.) under an atmosphere of nitrogen ($N_2$) using anhydrous solvents. Tetrahydrofuran (THF), 1,4-dioxane (dioxane) methylene chloride ($CH_2Cl_2$), diethyl ether ($Et_2O$), acetonitrile (MeCN) and toluene (PhMe) were dried by passage through activated alumina using a solvent purification system. Solvents used in photochemical reactions were degassed by 3 successive freeze-pump-thaw cycles and stored under inert atmosphere. N,N-Dicyclohexylmethylamine ($Cy_2NMe$) was distilled from CaH prior to use. β-Cyclocitral was purchased from Sigma and distilled prior to use. Benzylic alcohols (2-bromo-3,4-dimethoxyphenyl)methanol (6a) and 2-bromobenzyl alcohol (6b) were purchased and used directly as received. As outlined in FIG. S1, aryl fragments 6c-6i and alkyl fragments S1-S2 were synthesized following known literature procedures.[1-9] Burgess reagent (15) was prepared according to the published procedure in Organic Syntheses.[10] All other commercial reagents were used directly as received.

One representative reaction and yield of the product is described in detail; isolated yields reported are the average of at least two experimental replicates. The standard experimental error was ±5% yield. Photochemical reactions were carried out in a Rayonet RPR-100 chamber photoreactor equipped with 24 W UVA-lamps wherein ~90% of emission was centered at 350 nm (i.e. hv=350 nm). Column chromatography was carried out using silica gel 60 ($SiO_2$, 240-400 mesh) as stationary phase. Thin layer chromatography (TLC) was performed using pre-coated, glass-backed plates ($SiO_2$, 60 PF254, 0.25 mm) and visualized by UV light (254 nm) or by anisaldehyde or potassium permanganate staining.

$^1$H NMR spectra were recorded at 400 MHz, 600 MHz or 700 MHz and are reported relative to deuterated solvent signals. Data for $^1$H NMR spectra are reported as follows: chemical shift (ppm), multiplicity, coupling constant (Hz), and integration. Splitting patterns are abbreviated as follows: singlet (s), doublet (d), triplet (t), quartet (q), quintet (quint), multiplet (m), broad (br), apparent (app), and combinations thereof. $^{13}$C NMR spectra were recorded at 100 MHz or 150 MHz. Data for $^{13}$C NMR spectra are reported in order of carbon multiplicity (C=quaternary, CH=methine, $CH_2$=methylene, $CH_3$=methyl) and chemical shift. Carbon multiplicity was established by DEPT135 and/or HSQC experiments. Reported melting points of solids are uncorrected. IR spectra were recorded on an FT-IR spectrometer and reported in terms of frequency ($cm^{-1}$). Mass spectra were collected on an LCT spectrometer utilizing direct analysis in real time (DART) ionization.

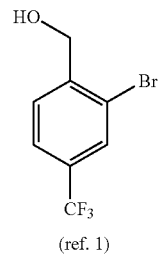

(ref. 1)

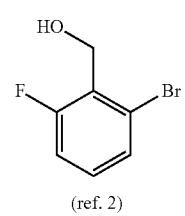

(ref. 2)

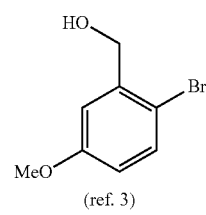

(ref. 3)

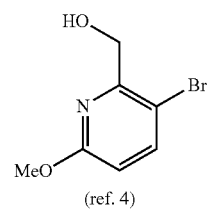

(ref. 4)

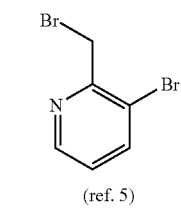

(ref. 5)

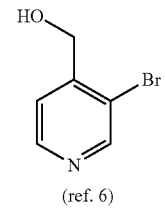

(ref. 6)

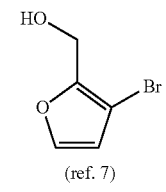

(ref. 7)

-continued

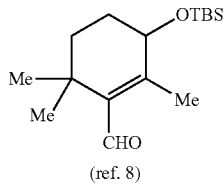

S1

(ref. 8)

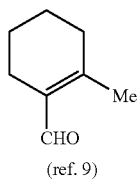

S2

(ref. 9)

Starting fragments prepared according to reported literature procedures.

Experimental Procedures and Characterization Data

I. Synthesis of phosphonates 7.

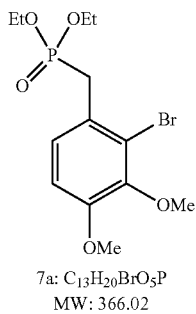

7a: C$_{13}$H$_{20}$BrO$_5$P
MW: 366.02

Phosphonate 7a. Following a modification of the protocol reported by Han,[11] a suspension of alcohol 6a (10.0 g, 40.5 mmol) and TBAI (1.50 g, 4.05 mmol) in P(OEt)$_3$ (14 mL, 81 mmol) was heated to 125° C. After 24 h, the resulting solution was cooled to r.t. and excess P(OEt)$_3$ was removed by vacuum distillation under reduced pressure. The resulting dark residue was digested in CH$_2$Cl$_2$ (50 mL) and washed with 1 M aq. HCl (2×50 mL), saturated aq. NaHCO$_3$ (2×50 mL) and brine (50 mL). The organic layer was dried over MgSO$_4$, filtered, and concentrated under reduced pressure. The resulting crude residue was purified by flash chromatography (SiO$_2$, 20:1→2:1 hexanes/EtOAc) to afford 7a (13.8 g, 37.7 mmol, 93% yield) as a yellow foam: $^1$H NMR (400 MHz, CDCl$_3$) δ 7.20 (dd, J=8.6, 3.0 Hz, 1H), 6.85 (d, J=8.6 Hz, 1H), 4.04 (p, J=7.2 Hz, 4H), 3.86 (s, 3H), 3.84 (s, 3H), 3.37 (d, J=21.1 Hz, 2H), 1.26 (t, J=7.0 Hz, 6H); $^{13}$C NMR (151 MHz, CDCl$_3$ δ C: 152.5 (d, J=3.3 Hz), 146.6, 124.5 (d, J=9.5 Hz), 120.9 (d, J=8.3 Hz), CH: 126.4 (d, J=5.5 Hz), 111.3 (d, J=3.3 Hz); CH$_2$: 62.2 (dd, J=6.7, 2.7 Hz), 33.2 (d, J=2.7 Hz), 32.3; CH$_3$: 60.4 (d, J=3.6 Hz), 56.1 (d, J=2.4 Hz), 16.4, 16.3; $^{31}$P NMR (160 MHz, CDCl$_3$) δ 23.5; IR (thin-film): 2960, 1795 cm$^{-1}$; HRMS-DART (m/z) [M+H]$^+$ calcd for C$_{13}$H$_{21}$BrO$_5$P=367.0310, found 367.0317.

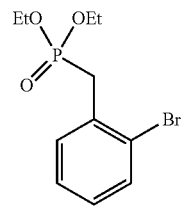

7b: C$_{11}$H$_{16}$BrO$_3$P
MW: 306.00

Following the procedure for 7a, the title compound was prepared by reacting 2-bromobenzyl alcohol (6b, 1.15 g, 6.13 mmol) with TBAI (226 mg, 0.613 mmol) in P(OEt)$_3$ (2.1 mL, 12 mmol). Purification by flash chromatography (SiO$_2$, 25:1 hexanes/Et$_2$O) afforded 7b (1.43 g, 4.66 mmol, 76%) as a yellow oil. Characterization data for 7b was identical to reported values.[12]

Phosphonate 7c.

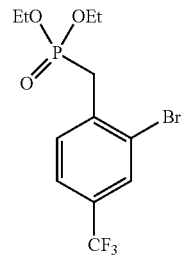

7c: C$_{12}$H$_{15}$BrF$_3$O$_3$P
MW: 375.12

Following the procedure for 7a, the title compound was prepared by reacting alcohol 6c (2.12 g, 8.30 mmol) with TBAI (307 mg, 0.830 mmol) in P(OEt)$_3$ (2.9 mL, 17 mmol). Purification by flash chromatography (SiO$_2$, 1:1 hexanes/EtOAc) afforded 7c as a colorless oil (1.93 g, 5.15 mmol, 62% yield): $^1$H NMR (400 MHz, CDCl$_3$) δ 7.83 (s, 1H), 7.58 (dd, J=8.2, 2.6 Hz, 1H), 7.53 (dd, J=8.5, 1.6 Hz, 1H), 4.08 (dq, J=8.0, 7.0 Hz, 4H), 3.44 (d, J=22.4 Hz, 2H), 1.28 (t, J=7.0 Hz, 6H); $^{13}$C NMR (100 MHz, CDCl$_3$) δ C: 136.4 (d, J=9.0 Hz), 130.5 (qd, J=33.1, 3.7 Hz), 124.8 (d, J=8.8 Hz), 122.5 (dd, J=272.3, 1.1 Hz); CH: 131.8 (d, J=5.0 Hz), 129.6 (p, J=3.8 Hz), 124.0 (p, J=3.7 Hz); CH$_2$: 62.2 (d, J=6.8 Hz), 33.4 (d, J=138.5 Hz), CH$_3$: 16.1 (d, J=6.1 Hz); $^{31}$P NMR (160 MHz, CDCl$_3$) δ 23.6; IR (thin-film): 2980, 1700, 1444 cm$^{-1}$; HRMS-DART (m/z) [M+H]$^+$ calculated for C$_{12}$H$_{16}$BrF$_3$O$_3$P=374.9972, found 374.9974.

Phosphonate 7d.

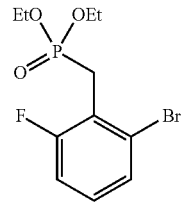

7d: C$_{11}$H$_{15}$BrFO$_3$P
MW: 325.11

Following the procedure for 7a, the title compound was prepared by reacting alcohol 6d (760 mg, 3.70 mmol) with TBAI (137 mg, 0.370 mmol) in P(OEt)$_3$ (1.3 mL, 7.4 mmol). Purification by flash chromatography (SiO$_2$, 1:1 hexanes/EtOAc) afforded 7d as a colorless oil (724 mg, 2.22 mmol, 60% yield): $^1$H NMR (400 MHz, CDCl$_3$) δ 7.38 (d, J=7.9 Hz, 1H), 7.16-7.07 (m, 1H), 7.04 (t, J=8.7 Hz, 1H), 4.09 (dd, J=7.1, 1.9 Hz, 4H), 3.44 (dd, J=22.0, 2.3 Hz, 2H), 1.28 (t, J=7.1 Hz, 6H); $^{13}$C NMR (150 MHz, CDCl$_3$) δ C: 161.1 (dd, J=251.0, 6.0 Hz), 125.6 (d, J=6.1 Hz), 121.4-120.6 (m), CH: 129.2-128.8 (m), 128.7 (t, J=3.4 Hz); 114.5 (dd, J=23.0, 3.6 Hz); CH$_2$: 62.3 (d, J=6.6 Hz), 27.8 (d, J=140.8 Hz); CH$_3$: 16.3 (d, J=6.1 Hz); $^{31}$P NMR (160 MHz, CDCl$_3$) δ 23.6 (d, J=4.2 Hz); IR (thin-film): 2983, 1573, 1450 cm$^{-1}$; HRMS-DART (m/z) [M+H]$^+$ calculated for C$_{11}$H$_{16}$BrFO$_3$P=325.0004, found 324.9992.

Phosphonate 7e.

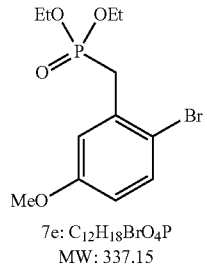 [SMILES: CCOP(=O)(Cc1cc(OC)ccc1Br)OCC]

7e: C$_{12}$H$_{18}$BrO$_4$P
MW: 337.15

Following the procedure for 7a, the title compound was prepared by reacting alcohol 6e (1.01 g, 4.65 mmol) with TBAI (172 mg, 0.465 mmol) in P(OEt)$_3$ (1.6 mL, 9.3 mmol). Purification by flash chromatography (SiO$_2$, 1:1 hexanes/EtOAc) afforded 7e as a colorless oil (754 mg, 2.23 mmol, 48% yield): $^1$H NMR (400 MHz, CDCl$_3$) δ 7.43 (dd, J=8.8, 1.2 Hz, 1H), 7.02 (t, J=3.0 Hz, 1H), 6.68 (dt, J=8.8, 2.7 Hz, 1H), 4.12-4.00 (m, 4H), 3.78 (s, 3H), 3.36 (d, J=22.0 Hz, 2H), 1.27 (t, J=7.0 Hz, 6H); $^{13}$C NMR (150 MHz, CDCl$_3$) δ C: 158.8, 132.7 (d, J=9.2 Hz), 115.3 (d, J=8.8 Hz), CH: 133.3 (d, J=3.0 Hz), 116.7 (d, J=5.0 Hz), 114.9 (d, J=3.7 Hz), CH$_2$: 62.3 (d, J=6.7 Hz), 33.6 (d, J=138.8 Hz); CH$_3$: 55.4, 16.3 (d, J=6.0 Hz); $^{31}$P NMR (160 MHz, CDCl$_3$) δ 25.1; IR (thin-film): 2981, 1596, 1475 cm$^{-1}$; HRMS-DART (m/z) [M+H]$^+$ calculated for C$_{12}$H$_{19}$BrO$_4$P=337.0204, found 337.0202.

Phosphonate 7f.

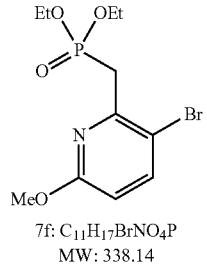 [SMILES: CCOP(=O)(Cc1nc(OC)ccc1Br)OCC]

7f: C$_{11}$H$_{17}$BrNO$_4$P
MW: 338.14

Following the procedure for 7a, the title compound was prepared by reacting alcohol 6f (872 mg, 4.00 mmol) with TBAI (148 mg, 0.400 mmol) in P(OEt)$_3$ (1.4 mL, 8.0 mmol). Purification by flash chromatography (SiO$_2$, 1:1 hexanes/EtOAc) afforded 7f as a colorless oil (1.23 g, 3.65 mmol, 89% yield): $^1$H NMR (400 MHz, CDCl$_3$) δ 7.65 (dd, J=8.7, 1.0 Hz, 1H), 6.52 (dd, J=8.7, 2.4 Hz, 1H), 4.20-4.06 (m, 4H), 3.90 (d, J=1.9 Hz, 3H), 3.55 (dd, J=22.4, 1.7 Hz, 2H), 1.30 (t, J=7.1 Hz, 7H); $^{13}$C NMR (151 MHz, CDCl$_3$) δ C: 162.2, 148.68 (d, J=8.6 Hz), 112.21 (d, J=8.7 Hz); CH: 142.6, 110.9 (d, J=3.9 Hz); CH$_2$: 62.0 (d, J=6.2 Hz), 35.3 (d, J=136.4 Hz); CH$_3$: 53.5, 16.3 (d, J=6.3 Hz); $^{31}$P NMR (160 MHz, CDCl$_3$) δ 23.8; IR (thin-film): 2982, 1578, 1460 cm$^{-1}$; HRMS-DART (m/z) [M+H]$^+$ calculated for C$_{11}$H$_{18}$BrNO$_4$P=338.0157, found 338.0161.

Phosphonate 7i.

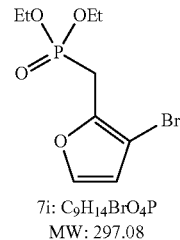

7i: C$_9$H$_{14}$BrO$_4$P
MW: 297.08

Following the procedure for 7a, the title compound was prepared by reacting alcohol 6i (230 mg, 1.30 mmol) with TBAI (48 mg, 0.13 mmol) in P(OEt)$_3$ (0.5 mL, 2.6 mmol). Purification by flash chromatography (SiO$_2$, 2:1 hexanes/EtOAc) afforded 7i as a colorless oil (175 mg, 0.65 mmol, 50% yield): $^1$H NMR (400 MHz, CDCl$_3$) δ 7.34 (t, J=2.3 Hz, 1H), 6.40 (d, J=2.0 Hz, 1H), 4.17-4.05 (m, 4H), 3.26 (d, J=20.6 Hz, 2H), 1.30 (t, J=7.1 Hz, 7H); $^{13}$C NMR (100 MHz, CDCl$_3$) δ C: 143.7 (d, J=13.3 Hz), 98.7 (d, J=11.3 Hz), CH: 142.4 (d, J=3.7 Hz), 113.9 (d, J=3.3 Hz), CH$_2$: 62.4 (d, J=6.6 Hz), 25.8, 24.4, CH$_3$: 16.3 (d, J=5.9 Hz); $^{31}$P NMR (160 MHz, CDCl$_3$) δ 24.2; IR (thin-film): 2983, 2909, 1596 cm$^{-1}$; HRMS-DART (m/z) [M+H]$^+$ calculated for C$_9$H$_{15}$BrO$_4$P=296.9891, found 296.9888.

As described below, N-heterocyclic phosphonates 7g and 7h were prepared from the corresponding benzylic halides via a Michaelis-Arbuzov reaction.

Phosphonate 7g.

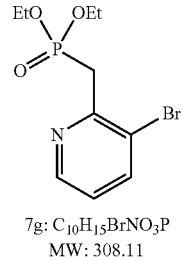

7g: C$_{10}$H$_{15}$BrNO$_3$P
MW: 308.11

A solution of bromide 6g (753 mg, 3.00 mmol) and P(OEt)$_3$ (2.1 mL, 12 mmol) in toluene (2.3 mL) was heated to 120° C. After 24 h, the reaction was cooled to r.t. and concentrated under reduced pressure. The resulting crude residue was purified by flash chromatography (SiO$_2$, 12:1 EtOAc/MeOH) to afford 7g (767 mg, 2.49 mmol, 83% yield) as a yellow oil: $^1$H NMR (400 MHz, CDCl$_3$) δ 8.44 (d, J=4.1 Hz, 1H), 7.79 (d, J=8.0 Hz, 1H), 7.00 (ddd, J=8.1, 4.7, 2.2 Hz, 1H), 4.14-3.99 (m, 4H), 3.61 (d, J=22.8 Hz, 2H), 1.23 (t, J=7.1 Hz, 7H); $^{13}$C NMR (101 MHz, CDCl$_3$) δ C: 152.2, 121.8; CH: 147.9, 140.5, 123.2; CH$_2$: 62.3, 36.6, 35.2; CH$_3$: 16.3; $^{31}$P NMR (160 MHz, CDCl$_3$) δ 23.6; IR (thin-film):

2950, 1705, 1440 cm$^{-1}$; HRMS-DART (m/z) [M+H]$^+$ calculated for $C_{10}H_{16}BrNO_3P$=308.0051; 308.0053 found.

3-bromo-4-chloromethylpyridine (S3)

S3: $C_6H_5BrClN$
MW: 206.47

A solution of 6h (960 mg, 5.11 mmol) in $CH_2Cl_2$ (10 mL) was cooled to 0° C. Thionyl chloride (1.1 mL, 15 mmol) was added drop-wise via syringe. Upon complete addition, the reaction was warmed to r.t. After 2 h, the reaction was treated with saturated aq. $NaHCO_3$ (10 mL). The resulting slurry was transferred to a separatory funnel and extracted with $CH_2Cl_2$ (3×5 mL). The combined organic extracts were washed with brine (20 mL), dried over $MgSO_4$, filtered, and concentrated under reduced pressure to afford S3 (1.10 g, 4.89 mmol, 96% yield) as a yellow oil. This material was of sufficient purity to use in the next step without purification: $^1$H NMR (600 MHz, $CDCl_3$) δ 8.73 (s, 1H), 8.55 (d, J=5.0 Hz, 1H), 7.47 (dd, J=4.9, 0.7 Hz, 1H), 4.64 (s, 2H); $^{13}$C NMR (150 MHz, $CDCl_3$) δ C: 144.9, 121.6; CH: 152.1, 148.9, 124.6; $CH_2$: 44.1; IR (thin-film): 3042, 2964, 1580, 1396 cm$^{-1}$; HRMS-DART (m/z) [M+H]$^+$ calculated for $C_6H_6BrClN$=205.9372, found=205.9365.

Phosphonate 7h.

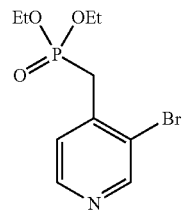

7h: $C_{10}H_{15}BrNO_3P$
MW: 308.11

A solution of S3 (960 mg, 4.65 mmol) and P(OEt)$_3$ (3.2 mL, 18.6 mmol) in toluene (2.3 mL) was heated to 120° C. After 24 h, the reaction was cooled to r.t. and concentrated under reduced pressure. The resulting crude residue was purified by flash chromatography (SiO$_2$, 9:1 EtOAc/MeOH) to afford 7h (1.11 g, 3.60 mmol, 78% yield) as a yellow oil: $^1$H NMR (600 MHz, $CDCl_3$) δ 8.71 (s, 1H), 8.44 (d, J=5.0 Hz, 1H), 7.39 (dd, J=5.0, 2.6 Hz, 1H), 4.14-4.02 (m, 4H), 3.37 (d, J=22.6 Hz, 2H), 1.28 (t, J=7.1 Hz, 6H); $^{13}$C NMR (150 MHz, $CDCl_3$) δ C: 141.2 (d, J=8.4 Hz), 123.5 (d, J=8.3 Hz); CH: 152.1 (d, J=3.1 Hz), 148.1 (d, J=2.9 Hz), 126.3 (d, J=4.9 Hz); $CH_2$: 62.6 (d, J=6.7 Hz), 33.1 (d, J=137.7 Hz); $CH_3$: 16.3 (d, J=6.1 Hz); $^{31}$P NMR (162 MHz, $CDCl_3$) δ 22.95; IR (thin-film): 2983, 2908, 1583, 1476 cm$^{-1}$; HRMS-ESI (m/z) [M+H]$^+$ calculated for $C_{10}H_{16}BrNO_3P$=308.0051, found=308.0044.

II. Synthesis of β-Ionyl Photosubstrates 3.

Procedure A. A solution of phosphonate 7 (1.1 equiv) in THF (0.5 M) was cooled to −78° C. and LiHMDS (1.1 equiv, 1.0 M in THF) was added drop-wise via syringe. After 30 min, a solution of β-cyclocitral (1.0 equiv) in THF (0.5 M) was added and the reaction mixture was warmed to r.t. in a water bath over 0.5 h. The reaction was then heated to 65° C. until β-cyclocitral was consumed, as judged by TLC (ca. 3-6 h). Once complete, the reaction mixture was treated with saturated aq. $NH_4Cl$ (1 mL/mmol). The resulting slurry was transferred to a separatory funnel and extracted with EtOAc (3×10 mL/mmol). The combined organic extracts were washed with water and brine, dried over $MgSO_4$, filtered, and concentrated under reduced pressure. The resulting residue was purified by flash chromatography.

Procedure B. A solution of phosphonate 7 (1.1 equiv) in dioxane (0.5 M) was cooled to −78° C. and LiHMDS (1.1 equiv, 1.0 M in THF) was added drop-wise via syringe. After 30 min, a solution of β-cyclocitral (1.0 equiv) in dioxane (0.5 M) was added and the reaction mixture was warmed to r.t. in a water bath over 0.5 h. The reaction was then heated to 100° C. until β-cyclocitral was consumed, as judged by TLC (ca. 3-6 h). Once complete, the reaction was cooled to r.t. and treated with saturated aq. $NH_4Cl$ (1 mL/mmol). The resulting slurry was transferred to a separatory funnel and extracted with EtOAc (3×10 mL/mmol). The combined organic extracts were washed with water and brine, dried over $MgSO_4$, filtered, and concentrated under reduced pressure. The resulting residue was purified by flash chromatography.

Photosubstrate (E)-3a.

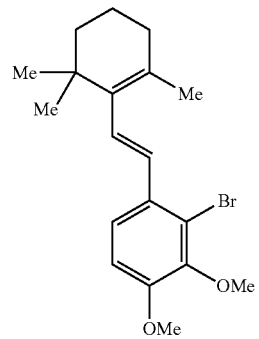

(E)-3a: $C_{19}H_{25}BrO_2$
MW: 365.31

Following Procedure A, the title compound was prepared from 7a (6.48 g, 17.7 mmol) and β-cyclocitral (2.45 g, 16.1 mmol). Purification by flash chromatography (SiO$_2$, 20:1 hexanes/Et$_2$O) afforded 3a (5.52 g, 15.1 mmol, 94% yield) as a yellow oil: $^1$H NMR (400 MHz, $CDCl_3$) δ 7.81-7.77 (m, 1H), 7.79 (s, 1H), 7.53-7.46 (m, 1H), 7.49 (d, J=8.2 Hz, 1H), 7.29 (d, J=8.0 Hz, 1H), 5.30 (t, J=7.2 Hz, 1H), 5.05-4.98 (m, 1H), 4.58 (d, J=2.6 Hz, 1H), 3.62 (d, J=7.2 Hz, 2H), 2.22 (t, J=6.3 Hz, 2H), 1.76-1.63 (m, 2H), 1.52-1.44 (m, 2H), 1.06 (s, 6H); $^{13}$C NMR (150 MHz, $CDCl_3$) δ C: 152.4, 146.5, 137.4, 132.3, 129.9, 119.5, 34.2; CH: 131.5, 129.0, 121.6, 111.6; $CH_2$: 39.6, 33.0, 19.3; $CH_3$: 60.4, 56.2, 28.9, 21.7; IR (thin-film): 2928, 1484 cm$^{-1}$; HRMS-DART (m/z) [M+H]$^+$ calculated for $C_{19}H_{26}BrO_2$=365.1116, found=365.1109. UV-VIS (THF): $\pi_{max}$=288 nm.

Photosubstrate 3b.

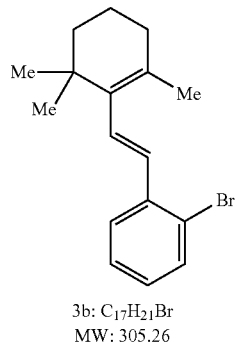

3b: C$_{17}$H$_{21}$Br
MW: 305.26

Following Procedure A, the title compound was prepared from 7b (825 mg, 7.23 mmol) and β-cyclocitral (1.00 g, 6.57 mmol). Purification by flash chromatography (SiO$_2$, 40:1 hexanes/Et$_2$O) afforded 3a (1.62 g, 5.32 mmol, 81% yield) as a colorless oil: $^1$H NMR (400 MHz, CDCl$_3$) δ 7.59-7.50 (m, 2H), 7.30-7.23 (m, 1H), 7.07 (td, J=7.6, 1.7 Hz, 1H), 6.70 (d, J=16.2 Hz, 1H), 6.58 (dd, J=16.4, 1.9 Hz, 1H), 2.05 (t, J=6.3 Hz, 2H), 1.83-1.78 (m, 3H), 1.70-1.60 (m, 2H), 1.54-1.47 (m, 2H), 1.09 (s, 6H); $^{13}$C NMR (125 MHz, CDCl$_3$) δ C: 138.3, 137.3, 130.4, 123.6, 34.2; CH: 132.8, 131.7, 130.6, 128.1, 127.4, 126.7; CH$_2$: 39.6, 33.0, 19.3; CH$_3$: 28.9, 21.8; IR (thin-film): 2926, 1464 cm$^{-1}$; HRMS-DART (m/z) [M+H]$^+$ calculated for C$_{17}$H$_{22}$Br=305.0905, found 305.0884. UV-VIS (THF): λ$_{max}$=284 nm.

Photosubstrate 3c.

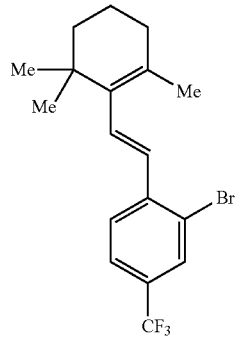

3c: C$_{18}$H$_{20}$BrF$_3$
MW: 373.26

Following Procedure A, the title compound was prepared from 7c (2.21 g, 2.20 mmol) and β-cyclocitral (304 mg, 2.00 mmol). Purification by flash chromatography (SiO$_2$, 20:1 hexanes/Et$_2$O) afforded 3c (553 mg, 1.48 mmol, 74% yield) as a yellow oil: $^1$H NMR (600 MHz, CDCl$_3$) δ 7.81 (s, 1H), 7.64 (d, J=8.2 Hz, 1H), 7.51 (dd, J=8.2, 1.9 Hz, 1H), 6.71 (d, J=3.7 Hz, 2H), 2.07 (t, J=6.3 Hz, 2H), 1.81 (s, 3H), 1.70-1.61 (m, 2H), 1.53-1.46 (m, 2H), 1.09 (s, 6H); $^{13}$C NMR (150 MHz, CDCl$_3$) δ C: 141.8, 137.1, 131.5, 130.1, 123.3, 122.4, 34.2; CH: 133.1, 130.5, 129.9 (d, J=4.1 Hz), 126.7, 124.2 (d, J=4.1 Hz); CH$_2$: 39.6, 33.1, 19.2; CH$_3$: 28.9, 21.7; $^{19}$F NMR (376 MHz, CDCl$_3$) δ −62.6; IR (thin-film): 2930, 1607 cm$^{-1}$; HRMS-DART (m/z) [M+H]$^+$ calculated for C$_{18}$H$_{21}$F$_3$Br=373.0779, found=373.0749. UV-VIS (THF): λ$_{max}$=299 nm.

Photosubstrate 3d.

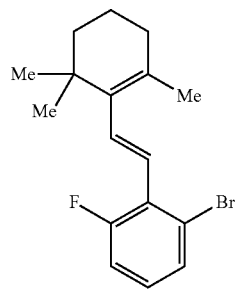

3d: C$_{17}$H$_{20}$BrF
MW: 323.25

Following Procedure A, the title compound was prepared from 7d (715 mg, 2.20 mmol) and β-cyclocitral (304 mg, 2.00 mmol). Purification by flash chromatography (SiO$_2$, 20:1 hexanes/Et$_2$O) afforded 3d (498 mg, 1.54 mmol, 77% yield) as a yellow oil: $^1$H NMR (400 MHz, CDCl$_3$) δ 7.41-7.34 (m, 1H), 7.08-6.97 (m, 2H), 6.74 (d, J=16.6 Hz, 1H), 6.34 (d, J=16.6 Hz, 1H), 2.05 (t, J=6.4 Hz, 2H), 1.83 (d, J=1.1 Hz, 3H), 1.83 (s, 3H), 1.70-1.60 (m, 2H), 1.53-1.46 (m, 2H), 1.09 (s, 6H); $^{13}$C NMR (150 MHz, CDCl$_3$) δ C: 160.6 (d, J=251.7 Hz), 138.0, 130.0, 127.0 (d, J=15.1 Hz), 124.6 (d, J=4.8 Hz), 34.1; CH: 136.0 (d, J=10.3 Hz), 128.5 (d, J=3.4 Hz), 127.9 (d, J=9.6 Hz), 125.7 (d, J=2.8 Hz), 115.1 (d, J=23.8 Hz); CH$_2$: 39.5, 32.9, 19.3; CH$_3$: 28.8, 21.7; IR (thin-film): 2927, 1455 cm$^{-1}$; HRMS-DART (m/z) [M+H]$^+$ calculated for C$_{17}$H$_{21}$BrF=323.0811, found 323.0802. UV-VIS (THF): π$_{max}$=289 nm.

Photosubstrate 3e.

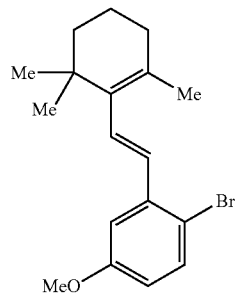

3e: C$_{18}$H$_{23}$BrO
MW: 335.29

Following Procedure A, the title compound was prepared from 7e (742 mg, 2.20 mmol) and β-cyclocitral (304 mg, 2.00 mmol). Purification by flash chromatography (SiO$_2$, 20:1 hexanes/Et$_2$O) afforded 3e (543 mg, 1.62 mmol, 81% yield) as a yellow oil: $^1$H NMR (400 MHz, CDCl$_3$) δ 7.43 (d, J=8.8 Hz, 1H), 7.08 (d, J=3.0 Hz, 1H), 6.72-6.62 (m, 2H), 6.57 (d, J=16.3 Hz, 1H), 3.82 (s, 3H), 2.05 (t, J=6.4 Hz, 2H), 1.80 (s, 3H), 1.71-1.61 (m, 2H), 1.54-1.47 (m, 2H), 1.09 (s, 6H); $^{13}$C NMR (150 MHz, CDCl$_3$) δ C: 159.0, 139.0, 137.3, 130.5, 114.5, 34.2; CH: 133.3, 131.7, 130.7, 114.0, 112.1; CH$_2$: 39.6, 33.0, 19.2; CH$_3$: 55.5, 28.9, 21.7; IR (thin-film): 2928, 1461 cm$^{-1}$; HRMS-DART (m/z) [M+H]$^+$ calculated for C$_{18}$H$_{24}$BrO=335.1010, found 335.0989; UV-VIS (THF): λ$_{max}$=286 nm.

Photosubstrate 3f.

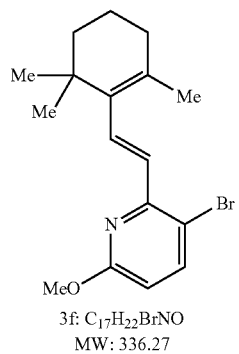

3f: C₁₇H₂₂BrNO
MW: 336.27

Following Procedure A, the title compound was prepared from 7f (743 mg, 2.20 mmol) and β-cyclocitral (304 mg, 2.00 mmol). Purification by flash chromatography (SiO₂, 10:1 hexanes/Et₂O) afforded 3f (470 mg, 1.40 mmol, 70% yield) as a yellow oil: ¹H NMR (600 MHz, CDCl₃) δ 7.62 (d, J=8.6 Hz, 1H), 7.54 (d, J=16.0 Hz, 1H), 6.86 (d, J=15.7 Hz, 1H), 6.46 (d, J=8.6 Hz, 1H), 3.95 (s, 3H), 2.13-2.02 (m, 2H), 1.90-1.79 (m, 3H), 1.71-1.60 (m, 2H), 1.54-1.47 (m, 2H), 1.13 (s, 6H); ¹³C NMR (150 MHz, CDCl₃) δ C: 162.0, 150.6, 137.2, 132.4, 111.1, 34.3; CH: 142.7, 134.6, 128.1, 110.5; CH₂: 40.0, 33.5, 19.2; CH₃: 53.3, 29.0, 21.8; IR (thin-film): 2928, 1456, 1410 cm⁻¹; HRMS-DART (m/z) [M+H]⁺ calculated for C₁₇H₂₃BrNO=336.0963, found 336.0967; UV-VIS (THF): λ₁=252 nm, λ₂=331 nm.

Photosubstrate 3g.

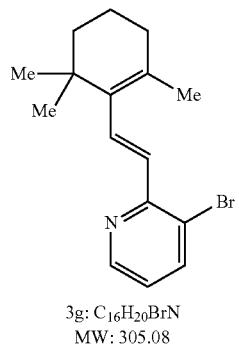 [SMILES: CC1=C(/C=C/c2ncccc2Br)C(C)(C)CCC1]

3g: C₁₆H₂₀BrN
MW: 305.08

Following Procedure B, the title compound was prepared from 7g (743 mg, 2.20 mmol) and β-cyclocitral (304 mg, 2.00 mmol). Purification by flash chromatography (SiO₂, 10:1 hexanes/Et₂O) afforded 3g (470 mg, 1.40 mmol, 70% yield) as a yellow oil: ¹H NMR (600 MHz, CDCl₃) δ 8.49 (dd, J=4.6, 1.5 Hz, 1H), 7.81 (dd, J=8.0, 1.5 Hz, 1H), 7.46 (d, J=15.7 Hz, 1H), 6.97 (dd, J=8.0, 4.6 Hz, 1H), 6.93 (d, J=15.7 Hz, 1H), 2.08 (t, J=6.3 Hz, 2H), 1.84 (s, 3H), 1.68-1.61 (m, 2H), 1.53-1.48 (m, 2H), 1.13 (s, 6H); ¹³C NMR (151 MHz, CDCl₃) δ C: 153.8, 137.4, 132.2, 128.6, 120.5, CH: 148.0, 140.5, 135.2, 128.6, 122.4, CH₂: 39.8, 33.4, 19.2, CH₃: 34.3, 29.1, 21.9; IR (thin film): 3039, 2925, 1615 cm⁻¹; HRMS-DART (m/z) [M+H]⁺ calculated for C₁₆H₂₁BrN=306.0857, found=306.0857.

Photosubstrate 3h.

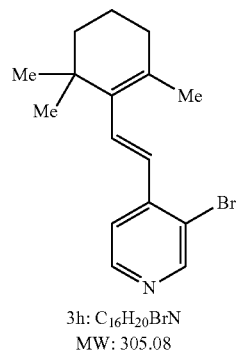

3h: C₁₆H₂₀BrN
MW: 305.08

Following a modification of Procedure B, the title compound was prepared from 7h (743 mg, 2.20 mmol) and β-cyclocitral (304 mg, 2.00 mmol). Purification by flash chromatography (SiO₂, 10:1 hexanes/Et₂O) afforded 3h (470 mg, 1.40 mmol, 70% yield) as a yellow oil: ¹H NMR (600 MHz, CDCl₃) δ 8.66 (s, 1H), 8.41 (d, J=5.1 Hz, 1H), 7.42 (d, J=5.1 Hz, 1H), 6.87 (d, J=16.3 Hz, 1H), 6.66 (d, J=16.3 Hz, 1H), 2.10-2.04 (m, 2H), 1.84-1.76 (m, 3H), 1.68-1.61 (m, 2H), 1.53-1.48 (m, 2H), 1.09 (s, 6H); ¹³C NMR (150 MHz, CDCl₃) δ C: 145.2, 136.9, 132.6, 121.4, 34.2; CH: 152.4, 148.0, 134.7, 128.9, 120.3; CH₂: 39.6, 33.2, 19.1; CH₃: 28.9, 21.8; IR (thin-film): 3037, 2927, 1574, 1459 cm⁻¹; HRMS-DART (m/z) [M+H]⁺ calculated for C₁₆H₂₁BrN=306.0857, found=306.0836.

Note: Structure 3h was contaminated with ~10% isomer 3h-2 (inset, left). This impurity could not be removed by chromatography. It proved to be inconsequential to the subsequent photoisomerization and Heck steps, and was removed from 5h by column chromatography.

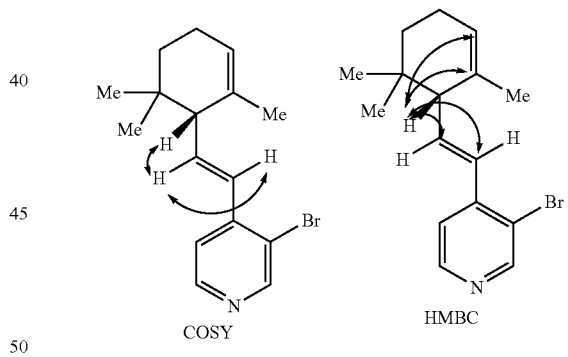

COSY  HMBC

Photosubstrate 3i.

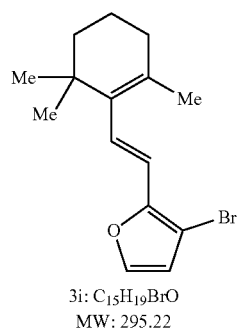

3i: C₁₅H₁₉BrO
MW: 295.22

Following Procedure A, the title compound was prepared from 7i (297 mg, 1.00 mmol) and β-cyclocitral (138 mg, 0.91 mmol). Purification by flash chromatography (SiO$_2$, 99:1 hexanes/Et$_2$O) afforded 3i (62 mg, 0.38 mmol, 42% yield) as an orange oil: $^1$H NMR (400 MHz, CDCl$_3$) δ 7.30 (d, J=2.0 Hz, 1H), 6.73 (d, J=16.4 Hz, 1H), 6.43 (d, J=2.0 Hz, 1H), 6.25 (d, J=16.4 Hz, 1H), 2.04 (t, J=6.4 Hz, 2H), 1.78 (s, 3H), 1.66-1.59 (m, 2H), 1.52-1.45 (m, 2H), 1.08 (s, 6H); $^{13}$C NMR (100 MHz, CDCl$_3$) δ C: 150.2, 137.1, 130.9, 97.0, 34.2; CH: 141.3, 128.3, 117.9, 114.8; CH$_2$: 39.7, 33.2, 19.2; CH$_3$: 28.9, 21.7; IR (thin-film): 3369, 2929 cm$^{-1}$; HRMS-DART (m/z) [M+H]$^+$ calculated for C$_{15}$H$_{20}$BrO=295.0697, found 295.0636; UV-VIS (THF): π$_{max}$=283 nm.

Photosubstrate 3k.

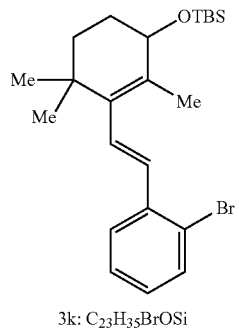

3k: C$_{23}$H$_{35}$BrOSi
MW: 435.52

Following a modification of Procedure A, the title compound was prepared from 7b (417 mg, 1.36 mmol) and S1 (351 mg, 1.24 mmol). Purification by flash chromatography (SiO$_2$, 99:1 hexanes/Et$_2$O) afforded 3k (406 mg, 0.932 mmol, 75% yield) as a yellow oil: $^1$H NMR (400 MHz, CDCl$_3$) δ 7.59-7.51 (m, 2H), 7.32-7.26 (m, 1H), 7.09 (td, J=7.6, 1.7 Hz, 1H), 6.73 (d, J=16.3 Hz, 1H), 6.55 (dt, J=16.3, 1.3 Hz, 1H), 4.08 (t, J=5.7 Hz, 1H), 1.91-1.79 (m, 4H), 1.76-1.62 (m, 2H), 1.49-1.36 (m, 1H), 1.12 (s, 3H), 1.05 (s, 3H), 0.93 (s, 9H), 0.12 (s, 3H), 0.12 (s, 3H); $^{13}$C NMR (150 MHz, CDCl$_3$) δ C: 139.6, 132.2, 123.7, 34.7, 18.4, 18.2; CH: 132.9, 132.5, 130.5, 128.3, 127.4, 126.8, 71.2; CH$_2$: 35.4, 29.3; CH$_3$: 28.5, 28.4, 26.0, -4.2, -4.6; IR (thin-film): 2930, 1464 cm$^{-1}$; HRMS-ESI (m/z) [M+Na]$^+$ calculated for C$_{23}$H$_{35}$BrOSiNa=457.1538, found 457.1534; UV-VIS (THF): λ$_{max}$=273 nm.

Photosubstrate 3l.

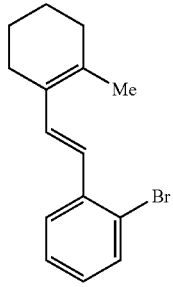

3l: C$_{15}$H$_{17}$Br
MW: 277.21

Following a modification of Procedure A, the title compound was prepared from 7b (336 mg, 1.10 mmol) and S2 (124 mg, 1.00 mmol). Purification by flash chromatography (SiO$_2$, 99:1 hexanes/Et$_2$O) afforded 3l (202 mg, 0.731 mmol, 73% yield) as a yellow oil: $^1$H NMR (400 MHz, CDCl$_3$) δ 7.32 (d, J=8.7 Hz, 1H), 7.09 (d, J=15.9 Hz, 1H), 6.88 (d, J=8.7 Hz, 1H), 6.77 (d, J=15.9 Hz, 1H), 3.90 (s, 3H), 3.87 (s, 3H), 2.37-2.30 (m, 2H), 2.18-2.11 (m, 2H), 1.89 (s, 3H), 1.77-1.61 (m, 4H); $^{13}$C NMR (150 MHz, CDCl$_3$) δ C: 152.3, 146.4, 135.1, 132.3, 128.2, 119.7; CH: 128.9, 123.2, 121.5, 111.6; CH$_2$: 33.3, 25.6, 22.9, 22.9; CH$_3$: 60.4, 56.1, 19.5; IR (thin-film): 3011, 2988, 1499 cm$^{-1}$; HRMS-DART (m/z) [M+H]$^+$ calculated for C$_{15}$H$_{18}$Br=277.0692, found=277.0690.

Photosubstrates (Z)-3a and 3j were prepared from (E)-3a and 3k, respectively. Detailed procedures are provided below.

Photosubstrate (Z)-3a.

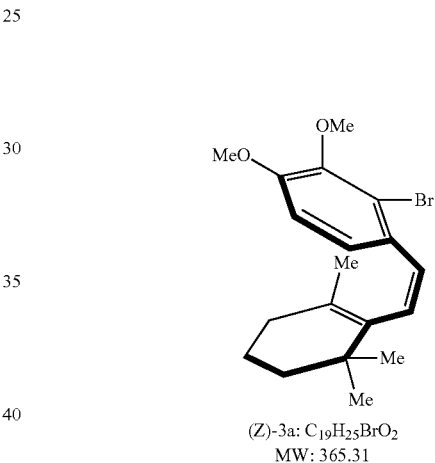

(Z)-3a: C$_{19}$H$_{25}$BrO$_2$
MW: 365.31

Following a modification of the procedure reported by Weaver,[11] a 1-dram borosilicate vial was charged with Ir(ppy)$_3$ (3 mg, 0.005 mmol) and (E)-3a (37 mg, 0.10 mmol). Degassed MeCN (1.0 mL) was added via syringe and the vial was sealed under a positive pressure of nitrogen. The solution was irradiated with a 50 W blue LED lamp (hv=430 nm) during which time the internal temperature reached 40° C. After 3 h, the reaction was removed from light, cooled to r.t., and concentrated under reduced pressure. The resulting crude residue was purified by pTLC (4:1 hexanes/MTBE) to afford (Z)-3a (16 mg, 0.043 mmol, 43% yield) as a colorless oil: $^1$H NMR (400 MHz, CDCl$_3$) δ 7.30 (d, J=8.7 Hz, 1H), 6.76 (d, J=8.8 Hz, 1H), 6.59 (d, J=12.4 Hz, 1H), 6.15 (d, J=12.4 Hz, 1H), 3.88 (s, 3H), 3.86 (s, 3H), 1.88 (app t, J=5.4 Hz, 2H), 1.67-1.60 (m, 2H), 1.54-1.48 (m, 2H), 1.29 (s, 3H), 1.1 (s, 6H); $^{13}$C NMR (150 MHz, CDCl$_3$) δ C: 151.9, 134.2, 131.6, 129.4, 119.9, 134.5; CH: 129.3, 129.2, 124.0, 110.8; CH$_2$: 39.3, 32.2, 19.2; CH$_3$: 60.4, 56.0, 28.8, 21.3; IR (thin-film): 3001, 2992, 1403 cm$^{-1}$; HRMS-DART (m/z) [M+H]$^+$ calculated for C$_{19}$H$_{26}$BrO$_2$=366.1194, found=366.1199

Photosubstrate 3j.

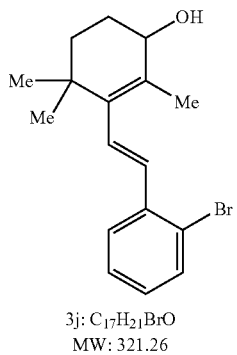 [SMILES: CC1=C(/C=C/c2ccccc2Br)C(C)(C)CCC1O]

3j: C$_{17}$H$_{21}$BrO
MW: 321.26

A solution of 3j A solution of 3k (180 mg, 0.413 mmol) in THF (1.4 mL) was cooled to 0° C. A solution of TBAF (0.4 mL, 0.4 mmol, 1 M in THF) was added, and the reaction was warmed to r.t. After 10 min, water (1.4 mL) was added. The resulting slurry was transferred to a separatory funnel and extracted with EtOAc (3×15 mL). The combined organic extracts were washed with brine (1×5 mL), dried with MgSO$_4$, filtered, and concentrated under reduced The resulting crude residue was purified by column chromatography (SiO$_2$, 10:1 hexane/EtOAc) to afford 3j (126 mg, 0.392 mmol, 95% yield) as a colorless solid: mp=87-90° C.; $^1$H NMR (400 MHz, CDCl$_3$) δ 7.59-7.52 (m, 2H), 7.29 (t, J=7.9 Hz, 1H), 7.10 (td, J=7.7, 1.6 Hz, 1H), 6.74 (d, J=16.3 Hz, 1H), 6.54 (d, J=16.3 Hz, 1H), 4.05 (t, J=4.8 Hz, 1H), 2.01-1.88 (m, 1H), 1.93 (s, 3H), 1.80-1.64 (m, 2H), 1.51-1.42 (m, 1H), 1.11 (s, 3H), 1.08 (s, 3H); $^{13}$C NMR (150 MHz, CDCl$_3$) δ C: 141.3, 137.9, 130.7, 123.7, 34.8; CH: 132.9, 132.9, 129.8, 128.5, 127.5, 126.8, 70.2; CH$_2$: 34.6, 28.5; CH$_3$: 29.0, 27.4, 18.6; IR (thin-film): 3328, 2933, 1465 cm$^{-1}$; HRMS-ESI (m/z) [M+Na]$^+$ calculated for C$_{17}$H$_{22}$BrO=343.0673, found 343.0679; UV-VIS (THF): λ$_{max}$=277 nm.

II. Photoisomerization of 3 to 'Disrupted' Polyenes 4 (in Table 1 and Scheme 1)

Diene 4a.

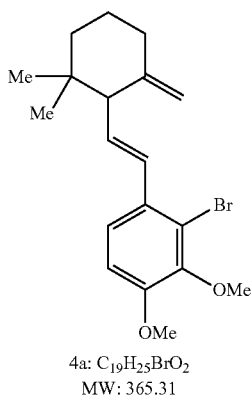 [SMILES: C=C1CCCC(C)(C)C1/C=C/c1ccc(OC)c(OC)c1Br]

4a: C$_{19}$H$_{25}$BrO$_2$
MW: 365.31

General Procedure: A 1-dram vial was charged with a solution of (E)-3a (73 mg, 0.20 mmol) in oxygen-free dioxane (1.0 mL) and capped under a positive pressure of nitrogen. The vial was transferred to a Rayonet chamber photoreactor preheated to 35° C. and exposed to 300 nm UV-light until the reaction was judged to be complete by $^1$H NMR spectroscopy. After 5 h, the reaction was removed from the photoreactor, cooled to r.t., and concentrated under reduced pressure. The resulting crude residue was purified by flash chromatography (SiO$_2$, 97:3 hexanes/EtOAc) to afford 4a (63.6 mg, 0.174 mmol, 87% yield) as a yellow oil: $^1$H NMR (400 MHz, CDCl$_3$) δ 6.89 (d, J=8.5 Hz, 1H), 6.81 (d, J=8.4 Hz, 1H), 5.31 (t, J=7.2 Hz, 1H), 5.03-4.97 (m, 1H), 4.60 (d, J=2.7 Hz, 1H), 3.85 (s, 6H), 3.53 (d, J=7.2 Hz, 2H), 2.22 (t, J=6.3 Hz, 2H), 1.74-1.64 (m, 2H), 1.52-1.45 (m, 2H), 1.06 (s, 6H); $^{13}$C NMR (150 MHz, CDCl$_3$) δ C: 151.7, 150.5, 146.5, 146.1, 134.8, 120.4, 38.1; CH: 124.4, 117.0, 111.3, CH$_2$: 111.5, 41.6, 37.4, 34.8, 23.5, CH$_3$: 60.4, 56.1, 27.6; IR (thin-film): 2852, 1116 cm$^{-1}$; HRMS-ESI (m/z) [M+H]$^+$ calculated for C$_{19}$H$_{26}$BrO$_2$=365.1116, found=365.1099.

Diene 4b.

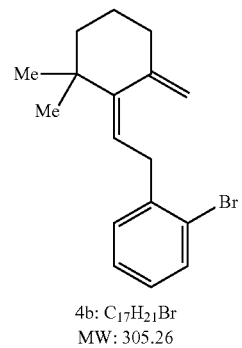 [SMILES: C=C1CCCC(C)(C)/C1=C/Cc1ccccc1Br]

4b: C$_{17}$H$_{21}$Br
MW: 305.26

Following the procedure for 4a, the title compound was prepared from 3b (61 mg, 0.20 mmol). Purification by flash chromatography (SiO$_2$, hexanes) afforded 4b (55 mg, 0.18 mmol, 90% yield) as a colorless oil: $^1$H NMR (400 MHz, CDCl$_3$) δ 7.52 (dd, J=7.9, 1.3 Hz, 1H), 7.26-7.21 (m, 1H), 7.18 (dd, J=7.7, 1.9 Hz, 1H), 7.05 (td, J=7.6, 1.9 Hz, 1H), 5.32 (t, J=7.2 Hz, 1H), 5.06-4.97 (m, 1H), 4.61 (d, J=2.6 Hz, 1H), 3.58 (d, J=7.2 Hz, 2H), 2.22 (t, J=6.3 Hz, 2H), 1.74-1.65 (m, 2H), 1.51-1.44 (m, 2H), 1.06 (s, 6H); $^{13}$C NMR (150 MHz, CDCl$_3$) δ C: 150.78, 146.0, 141.7, 124.7, 38.1; CH: 132.6, 129.9, 127.3, 127.3, 116.7; CH$_2$: 111.6, 41.5, 37.4, 35.3, 23.5; CH$_3$: 27.6; IR (thin-film): 2927, 1468, 1438 cm$^{-1}$; HRMS-DART (m/z) [M+H]$^+$ calculated for C$_{17}$H$_{22}$Br=305.0905, found 305.0892.

Diene 4c.

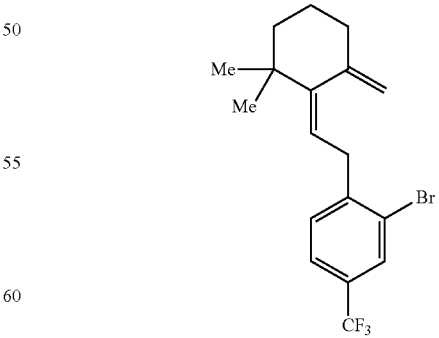

4c: C$_{18}$H$_{20}$BrF$_3$
MW: 373.26

Following the procedure for 4a, the title compound was prepared from 3b (61 mg, 0.20 mmol). Purification by flash chromatography (SiO$_2$, hexanes) afforded 4c (64 mg, 0.17 mmol, 86% yield) as a colorless oil: $^1$H NMR (400 MHz, CDCl$_3$) δ 7.81 (s, 1H), 7.50 (d, J=8.0 Hz, 1H), 7.29 (d, J=8.0 Hz, 1H), 5.30 (t, J=7.2 Hz, 1H), 5.02 (m, 1H), 4.58 (d, J=2.6 Hz, 1H), 3.62 (d, J=7.2 Hz, 2H), 2.22 (t, J=6.3 Hz, 2H), 1.76-1.63 (m, 2H), 1.52-1.44 (m, 2H), 1.06 (s, 6H); $^{13}$C NMR (150 MHz, CDCl$_3$) δ, C: 151.9, 145.9, 124.3, 123.36 (q, J=272.3 Hz), 38.2, 29.7; CH: 130.1, 129.5 (q, J=4.7, 4.1 Hz), 124.2 (q, J=3.9 Hz), 115.4; CH$_2$: 111.7, 41.5, 37.4, 35.3, 23.4; CH$_3$: 27.5; $^{19}$F NMR (376 MHz, CDCl$_3$) δ −62.5; IR (thin-film): 2929, 1607 cm$^{-1}$; HRMS-DART (m/z) [M+H]$^+$ calculated for C$_{13}$H$_{21}$F$_3$Br=373.0779, found=373.0770.

The isomers of photoprecursors 3d-3l were cyclized directly as described in Scheme 2. They were not isolated. Analytical samples of each diene were prepared by taking aliquots from the unpurified photolysate. Aliquots were filtered over a pad of silica (~100 mg, eluted with hexanes) to remove trace impurities from photodecomposition. Detailed characterization data is provided below.

Diene 4d:

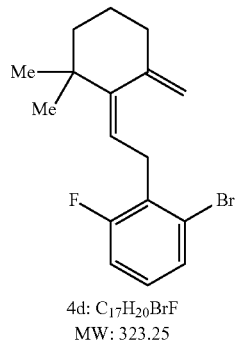

4d: C$_{17}$H$_{20}$BrF
MW: 323.25

$^1$H NMR (400 MHz, CDCl$_3$) δ 7.33 (dt, J=7.8, 1.2 Hz, 1H), 7.08-6.94 (m, 2H), 5.18-5.08 (m, 2H), 4.70 (d, J=2.7 Hz, 1H), 3.68 (dd, J=6.7, 2.2 Hz, 2H), 2.27 (t, J=6.3 Hz, 2H), 1.73-1.62 (m, 2H), 1.48-1.38 (m, 2H), 1.00 (s, 6H); $^{13}$C NMR (150 MHz, CDCl$_3$) δ C: 161.2 (d, J=248.7 Hz), 150.2, 146.4, 129.9 (d, J=18.5 Hz), 125.4 (d, J=5.2 Hz), 38.0; CH: 128.4 (d, J=3.4 Hz), 127.9 (d, J=9.1 Hz), 115.5, 114.5 (d, J=23.1 Hz); CH$_2$: 112.0, 41.4, 37.1, 29.1 (d, J=2.7 Hz), 23.5; CH$_3$: 27.4; IR (thin-film): 2927, 1455 cm$^{-1}$; HRMS-DART (m/z) [M+H]$^+$ calculated for C$_{17}$H$_{21}$BrF=323.0811, found 323.0810.

Diene 4e.

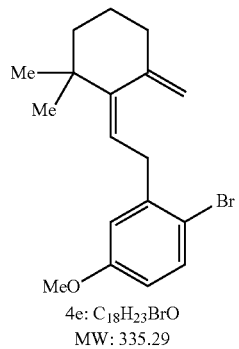

4e: C$_{18}$H$_{23}$BrO
MW: 335.29

$^1$H NMR (400 MHz, CDCl$_3$) δ 7.41 (d, J=8.7 Hz, 1H), 6.75 (d, J=3.1 Hz, 1H), 6.62 (dd, J=8.7, 3.1 Hz, 1H), 5.32 (t, J=7.2 Hz, 1H), 5.07-4.94 (m, 1H), 4.62 (d, J=2.6 Hz, 1H), 3.77 (s, 3H), 3.54 (d, J=7.3 Hz, 2H), 2.22 (t, J=6.3 Hz, 2H), 1.75-1.63 (m, 2H), 1.53-1.45 (m, 2H), 1.07 (s, 7H); $^{13}$C NMR (150 MHz, CDCl$_3$) δ C: 158.9, 151.0, 146.0, 142.7, 115.2, 38.1; CH: 133.0, 116.5, 115.8, 112.7; CH$_2$: 111.5, 41.5, 37.4, 35.4, 23.5; CH$_3$: 55.3, 27.6; IR (thin-film): 2928, 1464 cm$^{-1}$; HRMS-DART (m/z) [M+H]$^+$ calculated for C$_{13}$H$_{24}$BrO=335.1010, found 335.1005.

Diene 4f:

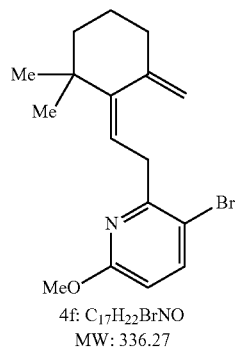

4f: C$_{17}$H$_{22}$BrNO
MW: 336.27

$^1$H NMR (400 MHz, CDCl$_3$) δ 7.60 (d, J=8.6 Hz, 1H), 6.46 (d, J=8.5 Hz, 1H), 5.47 (t, J=7.0 Hz, 1H), 5.08-5.01 (m, 1H), 4.77 (d, J=2.8 Hz, 1H), 3.90 (s, 3H), 3.70 (d, J=7.0 Hz, 2H), 2.23 (t, J=6.3 Hz, 2H), 1.74-1.63 (m, 2H), 1.50-1.42 (m, 2H), 1.05 (s, 6H); $^{13}$C NMR (150 MHz, CDCl$_3$) δ C: 162.4, 157.1, 150.1, 146.2, 111.8, 38.0; CH: 142.3, 115.7, 109.5; CH$_2$: 111.5, 41.5, 37.3, 36.7, 23.5; CH$_3$: 53.5, 27.5; IR (thin-film): 2927, 1457 cm$^{-1}$; HRMS-DART (m/z) [M+H]$^+$ calculated for C$_{17}$H$_{23}$BrNO=336.0963, found 336.0971.

Diene 4g:

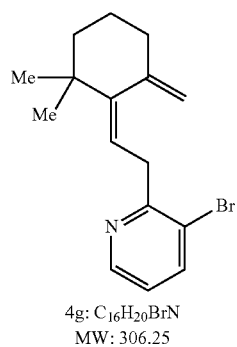

4g: C$_{16}$H$_{20}$BrN
MW: 306.25

$^1$H NMR (400 MHz, CDCl$_3$) δ 8.47 (dd, J=4.7, 1.6 Hz, 1H), 7.79 (dd, J=8.0, 1.6 Hz, 1H), 7.00 (dd, J=8.0, 4.7 Hz, 1H), 5.40 (t, J=6.7 Hz, 1H), 5.13-5.04 (m, 1H), 4.73 (d, J=2.7 Hz, 1H), 3.84 (d, J=6.7 Hz, 2H), 2.25 (t, J=6.3 Hz, 2H), 1.73-1.62 (m, 3H), 1.49-1.40 (m, 2H), 1.03 (s, 6H); $^{13}$C NMR (100 MHz, CDCl$_3$) δ C: 160.2, 150.4, 146.2, 121.3, 38.1, CH: 147.9, 140.2, 122.3, 115.4, CH$_2$: 112.0, 41.4, 37.7, 37.2, 23.4, CH$_2$: 27.5; IR (thin film): 3046, 2926, 1573, 1422 cm$^{-1}$; HRMS-DART (m/z) [M+H]$^+$ calculated for C$_{16}$H$_{21}$BrN=307.0857, found=307.0860.

Diene 4h:

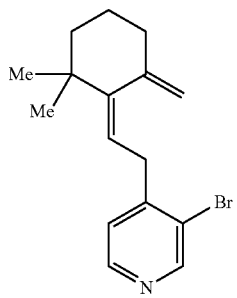

4h: C₁₆H₂₀BrN
MW: 306.25

¹H NMR (400 MHz, CDCl₃) δ 8.63 (s, 1H), 8.40 (d, J=5.0 Hz, 1H), 7.12 (d, J=4.9 Hz, 1H), 5.28 (t, J=7.3 Hz, 1H), 5.01 (dt, J=2.8, 1.4 Hz, 1H), 4.57 (d, J=2.5 Hz, 1H), 3.57 (d, J=7.3 Hz, 2H), 2.21 (t, J=6.3 Hz, 2H), 1.74-1.63 (m, 2H), 1.52-1.44 (m, 2H), 1.07 (s, 6H); ¹³C NMR (150 MHz, CDCl₃) δ C: 152.7, 150.8, 147.7, 145.8, 38.3; CH: 151.5, 148.1, 124.7, 111.8; CH₂: 114.2, 41.5, 37.4, 34.6, 23.4; CH₃: 27.5; IR (thin-film): 2928, 2866, 1580, 1459 cm⁻¹; HRMS-DART (m/z) [M+H]⁺ calculated for C₁₆H₂₁BrN=306.0857, found=306.0842.

Diene 4i.

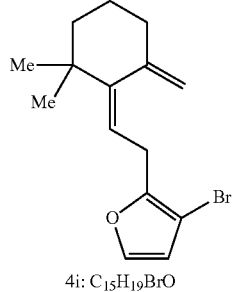

4i: C₁₅H₁₉BrO
MW: 295.22

¹H NMR: (400 MHz, CDCl₃) δ 7.27 (s, 1H), 6.34 (d, J=2.0 Hz, 1H), 5.27 (t, J=7.1 Hz, 1H), 5.10-5.02 (m, 1H), 4.70 (d, J=2.6 Hz, 1H), 3.51 (d, J=7.1 Hz, 2H), 2.21 (t, J=6.4 Hz, 2H), 1.73-1.61 (m, 2H), 1.50-1.39 (m, 2H), 1.03 (s, 6H); ¹³C NMR: (150 MHz, CDCl₃) δ 152.3, 151.1, 145.8, 141.1, 113.7, 113.6, 112.1, 95.5, 41.5, 38.1, 37.3, 27.3, 26.2, 23.5; IR (thin-film): 3367, 2926, 729 cm⁻¹; HRMS-DART (m/z) [M+H]⁺ calculated for C₁₅H₂₀BrO=296.0697, found 296.0643.

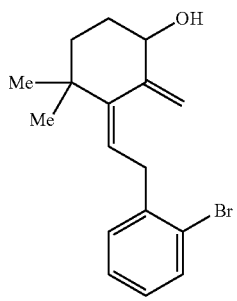

4j: C₁₇H₂₁BrO
MW: 321.26

¹H NMR (400 MHz, CDCl₃) δ 7.53 (dd, J=7.9, 1.3 Hz, 1H), 7.25-7.21 (m, 1H), 7.18 (dd, J=7.7, 1.9 Hz, 1H), 7.05 (td, J=7.6, 1.9 Hz, 1H), 5.47 (t, J=7.2 Hz, 1H), 5.31 (t, J=1.8 Hz, 1H), 4.81 (t, J=1.6 Hz, 1H), 4.15 (dd, J=8.3, 4.5 Hz, 1H), 3.67-3.47 (m, 2H), 2.02-1.92 (m, 1H), 1.73-1.60 (m, 2H), 1.48-1.36 (m, 1H), 1.08 (s, 3H), 1.07 (s, 3H); ¹³C NMR (150 MHz, CDCl₃) δ C: 148.2, 147.8, 141.2, 124.6, 37.8; CH: 132.7, 129.9, 127.5, 127.4, 119.7, 73.6; CH₂: 110.5, 37.3, 35.1, 31.7; CH₃: 27.4, 27.1; IR: 3329, 2933, 1465 cm⁻¹; HRMS-ESI (m/z) [M+Na]⁺ calculated for C₁₇H₂₁BrONa=343.0673, found 343.0680.

Diene 4k.

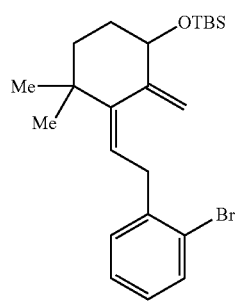

4k: C₂₃H₃₅BrOSi
MW: 435.52

¹H NMR (400 MHz, CDCl₃) δ 7.53 (dd, J=8.0, 1.3 Hz, 1H), 7.26-7.21 (m, 1H), 7.17 (dd, J=7.7, 1.9 Hz, 1H), 7.05 (td, J=7.6, 1.9 Hz, 1H), 5.39 (dd, J=7.9, 6.4 Hz, 1H), 5.34 (t, J=2.3 Hz, 1H), 4.74 (t, J=2.3 Hz, 1H), 4.09-4.00 (m, 1H), 3.62 (dd, J=16.0, 7.9 Hz, 1H), 3.49 (dd, J=16.0, 6.5 Hz, 1H), 1.91-1.81 (m, 1H), 1.74-1.62 (m, 1H), 1.57 (dt, J=13.4, 4.3 Hz, 1H), 1.43 (dd, J=12.6, 4.3 Hz, 1H), 1.08 (s, 3H), 1.03 (s, 3H), 0.93 (s, 9H), 0.09 (s, 3H), 0.08 (s, 3H); ¹³C NMR (150 MHz, CDCl₃) δ C: 149.2, 148.1, 141.5, 124.70, 118.4, 37.7, 18.4, CH: 132.6, 129.9, 127.4, 127.3, 74.3, CH₂: 109.8, 38.1, 35.3, 33.0, CH₃: 27.8, 26.7, 25.9, −4.8, −5.0; IR (thin film): 745, 1463, 2928 cm¹; HRMS-ESI (m/z) [M+Na]⁺ calculated for C₂₃H₃₄BrOSiNa=457.1538, found 457.1536.

III. Direct Cyclization of Photosubstrates 3 [in Scheme 2]

[4.4.1]-Propellane 5a. OMe

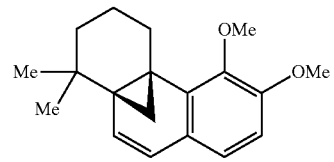

5a: C₁₉H₂₄O₂
MW: 284.40

Multi-gram preparation: This procedure used dioxane prepared by distillation from a benzophenone ketyl still.[13] A round-bottom flask charged with (E)-3a (14.612 g, 40.000 mmol) was connected to a hi-vac line. The flask was placed under nitrogen (N₂) by evacuating (~1.00 mBar) and backfilling with N₂. This process was repeated 3 times. The flask was then fitted with a rubber septa, placed under a balloon of N₂, and dioxane (200 mL) was added via syringe. The FEP-tubing spindle (max volume=250 mL) shown in FIG. S1 was fitted with a 9-inch steel needle on the bottom end and left open on the top end. Using a positive pressure of N₂, tubing reactor was charged with the solution (E)-3a using cannula technique. Care was taken to leave at least 2 inches of room at the top and bottom of the reactor, such that the solution occupied the center of the tubing spindle. The spindle was capped at each end with a disposable 3 mL syringe and then transferred to a Rayonet chamber photoreactor that was preheated to 35° C. The spindle was exposed to 300 nm UV-light. After 3 h, spindle was removed from the photoreactor, cooled to r.t. and the bottom end was fitted with a 9-inch steel needle. A 2-neck flask equipped with a reflux condenser was charged with $Pd_2dba_3$ (1.10 g, 1.20 mmol,) and $(t-Bu)_3P \cdot HBF_4$ (696 mg, 2.40 mmol) and placed under a balloon of $N_2$. The unpurified photolysate from the tubing spindle was added under a positive pressure. The resulting solution was treated with $Cy_2NMe$ (10.3 mL, 48.0 mmol) and then heated to 85° C. After 1 h, the reaction mixture was cooled to r.t. and concentrated under reduced pressure. The resulting residue was digested with EtOAc (100 mL) and filtered over Celite and the filter cake was washed with EtOAc (2×50 mL). The combined organic extracts were washed with 1 M aq. HCl (2×150 mL), saturated aq. $NaHCO_3$ (2×150 mL), and brine (150 mL). The organic layer was dried over $MgSO_4$, filtered, and concentrated under reduced pressure. The resulting crude residue was purified by flash chromatography ($SiO_2$, 20:1 hexanes/EtOAc) to afford 5a (8.646 g, 30.400 mmol, 76% yield) as a colorless solid: mp=78-82° C.; $^1H$ NMR (400 MHz, $CDCl_3$) δ 6.74 (d, J=8.3 Hz, 1H), 6.70 (d, J=8.3 Hz, 1H), 6.15 (d, J=10.0 Hz, 1H), 6.10 (d, J=10.0 Hz, 1H), 3.85 (s, 3H), 3.82 (s, 3H), 2.56-2.41 (m, 1H), 2.41-2.26 (m, 1H), 1.49-1.39 (m, 1H), 1.39-1.29 (m, 1H), 1.22 (d, J=4.0 Hz, 1H), 1.17 (s, 3H), 1.16-1.12 (m, 2H), 1.07 (s, 3H), 0.17 (d, J=3.9 Hz, 1H); $^{13}C$ NMR (150 MHz, $CDCl_3$) δ C: 152.6, 148.5, 135.9, 124.9, 35.1, 31.2, 25.7; CH: 129.6, 123.0, 122.7, 109.5; $CH_2$: 35.5, 31.1, 18.7, 17.2 $CH_3$: 60.3, 56.2, 29.0, 26.4; IR (thin-film): 2927, 1484 $cm^{-1}$; HRMS-DART (m/z) $[M+H]^+$ calculated for $C_{19}H_{25}O_2$=285.1854, found 285.1858. The structure of 5a was confirmed by single crystal X-ray diffraction (CCDC 2129320).

B. Preparation of other [4.4.1]-propellanes 5.

[4.4.1]-Propellane 5b.

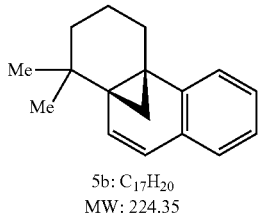 [SMILES: CC1(C)CCC[C@@]23C[C@@]12C=Cc1ccccc13]

5b: $C_{17}H_{20}$
MW: 224.35

General Procedure: A 1-dram borosilicate vial was charged with a solution of 3b (61 mg, 0.20 mmol) in oxygen-free dioxane (1.0 mL) and capped under a positive pressure of nitrogen. The vial was transferred to a Rayonet chamber photoreactor preheated to 35° C. and exposed to 300 nm UV-light until the reaction was judged to be complete by $^1H$ NMR spectroscopy. After 5 h, reaction was removed from the photoreactor and the unpurified photolysate was added via syringe to a stirred solution of $Pd_2dba_3$ (5.5 mg, 0.0060 mmol), $(t-Bu)_3P \cdot HBF_4$ (3.5 mg, 0.012 mmol) and $Cy_2NMe$ (0.05 mL, 0.24 mmol) in dioxane (0.5 mL). The resulting solution was heated to 85° C. After 1 h, the reaction mixture was cooled to r.t. and diluted with EtOAc (5 mL). The resulting slurry was filtered over Celite® and the filter cake was washed with EtOAc (2×5 mL). The combined organic extracts were washed with 1 M aq. HCl (2×15 mL), saturated aq. $NaHCO_3$ (2×15 mL), and brine (15 mL). The organic layer was then dried over $MgSO_4$, filtered, and concentrated under reduced pressure. The resulting crude residue was purified by flash chromatography ($SiO_2$, hexanes) to afford 5b (32.8 mg, 0.146, 73% yield) as a colorless oil: $^1H$ NMR (400 MHz, $CDCl_3$) δ 7.49 (d, J=7.8 Hz, 1H), 7.21 (td, J=7.4, 1.8 Hz, 1H), 7.12 (td, J=7.3, 1.2 Hz, 1H), 7.08 (dd, J=7.5, 1.8 Hz, 1H), 6.35 (d, J=9.9 Hz, 1H), 6.28 (d, J=9.9 Hz, 1H), 2.44 (ddd, J=13.6, 7.2, 3.5 Hz, 1H), 2.30 (ddd, J=13.6, 10.3, 7.2 Hz, 1H), 1.53-1.36 (m, 3H), 1.30-1.23 (m, 1H), 1.22 (s, 3H), 1.16 (dt, J=13.7, 4.5 Hz, 1H), 1.06 (s, 3H), −0.05 (d, J=3.8 Hz, 1H); $^{13}C$ NMR (150 MHz, $CDCl_3$) b C: 141.2, 130.2, 37.1, 31.0, 28.4; CH: 132.1, 127.3, 126.6, 125.6, 124.9, 122.6; $CH_2$: 35.6, 29.1, 19.9, 17.8; $CH_3$: 28.78, 26.75; IR (thin-film): 3033, 2934, 1450 $cm^{-1}$; HRMS-DART (m/z) $[M+H]^+$ calculated for $C_{17}H_{21}$=225.1643, found 225.1650.

Carbocycles 5c-5k were prepared from the corresponding photoprecursors 3 on 0.20 mmol scale using the general procedure described for 5b. The only changes were differences in purification conditions as noted below:

[4.4.1]-Propellane 5c.

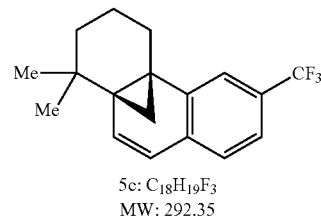 [SMILES: CC1(C)CCC[C@@]23C[C@@]12C=Cc1ccc(C(F)(F)F)cc13]

5c: $C_{18}H_{19}F_3$
MW: 292.35

Following the general procedure, purification by flash chromatography ($SiO_2$, 97:3 hexanes/EtOAc) afforded 5c (43.9 mg, 0.150 mmol, 75% yield) as a colorless solid: mp=63-64° C.; $^1H$ NMR (400 MHz, $CDCl_3$) δ 7.71 (s, 1H), 7.35 (d, J=8.0, 1.8 Hz, 1H), 7.15 (d, J=7.9 Hz, 1H), 6.49 (d, J=9.9 Hz, 1H), 6.31 (d, J=9.9 Hz, 1H), 2.45-2.29 (m, 2H), 1.51 (d, J=4.1 Hz, 1H), 1.49-1.39 (m, 2H), 1.31-1.24 (m, 1H), 1.23 (s, 3H), 1.17 (dt, J=13.7, 4.6 Hz, 1H), 1.05 (s, 3H), −0.06 (d, J=4.0 Hz, 1H); $^{13}C$ NMR (150 MHz, $CDCl_3$) δ C: 141.6, 133.3, 128.3 (q, J=32.0 Hz), 124.6 (q, J=272.1 Hz), 37.6, 31.0, 28.6; CH: 135.0, 127.3, 122.6 (q, J=3.9 Hz), 121.8, 121.7 (q, J=4.0 Hz); $CH_2$: 35.5, 29.1, 20.1, 17.6; $CH_3$: 28.7, 26.7; $^{19}F$ NMR (376 MHz, $CDCl_3$) δ −62.1; IR (thin-film): 2921, 1402, 894 $cm^{-1}$; HRMS-DART (m/z) $[M+H]^+$ calculated for $C_{18}H_{20}F_3$=293.1517, found=293.1504.

[4.4.1]-Propellane 5d.

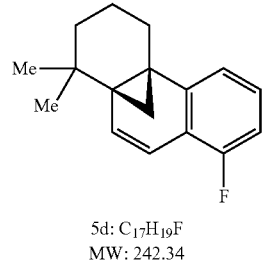 [SMILES: CC1(C)CCC[C@@]23C[C@@]12C=Cc1c(F)cccc13]

5d: $C_{17}H_{19}F$
MW: 242.34

Following the general procedure, purification by flash chromatography (SiO$_2$, 97:3 hexanes) afforded 5d (33.9 mg, 0.140 mmol, 70% yield) as a colorless oil: $^1$H NMR (400 MHz, CDCl$_3$) δ 7.26 (d, J=7.8 Hz, 1H), 7.18-7.10 (m, 1H), 6.84 (t, J=9.1 Hz, 1H), 6.58 (d, J=10.1 Hz, 1H), 6.43 (d, J=10.1 Hz, 1H), 2.45-2.35 (m, 1H), 2.35-2.24 (m, 1H), 1.59-1.48 (m, 1H), 1.46 (d, J=4.0 Hz, 1H), 1.45-1.36 (m, 1H), 1.30-1.24 (m, 1H), 1.22 (s, 3H), 1.16 (dt, J=13.6, 4.5 Hz, 1H), 1.06 (s, 3H), −0.05 (d, J=4.0 Hz, 1H); $^{13}$C NMR (150 MHz, CDCl$_3$) δ C: 158.9 (d, J=247.2 Hz), 143.4 (d, J=4.2 Hz), 118.4 (d, J=14.0 Hz), 37.3, 31.0, 28.5 (d, J=2.4 Hz); CH: 132.8 (d, J=2.8 Hz), 126.8 (d, J=8.9 Hz), 121.2 (d, J=2.9 Hz), 113.6 (d, J=7.1 Hz), 111.2 (d, J=21.6 Hz); CH$_2$: 35.5, 29.2, 20.2, 17.7; CH$_3$: 28.8, 26.7; IR (thin-film): 2933, 1460 cm$^{-1}$; HRMS-DART (m/z) [M+H]$^+$ calculated for C$_{17}$H$_{20}$BrF=243.1549, found 243.1550.

[4.4.1]-Propellane 5e.

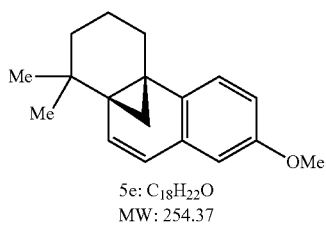 [SMILES: COc1ccc2c(c1)C=C[C@@]13C[C@@]21CCCC3(C)C]

5e: C$_{18}$H$_{22}$O
MW: 254.37

Following the general procedure, purification by flash chromatography (SiO$_2$, 99:1 hexanes/Et$_2$O) afforded 5e (32.1 mg, 0.126 mmol, 63% yield) as a colorless oil: $^1$H NMR (400 MHz, CDCl$_3$) δ 7.38 (d, J=8.5 Hz, 1H), 6.79 (dd, J=8.6, 2.8 Hz, 1H), 6.63 (d, J=2.8 Hz, 1H), 6.37 (d, J=9.9 Hz, 1H), 6.23 (d, J=10.0 Hz, 1H), 3.80 (s, 3H), 2.43-2.34 (m, 1H), 2.34-2.22 (m, 1H), 1.52-1.38 (m, 2H), 1.35 (d, J=3.9 Hz, 1H), 1.29-1.22 (m, 1H), 1.20 (s, 3H), 1.15 (dt, J=13.6, 4.5 Hz, 1H), 1.05 (s, 3H), −0.09 (d, J=3.8 Hz, 1H); $^{13}$C NMR (150 MHz, CDCl$_3$) δ C: 157.1, 133.8, 131.3, 36.6, 30.9, 27.9; CH: 133.1, 126.5, 122.6, 112.6, 112.1; CH$_2$: 35.7, 29.3, 20.0, 17.7; CH$_3$: 55.3, 28.7, 26.8; IR (thin-film): 2932, 1493, 1463 cm$^{-1}$; HRMS-DART (m/z) [M+H]$^+$ calculated for C$_{18}$H$_{23}$O=255.1749, found 255.1754.

[4.4.1]-Propellane 5f.

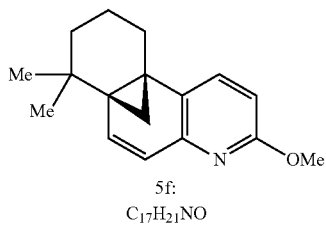

5f:
C$_{17}$H$_{21}$NO
MW: 255.36

Following the general procedure, purification by flash chromatography (SiO$_2$, 97:3 hexanes/EtOAc) afforded 5f (37.8 mg, 0.148 mmol, 74% yield) as a yellow oil: $^1$H NMR (400 MHz, CDCl$_3$) δ 7.66 (d, J=8.5 Hz, 1H), 6.62 (d, J=10.1 Hz, 1H), 6.58 (d, J=8.5 Hz, 1H), 6.39 (d, J=10.1 Hz, 1H), 3.91 (s, 3H), 2.27 (dd, J=8.7, 5.4 Hz, 2H), 1.51-1.35 (m, 3H), 1.22 (s, 3H), 1.21-1.12 (m, 2H), 1.05 (s, 3H), −0.12 (d, J=3.9 Hz, 1H); $^{13}$C NMR (150 MHz, CDCl$_3$) δ C: 161.4, 146.4, 129.2, 37.0, 30.9, 27.8; CH: 137.2, 136.1, 124.2, 107.9; CH$_2$: 35.7, 29.2, 19.6, 17.6; CH$_3$: 53.2, 28.7, 26.8; IR (thin-film): 2947, 1471, 1440 cm$^{-1}$; HRMS-DART (m/z) [M+H]$^+$ calculated for C$_{17}$H$_{22}$NO=256.1701, found 256.1710.

[4.4.1]-Propellane 5g.

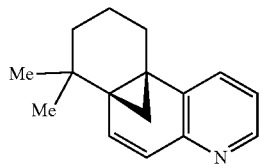

5g: C$_{16}$H$_{19}$N
MW: 225.15

Following the general procedure, purification by flash chromatography (SiO$_2$, 4:1 hexanes/EtOAc) afforded 5g (35.6 mg, 0.158 mmol, 79% yield) as a yellow oil: $^1$H NMR (400 MHz, CDCl$_3$) δ 8.34 (dd, J=4.8, 1.6 Hz, 1H), 7.73 (dd, J=7.8, 1.6 Hz, 1H), 7.09 (dd, J=7.8, 4.8 Hz, 1H), 6.66 (d, J=10.2 Hz, 1H), 6.50 (d, J=10.1 Hz, 1H), 2.36-2.27 (m, 2H), 1.54-1.39 (m, 3H), 1.29-1.13 (m, 6H), 1.06 (s, 3H), −0.03 (d, J=4.0 Hz, 1H); $^{13}$C NMR (100 MHz, CDCl$_3$) δ C: 149.2, 136.6, 37.3, 31.0, 28.0, CH: 145.8, 137.5, 133.0, 124.5, 121.2, CH$_2$: 35.5, 28.8, 20.3, 17.6, CH$_3$: 28.7, 26.7; IR (thin film): 3043, 2930, 1560, 1445 cm$^{-1}$; HRMS-DART (m/z) [M+H]$^+$ calculated for C$_{16}$H$_{20}$N=226.1596, found=226.1598.

[4.4.1]-Propellane 5h.

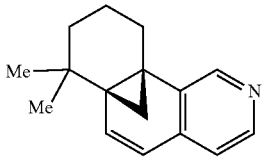

5h: C$_{16}$H$_{19}$N
MW: 225.15

Following the general procedure, purification by flash chromatography (SiO$_2$, 4:1 hexanes/EtOAc) afforded 5h (27.0 mg, 0.120 mmol, 60% yield) as a yellow oil: $^1$H NMR (600 MHz, CDCl$_3$) δ 8.69 (s, 1H), 8.33 (d, J=5.0 Hz, 1H), 6.93 (d, J=4.9 Hz, 1H), 6.62 (d, J=9.9 Hz, 1H), 6.24 (d, J=9.9 Hz, 1H), 2.48-2.41 (m, 1H), 2.41-2.34 (m, 1H), 1.54 (d, J=4.1 Hz, 1H), 1.52-1.39 (m, 2H), 1.29-1.23 (m, 1H), 1.22 (s, 3H), 1.20-1.14 (m, 1H), 1.05 (s, 3H), −0.10 (dd, J=4.2, 1.0 Hz, 1H); $^{13}$C NMR (150 MHz, CDCl$_3$) δ C: 135.6, 120.7, 37.6, 31.0, 27.2; CH: 147.4, 146.2, 138.1, 136.5, 120.8 CH$_2$: 35.5, 28.9, 19.9, 17.5, CH$_3$: 28.8, 26.8; IR (thin film): 3039, 2932, 1587, 1492 cm$^{-1}$; HRMS-DART (m/z) [M+H]$^+$ calculated for C$_{16}$H$_{20}$N=226.1596, found=226.1590.

[4.4.1]-Propellane 5i.

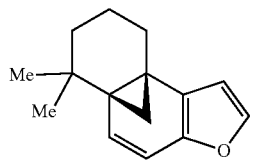

5i: C$_{15}$H$_{18}$O
MW: 214.31

Following the general procedure, purification by flash chromatography (SiO$_2$, hexanes) afforded 5i (20.1 mg, 0.094 mmol, 47% yield) as a colorless oil: $^1$H NMR (400 MHz, CDCl$_3$) δ 7.27 (d, J=1.9 Hz, 1H), 6.46 (d, J=1.5 Hz, 1H), 6.34 (d, J=10.2 Hz, 1H), 6.14 (d, J=10.2 Hz, 1H), 2.30-2.19 (m, 1H), 2.16-2.03 (m, 1H), 1.44 (d, J=4.4 Hz, 1H), 1.37-1.31 (m, 2H), 1.23 (s, 3H), 1.18-1.13 (m, 2H), 0.99 (s, 3H), −0.23 (d, J=4.3 Hz, 1H); $^{13}$C NMR (100 MHz, CDCl$_3$) δ C: 146.8, 124.8, 39.3, 31.3, 28.4; CH: 140.4, 129.1, 112.3, 109.0; CH$_2$: 36.0, 29.3, 18.7, 17.8; CH$_3$: 26.6; IR (thin-film): 2926, 729 cm$^{-1}$; HRMS-DART (m/z) [M+H]$^+$ calculated for C$_{15}$H$_{19}$O=215.1436, found 215.1441.

[4.4.1]-Propellane 5j.

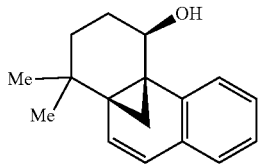

5j (major): C$_{17}$H$_{20}$O
MW: 240.35

Following the general procedure, purification by flash chromatography (SiO$_2$, 9:1 hexanes/EtOAc) afforded 5j (20.1 mg, 0.122 mmol, 61% yield, 2:1 d.r.) as a colorless foam: $^1$H NMR (400 MHz, CDCl$_3$) δ 7.70 (d, J=7.8 Hz, 1H), 7.25 (td, J=7.6, 1.6 Hz, 1H), 7.16 (td, J=7.4, 1.2 Hz, 1H), 7.10 (dd, J=7.5, 1.6 Hz, 1H), 6.33 (d, J=10.2 Hz, 1H), 6.30 (d, J=9.9 Hz, 1H), 4.79 (dd, J=5.6, 1.7 Hz, 1H), 1.75 (d, J=4.4 Hz, 1H), 1.74-1.66 (m, 1H), 1.53-1.38 (m, 2H), 1.25 (s, 4H), 1.09 (dt, J=13.9, 3.9 Hz, 1H), 1.01 (s, 3H), −0.12 (d, J=4.2 Hz, 1H); $^{13}$C NMR (150 MHz, CDCl$_3$) δ C: 139.1, 129.9, 38.6, 35.6, 30.9; CH: 130.3, 127.6, 127.2, 125.6, 125.5, 123.3, 69.2; CH$_2$: 30.7, 28.0, 14.2; CH$_3$: 28.6, 25.9. IR (thin-film): 3384, 2957, 1490, 1453 cm$^{-1}$; HRMS-ESI (m/z) [M+H]$^+$ calculated for C$_{17}$H$_{21}$O=241.1592, found 241.1601.

Minor Diastereomer 5j.

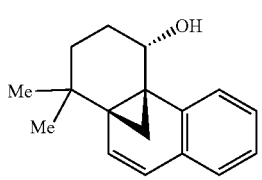

5j (minor): C$_{17}$H$_{20}$O
MW: 240.35

An analytical sample was prepared by pTLC (10:1 hexanes/EtOAc): $^1$H NMR (400 MHz, CDCl$_3$) δ 7.63 (d, J=7.7 Hz, 1H), 7.31-7.22 (m, 1H), 7.22-7.10 (m, 2H), 6.38 (d, J=10.0 Hz, 1H), 6.26 (d, J=10.0 Hz, 1H), 5.01 (t, J=3.7 Hz, 1H), 1.92 (s, 1H), 1.76-1.69 (m, 2H), 1.64-1.55 (m, 2H), 1.51 (d, J=4.7 Hz, 1H), 1.19 (s, 3H), 1.17 (s, 3H), −0.04 (d, J=4.7 Hz, 1H); $^{13}$C NMR (150 MHz, CDCl$_3$) δ C: 135.7, 131.6, 35.6, 33.8, 31.0; CH: 131.8, 128.3, 127.0, 125.7, 125.1, 122.1, 65.0; CH$_2$: 31.6, 25.2, 17.5; CH$_3$: 29.8, 28.7. HRMS-ESI (m/z) [M+H]$^+$ calculated for C$_{17}$H$_{21}$O=241.1592, found 241.1598.

[4.4.1]-Propellane 5k.

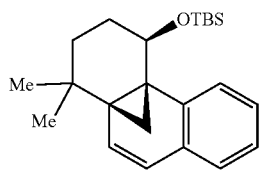

5k: C$_{23}$H$_{34}$OSi
MW: 354.61

Following the general procedure, purification by flash chromatography (SiO$_2$, hexanes) afforded 5k (53.2 mg, 0.150 mmol, 75% yield, >25:1 d.r.) as a colorless oil: $^1$H NMR (400 MHz, CDCl$_3$) δ 7.61 (d, J=7.8 Hz, 1H), 7.22 (td, J=7.4, 1.7 Hz, 1H), 7.16-7.05 (m, 2H), 6.30 (s, 2H), 4.86-4.79 (m, 1H), 1.90 (d, J=4.4 Hz, 1H), 1.65-1.55 (m, 1H), 1.50-1.36 (m, 2H), 1.24 (s, 3H), 1.04-0.98 (m, 4H), 0.95 (s, 9H), 0.25 (s, 3H), 0.17 (s, 3H), −0.18 (d, J=4.3 Hz, 1H); $^{13}$C NMR (150 MHz, CDCl$_3$) δ C: 140.1, 130.1, 38.1, 35.8, 31.2, 18.2; CH: 131.2, 127.4, 126.5, 125.5, 124.9, 122.8, 69.9; CH$_2$: 30.1, 28.9, 15.0; CH$_3$: 26.2, 25.9, −3.35, −4.24; IR: 2929, 1471 cm$^{-1}$; HRMS-ESI (m/z) [M+Na]$^+$ calculated for C$_{23}$H$_{34}$OSiNa=377.2277, found 377.2273.

The relative stereochemistry of 5j and 5k was established as follows (Scheme S1): 5k (>20:1 d.r.) was deprotected with TBAF. The product of this reaction was identical to major diastereomer 3h described above. This intermediate was protected with BzCl to afford S5. The relative stereochemistry (cis) of this derivative was established by single crystal X-ray diffraction.

Scheme 1. The relative stereochemistry of 5j and 5k was confirmed by X-ray cystallography.

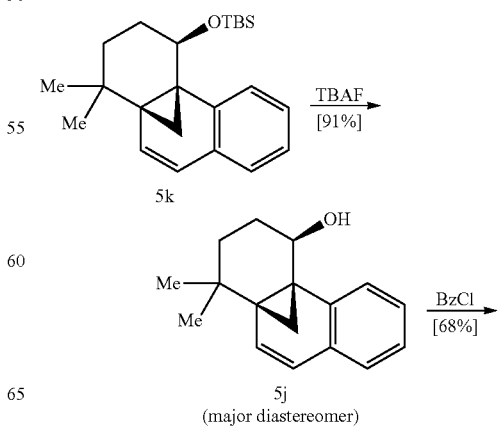

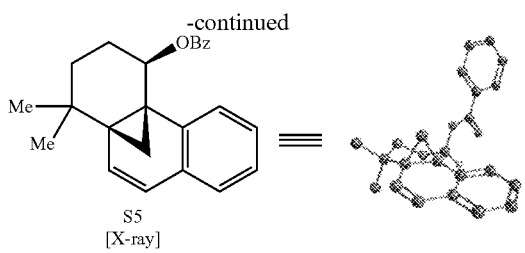

Derivative S5.

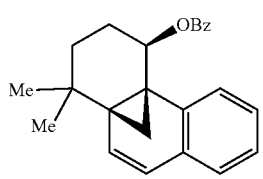

S5: C$_{24}$H$_{24}$O$_2$
MW: 344.45

Triethylamine (0.08 mL, 0.58 mmol) was added dropwise to a solution of 5j (100 mg, 0.420 mmol) and DMAP (15 mg, 0.13 mmol) in PhMe (2.0 mL). The reaction mixture was heated to 100° C. After 9 h, the reaction was cooled to r.t. and diluted with CH$_2$Cl$_2$ (10 mL). The organic solution was washed with 1 M aq. HCl (5 mL), saturated aq. NaHCO$_3$ (5 mL), and brine (5 mL). The organic layer was collected, dried over MgSO$_4$, filtered, and concentrated under reduced pressure. The resulting crude residue was purified by flash chromatography (SiO$_2$, 97:3 hexanes/EtOAc) to afford S5 (98 mg, 0.28 mmol, 68% yield) as a colorless solid: mp=100-105° C.; $^1$H NMR (500 MHz, CDCl$_3$) δ 8.20-8.12 (d, J=7.6 Hz, 2H), 7.59 (t, J=7.4 Hz, 1H), 7.52-7.43 (m, 3H), 7.19 (t, J=7.4, 1H), 7.17-7.08 (m, 2H), 6.36 (s, 2H), 6.23 (d, J=5.3 Hz, 1H), 4.45 Hz, 1H), 1.88 (tdd, J=15.1, 5.5, 3.5 Hz, 1H), 2.16 (d, J=4.5 Hz, 1H), 1.88 (tdd, J=15.1, 5.5, 3.5 Hz, 1H), 1.74-1.64 (m, 1H), 1.51 (t, J=14.3 Hz, 1H), 1.32 (s, 3H), 1.15 (dt, J=14.1, 3.7 Hz, 1H), 1.08 (s, 3H), 0.13 (d, J=4.5 Hz, 1H); $^{13}$C NMR (125 MHz, CDCl$_3$) δ C: 165.9, 138.5, 130.9, 129.8, 37.7, 32.2, 31.0; CH: 133.0, 130.2, 129.7, 128.4, 127.7, 127.4, 125.6, 125.5, 123.5, 73.5; CH$_2$: 30.6, 25.6, 15.8; CH$_3$: 28.8, 25.8; IR (thin-film): 2950, 1696, 1449 cm$^{-1}$; HRMS-DART (m/z) [M+H]$^+$ calculated for C$_{24}$H$_{25}$O$_2$=345.1854, found 345.1858. Crystals suitable for X-ray diffraction were prepared by slow evaporation from CH$_2$Cl$_2$/hexanes (CCDC 2130343).

IV. Total Synthesis of Taxodione and Salviasperanol [in Scheme 3 and Scheme 4]

Benzyl Alcohol S6.

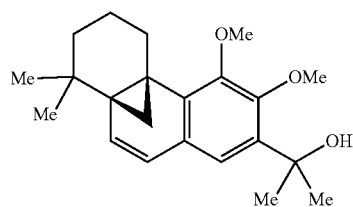

S6: C$_{22}$H$_{30}$O$_3$
MW: 342.48

Freshly distilled TMEDA (5.0 mL, 33 mmol) was added dropwise to a solution of 5a (3.16 g, 11.1 mmol) in THF (65 mL). The resulting solution was cooled to −78° C. and treated with n-BuLi (2.1 M in THF, 15.9 mL, 33.4 mmol). The reaction mixture was maintained at −78° C. for 0.5 h, then warmed to r.t. with a water bath during which time the reaction turned dark red. After 2 h, the reaction was cooled to 0° C. and freshly distilled acetone (4.1 mL, 56 mmol) was added dropwise via syringe. After 3 h, the reaction was treated with 1 M aq. citric acid (35 mL) and allowed to warm to r.t. over 1 h. The resulting slurry was transferred to a separatory funnel and extracted with EtOAc (3×25 mL). The combined organic extracts were then washed saturated aq. NaHCO$_3$ (2×50 mL) and brine (50 mL), collected, dried over MgSO$_4$, filtered, and concentrated under reduced pressure. The resulting crude residue was purified by flash chromatography (SiO$_2$, 40:1→15:1 hexanes/EtOAc) to afford recovered 5a (252 mg, 0.888 mmol, 8% yield) and S6 (3.42 g, 9.99 mmol, 90% yield) as a yellow oil: $^1$H NMR (600 MHz, CDCl$_3$) δ 6.74 (s, 1H), 6.16 (dd, J=9.7, 5.1 Hz, 2H), 4.27 (s, 1H) 4.04 (s, 3H), 3.79 (s, 3H), 2.47 (m, 1H), 2.32 (m, 1H), 1.58 (d, J=6.6 Hz, 6H), 1.48-1.30 (m, 2H), 1.25 (d, J=3.9 Hz, 1H), 1.17 (m, 5H), 1.06 (s, 3H), 0.13 (d, J=3.9 Hz, 1H); $^{13}$C NMR (175 MHz, CDCl$_3$) δ C: 152.5, 150.6, 138.1, 135.1, 126.7, 72.4, 35.3, 31.2, 25.9; CH: 131.1, 122.79, 120.0; CH$_2$: 35.5, 31.3, 18.6, 17.1; CH$_3$: 61.2, 59.9, 31.5, 29.9, 28.8, 26.3; IR (thin-film): 3452, 2868, 1380 cm$^{-1}$; HRMS-DART (m/z) [M+H]$^+$ calculated for C$_{22}$H$_{31}$O$_3$=343.2273; found 343.2270.

Overbred Abietane 10.

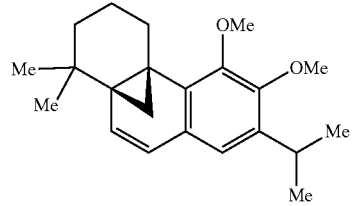

10: C$_{22}$H$_{30}$O$_2$
MW: 326.22

A solution of S6 (2.40 g, 7.00 mmol) in CH$_2$Cl$_2$ (10 mL) was cooled to −78° C. a treated with MeLi (2.1 M in hexanes, 3.5 mL, 7.4 mmol). After 15 min, the reaction mixture was warmed to 0° C. and maintained for 0.5 h before chloroborane methyl sulfide complex (1.6 mL, 15 mmol) was added dropwise via syringe. After 2 h, the reaction was warmed to r.t. and diluted with EtOAc (50 mL). The organic solution was transferred to a separatory funnel and washed with saturated NaHCO (50 mL). The aqueous layer was then extracted with EtOAc (3×25 mL). The combined organic extracts were washed with brine (100 mL), collected, dried over MgSO$_4$, filtered, and concentrated under reduced pressure to afford 8 (2.17 g, 6.65 mmol, 95% yield) as a colorless solid. No further purification was necessary: mp 84-86° C.; $^1$H NMR (600 MHz, CDCl$_3$) δ 6.65 (s, 1H), 6.16 (s, 2H), 3.87 (s, 3H), 3.84 (s, 3H), 3.26 (hept, J=6.9 Hz, 1H), 2.47 (dd, J=14.4, 6.8 Hz, 1H), 2.33 (ddd, J=14.6, 11.8, 7.4 Hz, 1H), 1.51-1.28 (m, 2H), 1.21 (s, 3H), 1.19 (s, 3H), 1.16 (d, J=12.6 Hz, 5H), 1.06 (s, 3H), 0.15 (d, J=4.0 Hz, 1H); $^{13}$C NMR (175 MHz, CDCl$_3$) δ C: 152.2, 150.3, 139.5, 133.2, 127.1, 35.0, 31.2, 25.9; CH: 130.6, 123.0, 120.4, 28.8; CH$_2$: 35.6, 31.3, 18.7, 17.0; CH$_3$: 61.1, 60.1, 26.7, 26.3, 23.7, 23.2; IR (thin-film): 2959, 1391 cm$^{-1}$; HRMS-DART (m/z) [M+H]$^+$ calculated for C$_{22}$H$_{31}$O$_2$=327.2324; found 327.2331.

Cyclopropyl Ketone 11.

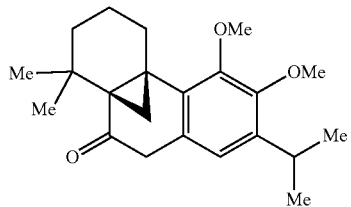

11: C$_{22}$H$_{30}$O$_3$
MW: 342.48

A solution of freshly prepared DMDO (99 mL, 6.9 mmol, 0.07 M in acetone) maintained at –0° C. was added rapidly to a solution of 10 (2.20 g, 6.74 mmol) in CH$_2$Cl$_2$ (5.0 mL) at –0° C. After 5 min, BF$_3$·OEt$_2$ (0.35 mL, 10 mmol) was added via syringe. The reaction mixture was maintained at –0° C. for 1 h, then treated with saturated aq. NaHCO$_3$ (10 mL). The resulting slurry was warmed to r.t., transferred to a separatory funnel, and extracted with EtOAc (3×50 mL). The combined organic extracts were washed with brine (50 mL), dried over MgSO$_4$, filtered, and concentrated under reduced pressure to afford 11 (2.19 g, 6.40 mmol, 95% yield) as an orange foam. No further purification was required: $^1$H NMR (600 MHz, CDCl$_3$) δ 6.57 (s, 1H), 3.89 (s, 3H), 3.87-3.80 (m, 4H), 3.26 (hept, J=6.9 Hz, 1H), 3.13 (d, J=14.9 Hz, 1H), 2.32-2.14 (m, 2H), 1.54-1.45 (m, 1H), 1.45-1.35 (m, 1H), 1.26 (s, 3H), 1.24-1.14 (m, 12H), 0.77 (d, J=4.8 Hz, 1H); $^{13}$C NMR (175 MHz, CDCl$_3$) b C: 209.8, 151.8, 149.9, 141.5, 134.4, 127.2, 41.3, 31.1, 26.0, 25.9; CH: 120.6, 29.2, CH$_2$: 47.2, 35.9, 30.4, 26.4, 18.9; CH$_3$: 60.7, 59.6, 26.7, 25.0, 23.7, 23.3; IR (thin-film): 2959, 1707, 1412 cm$^{-1}$; HRMS-DART (m/z) [M+Na]$^+$ calculated for C$_{22}$H$_{30}$O$_3$Na=365.2093; found 342.2092.

Pre-Taxodione 13.

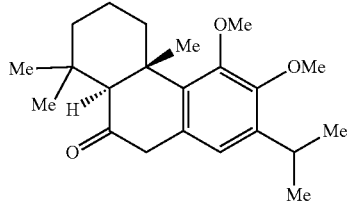

13: C$_{22}$H$_{32}$O$_3$
MW: 344.50

Freshly distilled TMSCl (0.3 mL, 3 mmol) was added dropwise to a solution of 11 (500 mg, 1.46 mmol) and NaI (438 mg, 2.92 mmol) in MeCN (6.9 mL) at r.t. After 1 h, the reaction mixture was concentrated under reduced pressure to provide 12 (652 mg, 1.39 mmol, >95% yield) as a brown foam. This material was used directly.

Iodide 12 was digested in EtOAc (28 mL) and treated with acetic acid (5.0 mL, 87 mmol). Zinc powder (1.20 g, 2.00 mmol) was added in a single portion. The resulting slurry was rapidly stirred and warmed to 75° C. After 5 min, the reaction was cooled to r.t. and treated with saturated aq. NaHCO$_3$ (50 mL). The resulting slurry was transferred to a separatory funnel and extracted with EtOAc (3×25 mL). The combined organic extracts were washed with brine (75 mL), dried over MgSO$_4$, filtered, and concentrated under reduced pressure. The resulting crude residue was purified by flash chromatography (SiO$_2$, 40:1 hexanes/EtOAc) to afford 13 (413 mg, 1.20 mmol, 82% yield) as a yellow foam: $^1$H NMR (600 MHz, CDCl$_3$) δ 6.61 (s, 1H), 3.84 (s, 3H), 3.78 (s, 3H), 3.68 (d, J=20.3 Hz, 1H), 3.38 (d, J=20.3 Hz, 1H), 3.26 (hept, J=6.8 Hz, 1H), 3.16-3.04 (m, 1H), 2.61 (s, 1H), 1.81-1.66 (m, 1H), 1.65-1.57 (m, 1H), 1.35 (s, 4H), 1.26 (s, 4H), 1.23-1.16 (m, 6H), 1.12 (dd, J=13.6, 3.6 Hz, 1H), 1.02 (s, 3H); $^{13}$C NMR (175 MHz, CDCl$_3$) δ C: 210.2, 151.8, 149.9, 141.2, 139.1, 128.8, 44.8, 32.8; CH: 121.1, 33.0; CH$_2$: 46.4, 42.4, 38.0, 19.2; CH$_3$: 63.1, 60.2, 26.6, 23.6, 23.3, 22.6, 21.9; IR (thin-film): 2965, 1717 cm$^{-1}$; HRMS-DART (m/z) [M+H]$^+$ calculated for C$_{22}$H$_{33}$O$_3$=345.2430; found 345.2424.

Iodide 12:

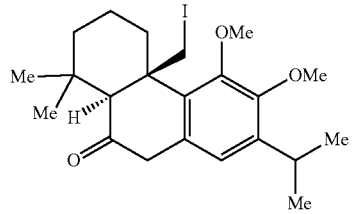

12: C$_{22}$H$_{31}$IO$_3$
MW: 470.13

An analytical sample of 12 was purified by flash chromatography (SiO$_2$, 9:1 hexanes/EtOAc). This material was light sensitive and proved difficult to store without decomposition: $^1$H NMR (600 MHz, CDCl$_3$) δ 6.65 (s, 1H), 3.88 (s, 3H), 3.82 (d, J=10.6 Hz, 1H), 3.78 (s, 3H), 3.66 (d, J=10.5 Hz, 1H), 3.58 (d, J=1.9 Hz, 2H), 3.36-3.21 (m, 2H), 2.64 (s, 1H), 1.77 (td, J=13.2, 4.5 Hz, 1H), 1.72-1.59 (m, 2H), 1.45 (d, J=13.8 Hz, 1H), 1.39 (s, 3H), 1.25-1.14 (m, 7H), 1.11 (s, 3H); $^{13}$C NMR (175 MHz, CDCl$_3$) δ C: 208.7, 152.1, 149.8, 142.2, 135.4, 129.3, 60.1, 48.2, 32.9; CH: 121.1, 33.5; CH$_2$: 46.2, 42.5, 37.4, 19.0, 14.3; CH$_3$: 62.5, 60.3, 26.7, 23.7, 23.1, 21.5; IR (thin-film): 2965, 2360, 1717 cm$^{-1}$; HRMS-DART (m/z) [M+H]$^+$ calculated for C$_{22}$H$_{32}$IO$_3$=470.1318; found 470.1323.

(±)-taxodione (8).

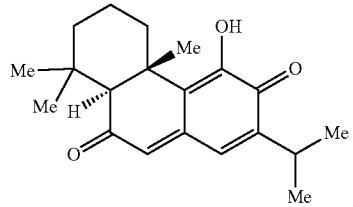

8: C$_{20}$H$_{26}$O$_3$
MW: 314.19

A solution of 13 (30.0 mg, 0.087 mmol) in CH$_2$Cl$_2$ was cooled to −78° C. A solution of BBr$_3$ (0.35 mL, 0.35 mmol) in CH$_2$Cl$_2$ (1.0 M) was added drop-wise via syringe. After 10 min, the reaction was allowed to slowly warm to r.t. over 30 min. The solution was then cooled to 0° C., treated with saturated aq. NaHCO$_3$ (2 mL), and allowed to slowly warm to r.t. over 30 min. The resulting slurry was transferred to a separatory funnel and extracted with EtOAc (3×15 mL). The combined organic extracts were washed with saturated aqueous Na$_2$S$_2$O$_3$ (5 mL) and brine (5 mL), dried over MgSO$_4$, filtered, and concentrated under reduced pressure to provide a mixture of 8 and S7. This material was digested in CHCl$_3$ (2.0 mL) and treated with SiO$_2$ (500 mg). The resulting slurry was maintained at r.t. and stirred rapidly under a balloon of O$_2$. After 12 h, the reaction was filtered to remove SiO$_2$, and the filter cake was washed with CHCl$_3$ (2×5 mL). The combined CHCl$_3$ were concentrated under reduced pressure to afford 8 (25.4 mg, 0.081, 93% yield) as a yellow solid: $^1$H NMR (400 MHz, CDCl$_3$) δ 7.57 (s, 1H), 6.93-6.83 (m, 1H), 6.21 (s, 1H), 3.11-3.01 (m, 1H), 2.99-2.86 (m, 1H), 2.59 (s, 1H), 1.79-1.67 (m, 2H), 1.63-1.55 (m, 1H), 1.44-1.36 (m, 1H), 1.27 (s, 6H), 1.21 (dd, J=13.1, 3.7 Hz, 1H), 1.18 (d, J=6.9 Hz, 3H), 1.16 (d, J=6.9 Hz, 3H), 1.11 (s, 3H). This characterization data was identical to previously reported values.[14]

Catechol S7.

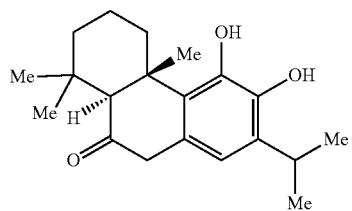

S7: C$_{20}$H$_{28}$O$_3$
MW: 316.20

The ratio of S7 and 8 was variable. Purification of this mixture by flash chromatography (SiO$_2$, 1:1 hexanes/CHCl$_3$) afforded 8, typically in modest yield because the material deposits on SiO$_2$. However, this technique provided an analytical sample of S7 contaminated with ~5% of 8. We note that contamination was unavoidable because S7 oxidized to 8 in the NMR tube: $^1$H NMR (400 MHz, CDCl$_3$) δ 6.40 (s, 1H), 5.84 (s, 1H), 4.73 (s, 1H), 3.69 (d, J=20.1 Hz, 1H), 3.37 (d, J=20.0 Hz, 1H), 3.25-3.12 (m, 1H), 3.00 (hept, J=6.8 Hz, 1H), 2.65 (s, 1H), 1.85-1.68 (m, 1H), 1.68-1.59 (m, 2H), 1.35 (s, 3H), 1.25 (t, J=6.7 Hz, 9H), 1.21-1.08 (m, 2H), 1.02 (s, 3H); $^{13}$C NMR (151 MHz, CDCl$_3$) δ C: 211.1, 149.9, 143.2, 139.2, 132.9, 132.2, 63.7, 30.1, CH: 126.6, 33.1, CH$_2$: 44.6, 42.4, 33.0, 19.2, CH$_3$: 27.7, 23.6, 23.1, 22.3, 21.7.

Enone 14.

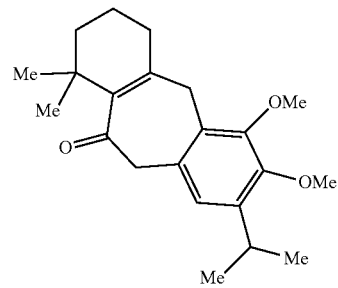

14: C$_{22}$H$_{30}$O$_3$
MW: 342.22

NaI (390 mg, 2.62 mmol) was added in a single portion to a solution of 11 (450 mg, 1.31 mmol) in MeCN (13 mL). Freshly distilled TMSCl (0.3 mL, 3 mmol) was added via syringe and the reaction was maintained at r.t. After 1 h, AgTFA (860 mg, 3.90 mmol) was added in a single portion. A precipitate formed. The resulting slurry was stirred for 5 min, then filtered over a pad of Celite. The filter cake was washed with EtOAc (2×5 mL). The combined organic filtrate was treated with saturated aq. Na$_2$S$_2$O$_4$ (5 mL). The resulting slurry was transferred to a separatory funnel and extracted with EtOAc (3×15 mL). The combined organic extracts were washed with saturated aq. NaHCO$_3$ (2×20 mL) and brine (20 mL), dried over MgSO4, filtered, and concentrated under reduced pressure. The resulting residue was purified flash chromatography (SiO$_2$ 20:1 pentane/Et$_2$O) to afford 14 (282 mg, 0.825 mmol, 63% yield) alongside a 6:1 mixture of 17a and 17b (134 mg 0.393 mmol, 30% yield). Structure 14 was a yellow oil: $^1$H NMR (400 MHz, CDCl$_3$) δ 6.80 (s, 1H), 3.86-3.81 (m, 6H), 3.77 (s, 2H), 3.55 (s, 2H), 3.27 (hept, J=6.9 Hz, 1H), 2.42 (t, J=6.4 Hz, 2H), 1.68-1.58 (m, 2H), 1.42-1.31 (m, 2H), 1.22-1.17 (m, 6H), 1.16 (s, 6H); $^{13}$C NMR (100 MHz, CDCl$_3$) δ C: 197.3, 152.4, 149.3, 148.8, 141.4, 140.9, 130.6, 129.9, 77.3, 77.0, 76.7, 34.4; CH: 121.3, 26.8; CH$_2$: 52.9, 40.7, 35.8, 34.0, 18.6; CH$_3$: 60.9, 60.7, 28.3, 23.5; IR (thin-film): 2930, 1685 cm$^{-1}$; HRMS-DART (m/z) [M+H]$^+$ calculated for C$_{22}$H$_{31}$O$_3$=343.2273; found 343.2295.

The mixture of 17a/17b could not be fully resolved. Analytical samples of 17a and 17b were prepared by pTLC (SiO$_2$, 10:1 pentane/Et$_2$O). Both structures could be assigned; however, each sample was contaminated with traces of the other isomer.

Isomer 17a:

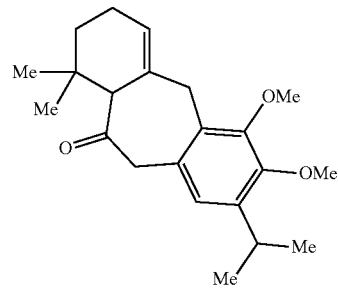

17a: C$_{22}$H$_{30}$O$_3$
MW: 342.22

¹H NMR (600 MHz, CDCl₃) δ 6.72 (s, 1H), 5.72 (td, J=3.8, 2.0 Hz, 1H), 3.83 (s, 3H), 3.81 (s, 3H), 3.78 (d, J=14.6 Hz, 1H), 3.73 (d, J=16.0 Hz, 1H), 3.57 (d, J=14.6 Hz, 1H), 3.44 (d, J=15.7 Hz, 1H), 3.26 (d, J=7.0 Hz, 1H), 3.02 (s, 1H), 2.10-2.02 (m, 2H), 1.68 (dt, J=13.6, 7.0 Hz, 1H), 1.28-1.22 (m, 2H), 1.21 (d, J=6.8 Hz, 3H), 1.19 (d, J=6.8 Hz, 3H), 1.10 (s, 3H), 0.93 (s, 3H); ¹³C NMR (175 MHz, CDCl₃) δ C: 207.9, 150.3, 149.6, 140.5, 132.4, 130.3, 130.0, 33.2, 32.0; CH: 125.5, 122.7, 62.2, 28.1; CH₂: 51.0, 35.2, 23.1, 26.8; CH₃: 60.7, 60.5, 23.6, 23.5; IR (thin-film): 2930, 1736 cm⁻¹; HRMS-DART (m/z) [M+H] calculated for $C_{22}H_{31}O_3$=343.2273, found 343.2280.

Isomer 17b:

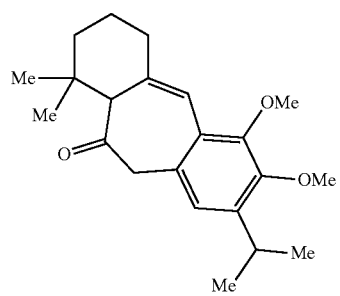

17b: $C_{22}H_{30}O_3$
MW: 342.22

¹H NMR (600 MHz, CDCl₃) δ 6.82-6.73 (m, 2H), 3.85 (s, 3H), 3.82 (s, 3H), 3.59-3.49 (m, 2H), 3.27 (p, J=6.9 Hz, 1H), 2.97 (t, J=1.8 Hz, 1H), 2.49 (dd, J=14.4, 5.1 Hz, 1H), 2.35 (tt, J=10.9, 4.8 Hz, 1H), 1.73-1.60 (m, 2H), 1.48-1.38 (m, 1H), 1.22 (d, J=1.8 Hz, 3H), 1.21 (d, J=1.8 Hz, 3H), 1.09 (s, 3H), 0.95 (s, 3H); ¹³C NMR (175 MHz, CDCl₃) δ C: 203.2, 150.5, 149.1, 142.3, 137.4, 129.0, 127.3; CH: 121.2, 120.9, 64.2, 27.0; CH₂: 50.0, 40.5, 37.1, 23.6; CH₃: 60.9, 60.7, 29.8, 29.8, 23.6, 23.2; IR (thin-film): 2945, 1738 cm⁻¹; HRMS-DART (m/z) [M+H] calculated for $C_{22}H_{31}O_3$=343.2273, found 343.2279.

Hydroxyl Ketone 18.

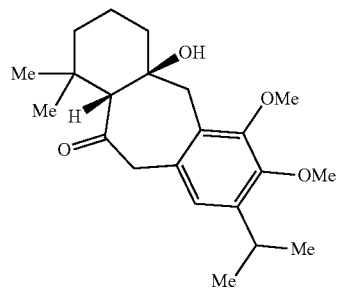

18: $C_{22}H_{32}O_4$
MW: 360.23

THF was sparged under a positive pressure of O₂ for 15 min before use. A mixture of 17a/17b (450 mg, 1.31 mmol) was dissolved in oxygenated THF (22 mL). Co(acac)₂ (77 mg, 0.30 mmol) was added in a single portion. The resulting slurry was treated with phenylsilane (0.24 mL, 2.0 mmol) and stirred at r.t. under a balloon of O₂. After 1 h, the reaction mixture was treated with saturated aq. Na₂S₂O₃ (10 mL). The slurry was transferred to a separatory funnel and extracted with EtOAc (3×20 mL). The combined organic extracts were washed with water (30 mL) and brine (30 mL), dried over MgSO₄, filtered, and concentrated under reduced pressure. The resulting crude residue was purified by flash chromatography (SiO₂, 20:1 hexanes/Et₂O to afford 18 (391 mg, 1.09 mmol, 83% yield) as a colorless solid: mp=132-134° C.; ¹H NMR (400 MHz, CDCl₃) δ 6.77 (s, 1H), 3.89-3.84 (m, 6H), 3.72 (d, J=20.3 Hz, 1H), 3.42 (d, J=19.5 Hz, 1H), 3.33 (hept, J=6.9 Hz, 1H), 3.10 (d, J=14.6 Hz, 1H), 2.64 (s, 1H), 2.31 (d, J=14.6 Hz, 1H), 2.11-2.02 (m, 1H), 1.85-1.75 (m, 1H), 1.72-1.66 (m, 1H), 1.64-1.57 (m, 2H), 1.57-1.50 (m, 2H), 1.27 (d, J=7.0 Hz, 3H), 1.21 (d, J=6.9 Hz, 3H), 1.02 (s, 3H), 0.88 (s, 3H); ¹³C NMR (101 MHz, CDCl₃) δ C: 210.9, 151.4, 149.4, 141.5, 131.1, 126.3, 77.4, 77.1, 76.8, 75.2, 32.4, 27.3; CH: 122.3, 60.5, 26.8; CH₂: 52.3, 40.2, 35.3, 34.7, 17.9; CH₃: 61.2, 60.6, 30.2, 29.5, 23.8, 23.3; IR (thin-film): 2920, 1740 cm⁻¹; HRMS-ESI (m/z) [M+Na]⁺ calculated for $C_{22}H_{32}O_4Na$=383.2198, found 383.2199. Crystals suitable for X-ray diffraction were prepared by slow evaporation from CH₂Cl₂/hexanes (CCDC 2129321).

Allylic Alcohol S8.

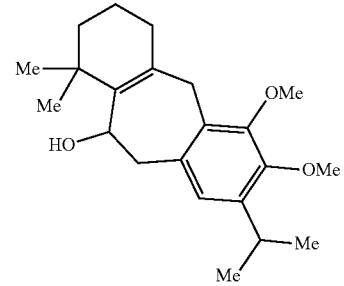

S8: $C_{22}H_{32}O_3$
MW: 344.24

A solution of 14 (220 mg, 0.634 mmol) was added drop-wise via syringe to a suspension of powdered LiAlH₄ (113 mg, 3.00 mmol) in THF (6.0 mL). The suspension was stirred at r.t. After 5 h, the reaction mixture was treated with saturated aq. KNaC₄H₄O₆ (2 mL). The resulting slurry was transferred to a separatory funnel and extracted with EtOAc (3×10 mL). The combined organic extracts were washed with brine (20 mL), dried over MgSO₄, filtered, and concentrated under reduced pressure. The resulting crude residue was purified by flash chromatography (SiO₂, 20:1 hexanes/EtOAc) to afford S8 (181 mg, 0.526 mmol, 83% yield) as a colorless oil: ¹H NMR (600 MHz, CDCl₃) δ 6.81 (s, 1H), 4.49 (t, J=7.7 Hz, 1H), 3.83 (s, 3H), 3.79 (s, 3H), 3.51 (d, J=16.8 Hz, 1H), 3.32-3.21 (m, 3H), 3.01 (dd, J=14.2, 6.4 Hz, 1H), 2.27-2.10 (m, 2H), 1.64 (p, J=6.6 Hz, 2H), 1.45-1.37 (m, 2H), 1.20 (d, J=2.3 Hz, 3H), 1.19 (d, J=2.3 Hz, 3H), 1.13 (s, 3H), 1.07 (s, 3H); ¹³C NMR (175 MHz, CDCl₃) δ C: 149.7, 148.9, 140.1, 139.9, 132.6, 132.5, 131.4, 34.8; CH: 123.3, 66.1, 26.6; CH₂: 40.9, 39.7, 34.7, 31.9, 19.3; CH₃: 60.9, 60.8, 29.8, 28.5, 23.7, 23.6; IR (thin-film): 3350, 3190 cm⁻¹; HRMS-ESI (m/z) [M−H₂O]⁺ calculated for $C_{22}H_{30}O_2$=327.2340, found 327.2341.

Icetexane 16.

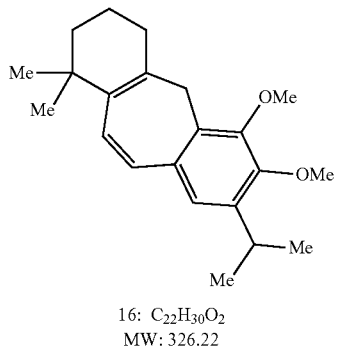 [SMILES: COc1c(C(C)C)cc2c(c1OC)CC1=C(C=C2)C(C)(C)CCC1]

16: C$_{22}$H$_{30}$O$_2$
MW: 326.22

Burgess reagent (21 mg, 0.084 mmol) was added in a single portion to a solution of S8 (20 mg, 0.058 mmol) in toluene (1.0 mL). The reaction was heated to 80° C. After 5 min, the reaction was cooled to r.t. and treated with water (1 mL). The resulting slurry was transferred to a separatory funnel and extracted with EtOAc (3×5 mL). The combined organic extracts were washed with brine (10 mL), dried over MgSO$_4$, filtered, and concentrated under reduced pressure. The resulting crude residue was purified by flash chromatography (SiO$_2$, 20:1 pentane/acetone) to afford 16 (14 mg, 0.041 mmol, 71% yield) as a colorless oil: $^1$H NMR (600 MHz, CDCl$_3$) δ 6.91-6.85 (m, 2H), 6.53 (d, J=11.9 Hz, 1H), 3.88 (s, 3H), 3.86 (s, 3H), 3.29 (hept, J=6.9 Hz, 1H), 2.97 (s, 2H), 2.36 (t, J=6.3 Hz, 2H), 1.64-1.57 (m, 2H), 1.46-1.40 (m, 2H), 1.23 (s, 3H), 1.22 (s, 3H), 1.05 (s, 6H). This characterization data was identical to previously reported data.$^{15}$ V. Synthesis of Non-Natural Abeo-Abietanes [in Scheme 5]
Iso-Icetexane 19.

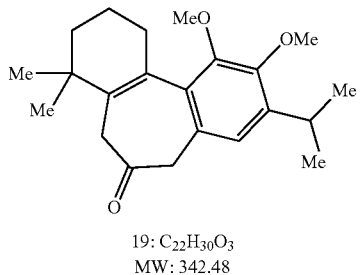 [SMILES: COc1c(C(C)C)cc2c(c1OC)C1=C(CC(=O)C2)C(C)(C)CCC1]

19: C$_{22}$H$_{30}$O$_3$
MW: 342.48

A solution of 11 (30 mg, 0.088 mmol) in CH$_2$Cl$_2$ (4.5 mL) was treated with BF$_3$·OEt$_2$ (0.7 mL, 3 mmol) at r.t. After 5 min, the reaction mixture was heated to 50° C. After 4 h, the reaction was cooled to r.t. and treated with saturated aq. NaHCO$_3$ (1 mL). The resulting slurry was transferred to a separatory funnel and extracted with EtOAc (3×5 mL). The combined organic extracts washed with saturated aq. NaHCO$_3$ (2×10 mL) and brine (10 mL), dried with MgSO$_4$, filtered, and concentrated under reduced pressure. The resulting crude residue was purified by flash chromatography (SiO$_2$, 20:1 hexanes/Et$_2$O) to afford 19 (0.4 g, 0.085 mmol, 96% yield) as a tan solid. MP=122-124° C.; $^1$H NMR (600 MHz, CDCl$_3$) δ 6.73 (s, 1H), 3.86 (s, 3H), 3.79 (s, 3H), 3.68-3.57 (m, 1H), 3.36-3.24 (m, 2H), 3.05-2.84 (m, 3H), 2.07-1.95 (m, 1H), 1.86-1.73 (m, 1H), 1.73-1.54 (m, 3H), 1.24-1.16 (m, 6H), 1.09 (s, 3H), 1.06 (s, 3H); $^{13}$C NMR (175 MHz, CDCl$_3$) δ C: 213.8, 150.9, 149.6, 141.5, 137.5, 132.2, 132.1, 129.6, 35.7; CH: 121.6, 26.8; CH$_2$: 49.3, 43.9, 39.6, 30.2, 20.2; CH$_3$: 61.0, 60.2, 28.3, 28.2, 23.7, 23.2; IR (thin-film): 2980, 1735 cm$^{-1}$; HRMS-DART (m/z) [M+H]$^+$ calculated for C$_{22}$H$_{31}$O$_3$=343.2273, found 343.2280 found. Structure 19 was confirmed by single crystal X-ray diffraction (CCDC 2129323).

Bicyclo[4.4.1]undecanone 20.

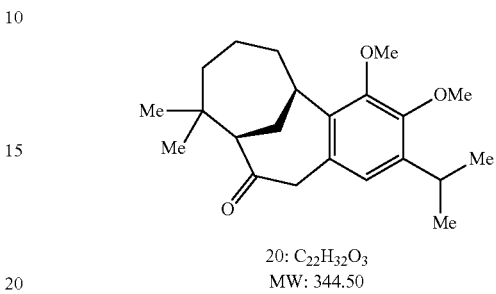

20: C$_{22}$H$_{32}$O$_3$
MW: 344.50

MeCN was degassed by 3 successive cycles of freeze-pump-thaw prior to use. A quartz vial was charged with a solution of 11 (30 mg, 0.088 mmol) and Et$_3$N (0.06 mL, 0.4 mmol) in degassed MeCN (1.8 mL). The reaction vessel was transferred to a Rayonet chamber photoreactor preheated to 35° C. and exposed to 254 nm light. After 2 h, the reaction was removed from the reactor, cooled to r.t., and concentrated under reduced pressure. The resulting crude reside was purified by flash chromatography (SiO$_2$, 20:1 hexanes/Et$_2$O) to afford 20 (24 mg, 0.069 mmol, 78% yield) as a colorless foam. $^1$H NMR (400 MHz, CDCl$_3$) δ 6.67 (s, 1H), 4.12 (d, J=12.8 Hz, 1H), 3.82 (s, 3H), 3.81 (s, 3H), 3.67-3.57 (m, 1H), 3.51 (d, J=12.8 Hz, 1H), 3.24 (hept, J=6.6 Hz, 1H), 2.58-2.44 (m, 2H), 2.28 (dd, J=15.8, 7.4 Hz, 1H), 2.17-1.97 (m, 2H), 1.64-1.47 (m, 2H), 1.46-1.36 (m, 2H), 1.24 (s, 3H), 1.19 (t, J=7.1 Hz, 6H), 1.06 (s, 3H); $^{13}$C NMR (175 MHz, CDCl$_3$) δ C: 209.5, 150.0, 149.0, 140.0, 136.7, 127.8, 34.9; CH: 123.7, 61.2, 34.7, 26.8; CH$_2$: 50.3, 40.1, 34.1, 25.1, 22.0; CH$_3$: 60.7, 60.4, 30.7, 29.3, 23.7, 23.4; IR (thin-film): 2980, 1720 cm$^{-1}$; HRMS-ESI (m/z) [M+Na]$^+$ calculated for C$_{22}$H$_{32}$O$_3$Na=367.2249, found 367.2242. Structure 20 was confirmed by single crystal X-ray diffraction (CCDC 2129319).

Bicyclo[4.4.1]undecanes 21 and 22

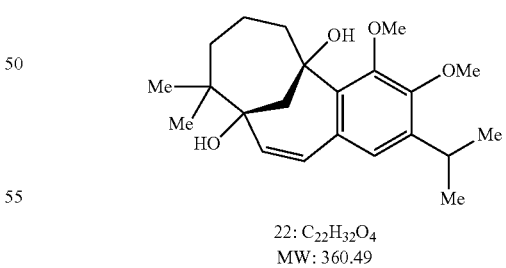

22: C$_{22}$H$_{32}$O$_4$
MW: 360.49

A solution of 10 (30 mg, 0.092 mmol) in THF/H$_2$O (9:1, 1.0 mL) was cooled to 0° C. NIS (41 mg, 0.18 mmol) was added in a single portion. The resulting red solution was warmed to r.t. After 15 min, AgTFA (40 mg, 0.18 mmol) was added as a single portion. A yellow precipitate immediately formed. The resulting slurry was stirred at r.t. for 5 min, then diluted with EtOAc (10 mL) and filtered over a pad of Celite®. The filtrate was washed with EtOAc (2×10 mL) and the combined organic extracts were washed with saturated aq. $NaHCO_3$ (2×10 mL), saturated aq. $Na_2S_2O_3$ (2×10 mL) and brine (10 mL). The organic layer was collected, dried over $MgSO_4$, filtered, and concentrated under reduced pressure. The resulting crude residue was purified by flash chromatography ($SiO_2$, 15:1 hexanes/EtOAc) to afford a 1:1 mixture of isomers 21 and 22 (27 mg, 0.075 mmol, 82% yield) as a colorless solid. Alternatively, 22 could be prepared as a single isomer in identical yield by replacing THF with MeCN in the procedure above: mp=136-138° C.; $^1$H NMR (600 MHz, $CDCl_3$) δ 6.83 (s, 1H), 6.30 (d, J=12.6 Hz, 1H), 6.25 (s, 1H), 5.95 (dd, J=12.6 Hz, 2.6 Hz, 1H), 3.89 (s, 3H), 3.82 (s, 3H), 3.26 (hept, J=7.0 Hz, 1H), 2.67 (dd, J=2.4, 15.1 Hz, 1H), 2.42 (d, J=15.2 Hz, 1H), 1.95-1.78 (m, 3H), 1.50-1.38 (m, 3H), 1.20 (dd, J=8.8, 6.9 Hz, 6H), 1.12 (d, J=2.7 Hz, 6H); $^{13}$C NMR (175 MHz, $CDCl_3$) δ C: 150.1, 149.3, 140.4, 138.9, 128.7, 128.3, 127.5, 76.6, 76.1, 41.3; CH: 133.0, 130.8, 26.6; $CH_2$: 49.7, 44.1, 41.9, 18.5; $CH_3$: 61.7, 60.8, 26.4, 23.5, 23.1, 21.1; IR (thin-film): 2920, 1890 cm$^{-1}$; HRMS-DART (m/z) [M+H]$^+$ calculated for $C_{22}H_{33}O_4$=361.2379; found 361.2359. The connectivity and relative stereochemistry of 22 was confirmed by single crystal X-ray diffraction (CCDC 2129324).

An analytic sample of 21 was prepared by pTLC (20:1 hexanes/EtOAc).

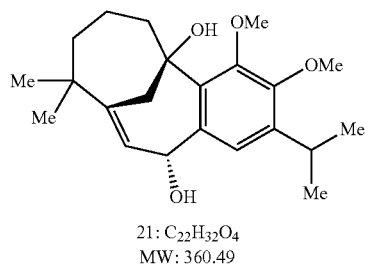

21: $C_{22}H_{32}O_4$
MW: 360.49

This structure exhibited the following characterization data: mp=134-137° C.; $^1$H NMR (600 MHz, $CDCl_3$) δ 7.44 (s, 1H), 5.76 (s, 1H), 5.63 (s, 1H), 4.80 (s, 1H), 3.97 (s, 3H), 3.76 (s, 3H), 3.38-3.22 (m, J=7.5, 7.0 Hz, 1H), 2.89 (d, J=13.9 Hz, 1H), 2.65 (dd, J=14.0, 2.2 Hz, 1H), 2.34-2.19 (m, 2H), 1.90-1.75 (m, 2H), 1.67 (dd, J=13.6, 6.0 Hz, 1H), 1.52-1.38 (m, 1H), 1.28-1.19 (m, 6H), 1.13 (s, 3H), 1.10 (s, 3H); $^{13}$C NMR (175 MHz, $CDCl_3$) δ C: 151.8, 149.4, 143.8, 140.9, 136.1, 134.8, 74.1, 37.6; CH: 129.9, 117.10, 69.8, 28.4; $CH_2$: 46.1, 45.7, 36.9, 19.8; $CH_3$: 60.8, 60.3, 26.9, 26.2, 23.5, 23.5; IR (thin-film): 2920, 1890, 1780 cm$^{-1}$; HRMS-DART (m/z) [M+H]$^+$ calculated for $C_{22}H_{33}O_4$=361.2359; found 361.2367. The connectivity and relative stereochemistry of 21 was confirmed by single crystal X-ray diffraction (CCDC 2129322).

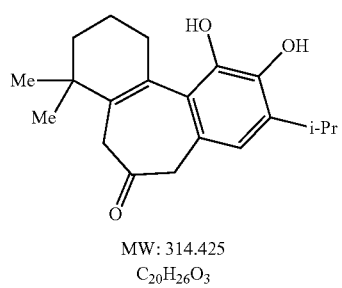 [SMILES: CC(C)c1cc2c(c(O)c1O)C1=C(CC(=O)C2)C(C)(C)CCC1]

MW: 314.425
$C_{20}H_{26}O_3$ $^1$H NMR (400 MHz, $CDCl_3$) δ 6.55 (s, 1H), 5.19 (s, 2H), 3.58 (d, J=15.6 Hz, 1H), 3.29 (d, J=15.5 Hz, 1H), 3.14 (hept, J=6.9 Hz, 1H), 3.01-2.88 (m, 3H), 2.07 (d, J=16.0 Hz, 1H), 1.86-1.75 (m, 1H), 1.74-1.55 (m, 3H), 1.25-1.21 (m, 6H), 1.10 (s, 3H), 1.06 (s, 3H); $^{13}$C NMR (101 MHz, $CDCl_3$) δ C: 214.6, 140.8, 140.4, 139.4, 133.5, 130.3, 125.9, 125.1, 35.8, CH: 118.1, 39.6, $CH_2$: 28.4, 28.3, 27.3, 22.6, 22.4, $CH_3$: 49.3, 44.1, 29.7, 20.0; HRMS-ESI (m/z) [M+H]$^+$ calculated for $C_{20}H_{27}O_6$=315.1960, found=325.1962.

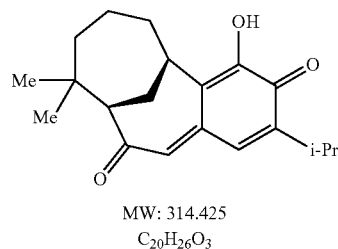 [SMILES: CC(C)C1=CC2=CC(=O)[C@@H]3C[C@@H](CCCC3(C)C)C2=C(O)C1=O]

MW: 314.425
$C_{20}H_{26}O_3$ $^1$H NMR (400 MHz, $CDCl_3$) δ 6.98 (s, 1H), 6.79 (s, 1H), 6.28 (s, 1H), 3.53 (dt, J=12.2, 7.9 Hz, 1H), 3.06 (hept, J=6.9 Hz, 1H), 2.48 (dd, J=16.0, 8.5 Hz, 1H), 2.37 (d, J=7.3 Hz, 1H), 2.17 (dd, J=16.1, 7.4 Hz, 1H), 2.02 (dt, J=15.1, 7.7 Hz, 1H), 1.80 (t, J=13.1 Hz, 1H), 1.72-1.46 (m, 3H), 1.43 (s, 3H), 1.15 (d, J=6.9 Hz, 6H), 1.05 (s, 3H); $^{13}$C NMR (151 MHz, $CDCl_3$) δ C: 201.1, 181.7, 145.3, 145.0, 134.0, CH: 139.9, 136.2, 63.0, 33.3, 21.2, $CH_2$: 22.1, 21.8, 21.7, 18.6 $CH_3$: 42.6, 37.0, 32.8, 27.1; HRMS-ESI (m/z) [M+H]$^+$ calculated for $C_{20}H_{27}O_6$=315.1960, found=325.1959.

Results and Discussion

Inspired by the photobiology of vitamin A, we envisioned a different polyene cyclization strategy. In place of isolated polyene 1, we targeted conjugated β-ionyl derivative 3. Following Buchi's investigations on the photoisomerization of β-ionone to Z-retro-γ-ionone,[15] we reasoned that diene 4 could be unveiled from 3 via a photoinduced [1,5]-hydride shift. The bifurcated π-systems in 4 could then be connected via a Heck cyclization, where the position of the C-X bond would guide site-specific incorporation of the aryl ring. We predicted that a 6-exo-trig pathway to generate alkyl metal species A would be favored,[16] thereby providing an avenue to modify the oxidation-state of C20, most directly by cyclization to propellane 5. Fragmentation of this overbred species was viewed as handle for skeletal editing. Moreover, this sequence would allow 5 to be assembled from interchangeable fragments. We expected these features to not only expedite entry to diterpene natural products, but also simplify the design of tailored compositions of matter that are beyond the reach of semi-synthesis. Herein, we report the successful implementation of this programmed polycyclization strategy and highlight its utility for the synthesis of canonical and rearranged abietane diterpenes.[17]

We began by examining the photoisomerization of β-ionyl derivatives 3. While the photosensitized geometric isomerization of β-ionyl species is established,[18] positional alkene isomerization via a [1,5]-hydride shift is an underexplored pathway observed upon direct irradiation.[19] Thus, it was not clear if this reaction would be broadly synthetically useful. To address this concern, a set of electronically differentiated photosubstrates 3 were prepared from benzylic alcohols 6 via conversion to aryl phosphonates 7 and olefination with β-cyclocitral.[20] As shown in Table 1, we were pleased to find that irradiation of 3a (R$^1$, R$^2$=OMe) with 350 nm light in deoxygenated THF provided Z-diene 4a in 90% yield (entry 1).[21] The reaction time was reduced to 1 h using 300 nm light (entry 2). In contrast, 254 nm light resulted in decomposition (entry 3). Dioxane and MeCN gave similar results to THF (entries 4 and 5); however, the reaction rate slowed as the concentration of 3a increased. Guided by these observations, we developed a general procedure using 300 nm light in dioxane (0.2 M) that provided 4a in 87% yield after 5 h (entry 6). This transformation was remarkably efficient, with no evidence of other products by $^1$H NMR. Moreover, these mild conditions were extended to differentiated cyclization substrates 3b ($R^1$, $R^2$=H) and 3c ($R^1$=$CF_3$, $R^2$=H) to generate 4b (90% yield) and 4c (86% yield) as single isomers, respectively (entries 7 and 8).

TABLE 1

Photoisomerizaiton of β-ionyl derivatives 3.[a,b]

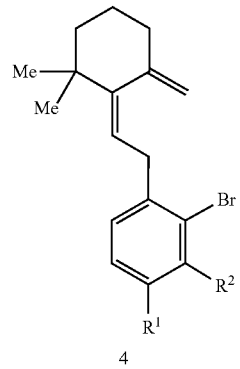

| entry | solvent [0.04 M] | hv (nm)[c] | 3 | $R^1$ | $R^2$ | % of 4 (time, h) |
|---|---|---|---|---|---|---|
| 1 | THF | 350 | 3a | OMe | OMe | 90 (9 h) |
| 2 | THF | 300 | 3a | OMe | OMe | 92 (1 h) |
| 3 | THF | 254 | 3a | OMe | OMe | 10 (1 h) |
| 4 | dioxane | 300 | 3a | OMe | OMe | 93 (2 h) |
| 5 | MeCN | 300 | 3a | OMe | OMe | 85 (1 h) |
| 6 | dioxane[d] | 300 | 3a | OMe | OMe | 87[e] (5 h) |
| 7 | dioxane[d] | 300 | 3b | H | H | 90[e] (5 h) |
| 8 | dioxane[d] | 300 | 3c | $CF_3$ | H | 86[e] (5 h) |

[a]Yields were determined by $^1$H NMR using $Me_2SO_2$ as an internal standard.
[b]Solvent was degassed by successive freeze-pump-thaw cycles.
[c]Reactions were carried out in a Rayonet photoreactor maintained at 35° C.
[d][4] = 0.2M.
[e]Isolated yield after purification by silica gel chromatography.

Figure 2:
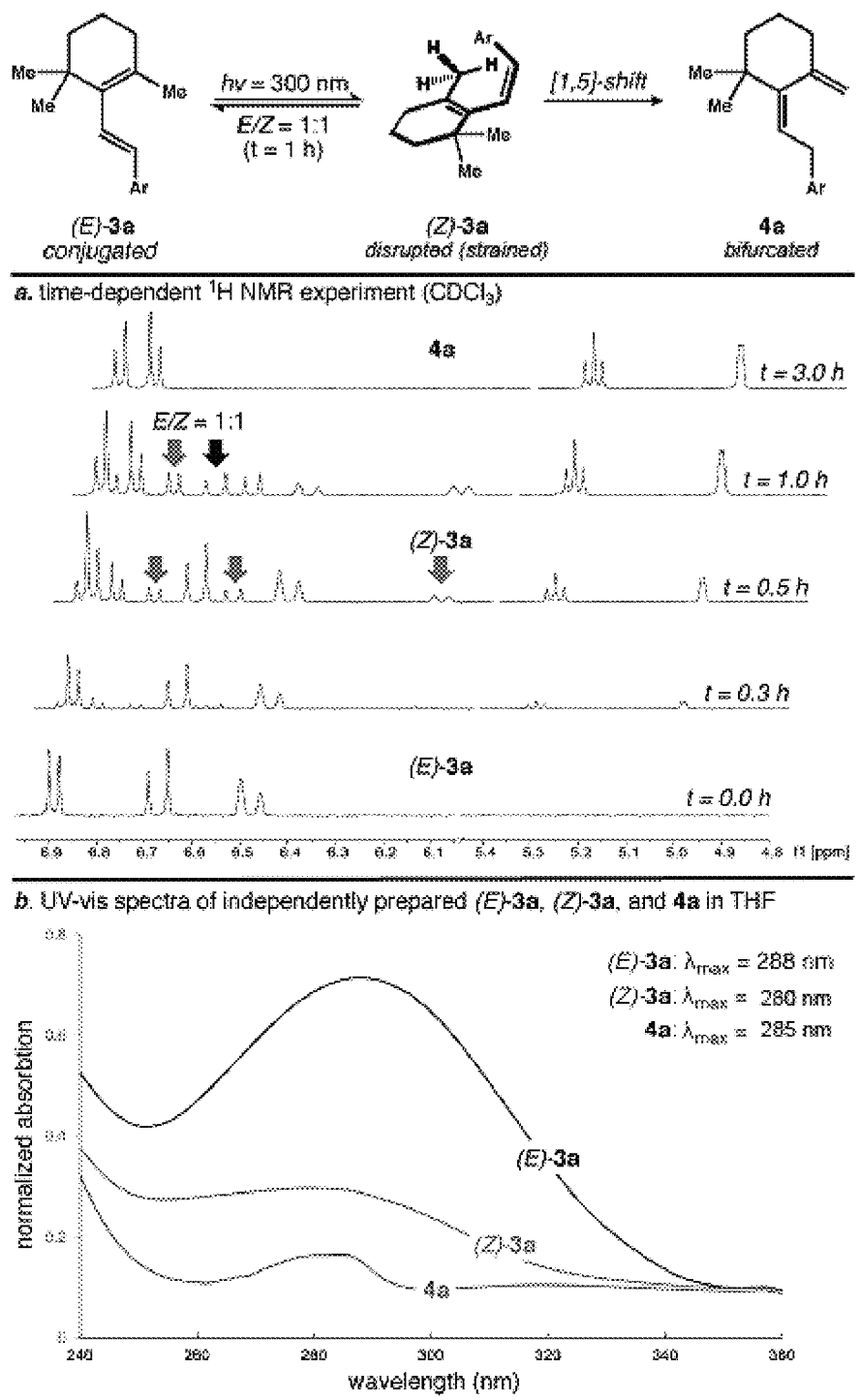
FIG. 2 shows chromophore disruption in the photoisomerization of a β-ionyl compound.

The isomerization of 3a was explored in detail (FIG. 2). Analysis of a test reaction (hv=300 nm, 0.1 M in THF) by $^1$H NMR revealed initial isomerization of the exocyclic alkene to generate a mixture of (E)-3a and (Z)-3a. These species were present in a 1:1 ratio after 1 h, alongside 4a. After 2 h, (E)-3a was consumed and a mixture of (Z)-3a and 4a persisted until the reaction was complete. We prepared (Z)-3a independently and found that the photochemistry of this isomer was indistinguishable from (E)-3a.[22] Thus, the initial geometry of the exocyclic alkene was inconsequential. In contrast, 4a did not react with 300 nm light, yet reverted to (E)-3a in >95% yield when heated to 150° C. via a thermal (retro) [1,5]-hydride shift.

These results indicate that 4a is metastable intermediate that likely accumulates because disruption of the extended π-system prevents re-excitation. This conclusion was supported by analyzing the absorption spectra of (E)-3a, (Z)-3a, and 4a in THF. These data revealed significant hypochromic shifts for (Z)-3a and 4a relative to (E)-3a, which is consistent with impaired conjugation. Notably, the π-system in (Z)-3a is distorted by allylic strain, which also restricts interconversion to the s-trans conformer.[23] This same steric effect may also facilitate a photochemical [1,5]-hydride shift within (Z)-3a to give 4a, a process that requires an otherwise difficult-to-achieve antarafacial transition state.[24]

Figure 3:
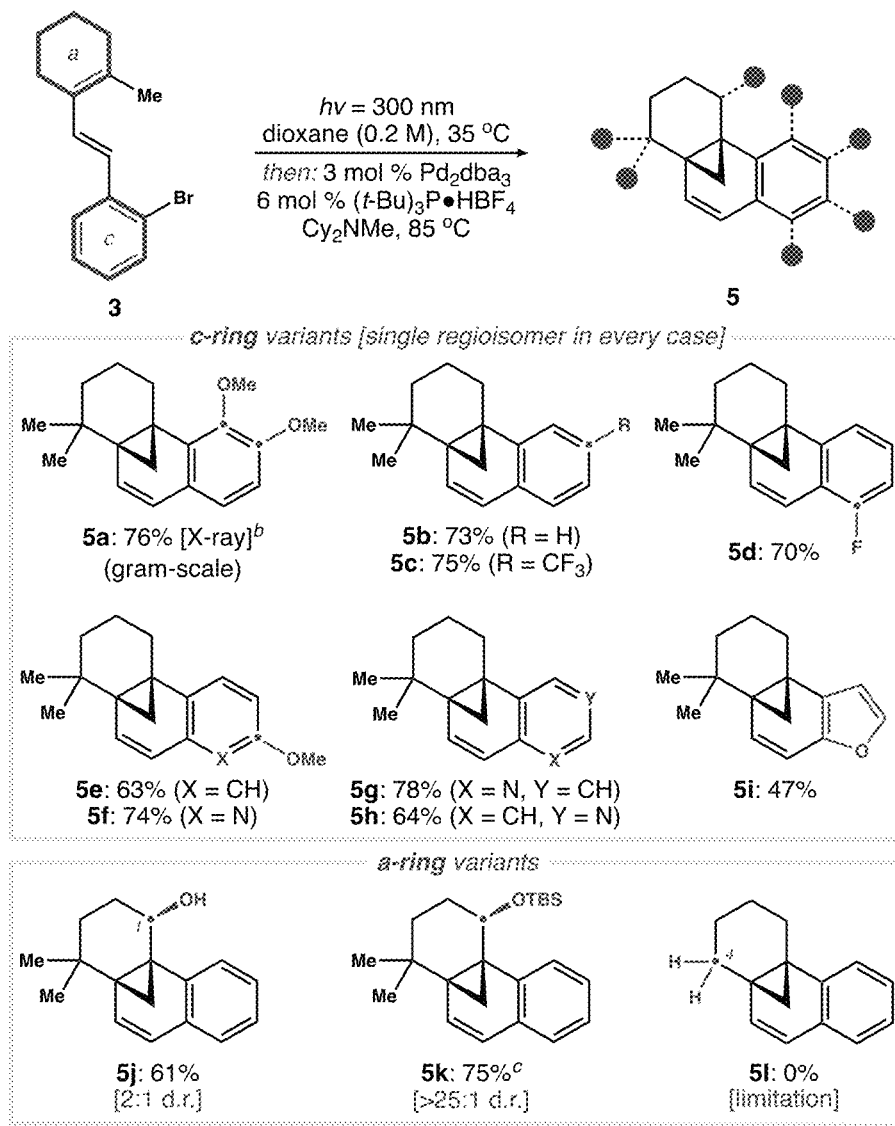
FIG. 3 shows the cyclization of β-ionyl compounds.

Our next goal was to execute the proposed Heck reaction within 4a. After some experimentation, we identified the combination of $Pd_2dba_3$/P(t-Bu)$_3$ (1:1 Pd/P) and $Cy_2NMe$ described by Fu to be the most effective.[25] Exposure of 4a to this catalyst system in dioxane at 85° C. gave 5a in 93% yield. As shown in FIG. 3, the photoisomerization and Heck cyclization were merged into a single operation. This more convenient process afforded 5a in 76% yield from 3a on gram-scale.[26] Moreover, this process was effective across a range of cyclization precursors (3b-3k). Accordingly, C-ring variants 3b-3e with peripheral substituents at every position around the aryl nucleus were tolerated. By design, a single regioisomer of 5 was obtained in every case. In addition, the reaction was effective for electron-rich (5a and 5e), non-activated (5b), and electron-deficient (5c and 5d) substrates. This feature allowed us to prepare variants of 5 harboring π-deficient (5f-5h) and π-excessive (5i) heterocyclic rings.

peranol (9), an isomer of 8 distinguished by a [6-7-6] icetexane skeleton.[31] In Nature, this rearranged abeo-abietane framework is prepared from an abietane via an oxidation-enabled Wagner-Meerwein rearrangement.[32] Nevertheless, 9 is not readily accessible using polyene cyclization. As a result, existing total syntheses of 8 and 9 treat each carbocyclic framework as an independent problem.[33]

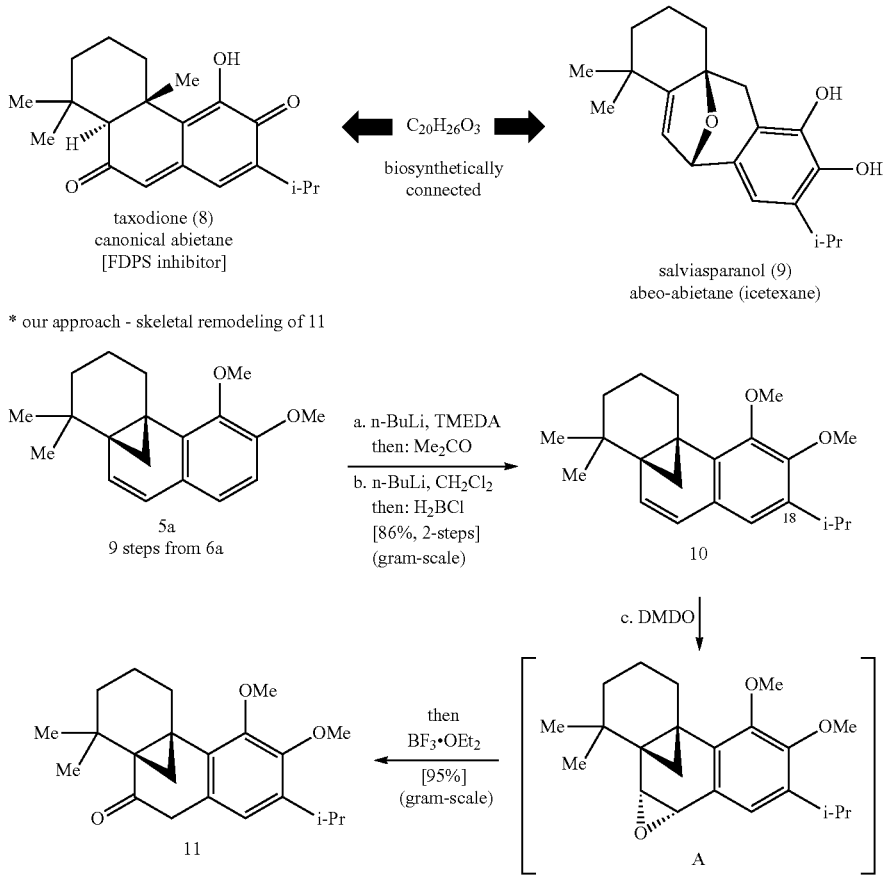

Scheme 3

Modifications of the A-ring were also investigated. For example, the addition of an alcohol at C1 provided 5j in 2:1 d.r. (61% yield).[27] This selectivity was readily improved to >25:1 d.r. in 5k (75% yield) when a bulky silyl protecting group was included. In contrast, propellane 51 lacking a gem-dimethyl group at C4 was a limitation. In this case, photolysis of 31 did not produce isomer 41. Instead, E→Z isomerization of the exocyclic alkene was the exclusive reaction. This outcome demonstrates the importance of allylic strain introduced by the gem-dimethyl group in the [1,5]-hydride shift process.

Having established the proposed photoinduced polycyclization cascade, we turned our attention to examining its utility in target-oriented synthesis. As shown in Scheme 2, we selected abietane diterpenes for this purpose. Our interest in this diterpene family was inspired by taxodione (8), a novel inhibitor of farnesyl diphosphate synthase.[28] Among the reported syntheses of 8,[29] an 11-step route featuring biomimetic polycyclization is the most concise.[30] This work provided a valuable benchmark. We also targeted salvias- To evaluate the utility of our strategy, we set out to develop a unified entry point to 8 and 9 via late-stage diversification of overbred abietane 11. This common intermediate was prepared on gram-scale from 5a via ortho-lithiation and trapping with acetone. Deoxygenation of the resultant alcohol using Kabalka's protocol provided 10 in 86% overall yield.[34] The olefin in 10 was then reacted with DMDO to give epoxide A, a transient species that smoothly rearranged to ketone 11 in 95% yield upon exposure to BF$_3$·OEt$_2$.

A total synthesis of (±)-taxodione (8) was achieved from 11 via ring-opening of the activated cyclopropyl ketone (Scheme 4). In this case, 11 was reacted with excess TMSCl and NaI in MeCN.[35] Following an aqueous workup, this protocol provided iodide 12 in >95% yield. It was best not to purify this sensitive intermediate. Instead, alkyl iodide 12 was directly reduced with zinc powder to furnish 13 in 82% yield. Deprotection of the aryl ethers with BBr$_3$ then unveiled the corresponding catechol, which rapidly to oxidized 8 in 93% yield upon exposure to SiO$_2$ and oxygen.[36]

As such, this approach provided (±)-8 in 9 total steps and 41% overall yield from commercially available fragments 6a and β-cyclocitral.

Figure 4:
FIG. 4 shows the diverted total synthesis of (±)-taxodione and formal synthesis of (±)-salviasperanol from a ketone produced by the methods described herein.
Figure 4:
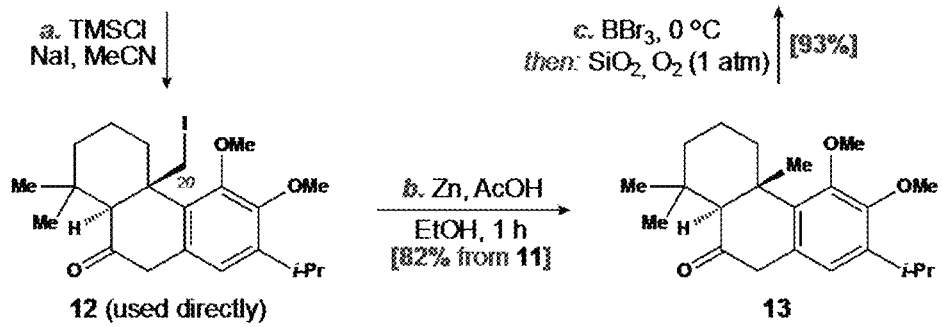
Figure 4:
Figure 4:
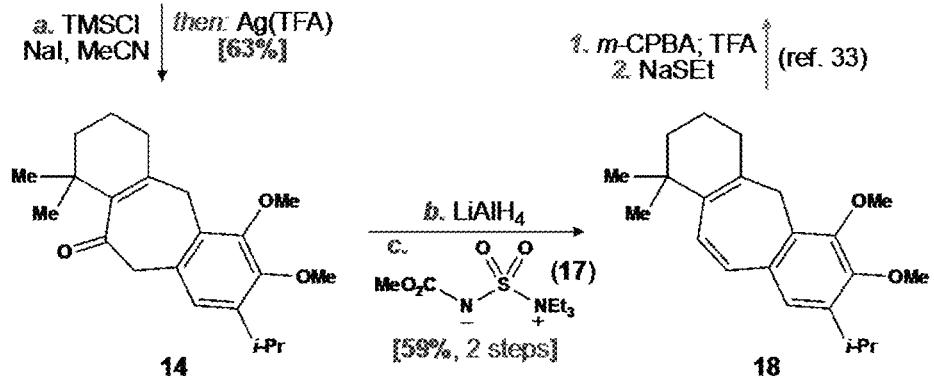
Figure 4:
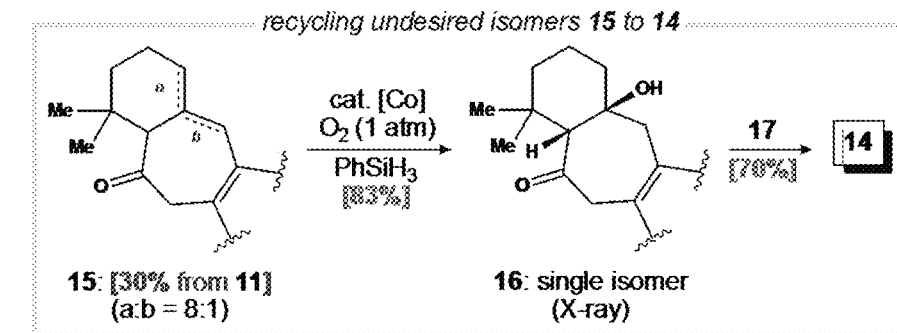

Intermediate 11 was also diverted to (±)-salviasperanol (9). In this context, alkyl iodide 12 was generated in situ as before and then treated with Ag(TFA) to induce a biomimetic skeletal rearrangement.[32] Under dilute conditions (0.05 M), this reaction provided enone 14 in 63% yield alongside an 8:1 mixture of isomers 15a and 15b. Mixtures of 15 were recycled to 14 in two steps. In this case, Mukaiyama hydration of 15 gave alcohol 16 as a single diastereomer in 83% yield. Subsequent dehydration of 16 using Burgess reagent (17) afforded 14 in 70% yield. Alternatively, a formal synthesis of (±)-9 was completed by reducing 14 with LiAlH$_4$. Dehydration of the resultant allylic alcohol with 17 furnished diene 18 in 59% yield over two steps. Notably, Sarpong and co-workers previously elaborated 18 to 9.[33a] Therefore, 9 was formally prepared in 9 total steps (21% overall yield) and, for the first time, along the same synthetic pathway as abietane 8 (FIG. 4).

Figure 5:
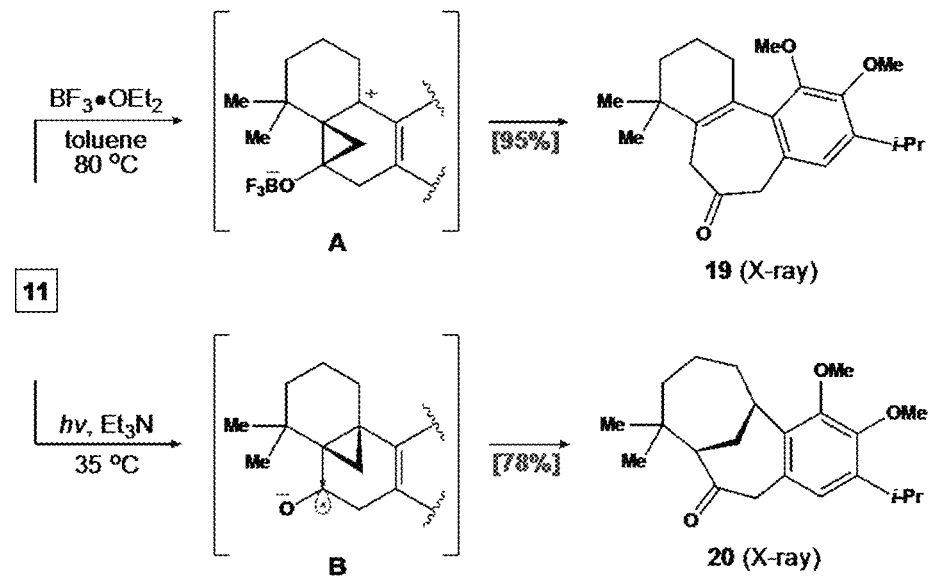
FIG. 5 shows the synthesis of diversified non-natural abeo-abietanes via skeletal remodeling of propellanes produced by the methods described herein.
Figure 5:
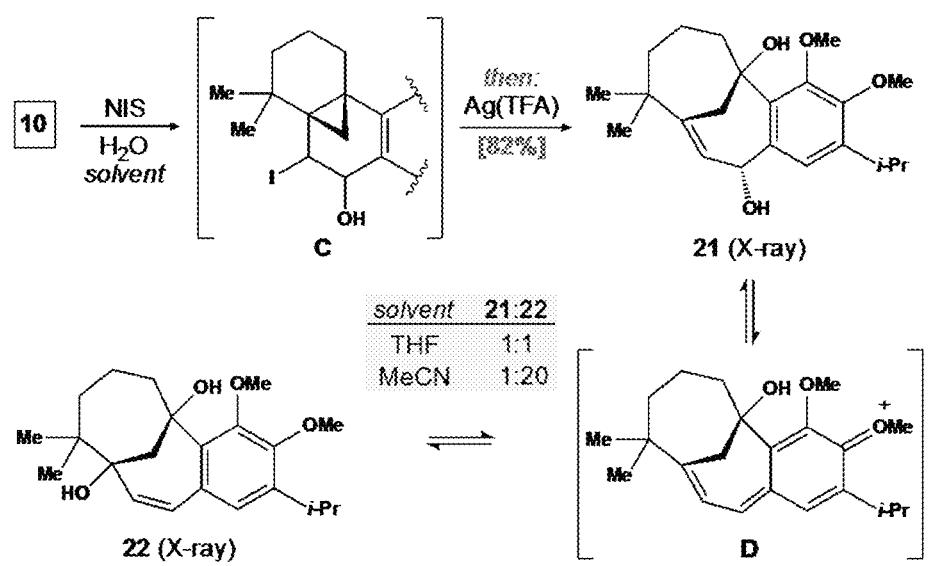

Skeletal remodeling of 11 also supported entry to unprecedented abeo-abietane scaffolds (FIG. 5). For example, exposure of 11 to BF$_3$·OEt$_2$ in toluene at 80° C. afforded isomeric [6-7-6] ring system 19 in 95% yield. We suspect that that 19 is derived of cation A, which itself arises from a (net) [1,3]-alkyl shift within the initial Lewis adduct of 11.37 Alternatively, irradiation of 11 (hv=254 nm) in the presence of Et$_3$N generated [4.4.1] bicyclic motif 20, putatively via ketyl radical B.[38] This carbocycle is reminiscent of the cyclocitrinols,[39] and was available at a higher oxidation state from 10. In this case, 10 was reacted with NIS in aqueous THF to give halohydrin C. Upon exposure to Ag(TFA), this reactive species furnished alcohols 21 and 22 in 82% yield (1:1 ratio). We found that 21 isomerized to 22 in the presence of TsOH, putatively via cation D. Alternatively, 22 was isolated in 82% yield when MeCN was used in place of THF. Collectively, these non-canonical abietanes illustrate the structural diversity that can be achieved by controlled fragmentation of the propellane within 5a.

In summary, we established an atypical polyene cyclization strategy that converts easily accessible β-ionyl derivatives into polycyclic [4.4.1]-propellanes. Unlike canonical biomimetic polyene cyclization, this strategy allows for complete control of regiochemistry and tolerates a range of electron-rich and electron-deficient (hetero)aryl groups. The strained polycycles produced from this chemistry were elaborated to diterpene architectures via late-stage skeletal remodeling. This powerful feature was highlighted in a unified synthesis of taxodione (8) and salviasperanol (9) that is concise, modular, and amenable to asymmetric induction in future iterations. Alternative diversification pathways were explored, and these generated a collection of non-canonical abeo-abietane scaffolds that would be difficult or impossible to prepare using conventional biomimetic logic. As a result, this terpene assembly strategy appears to be well-suited for applications in both target- and diversity-oriented synthesis.

Figure 6:
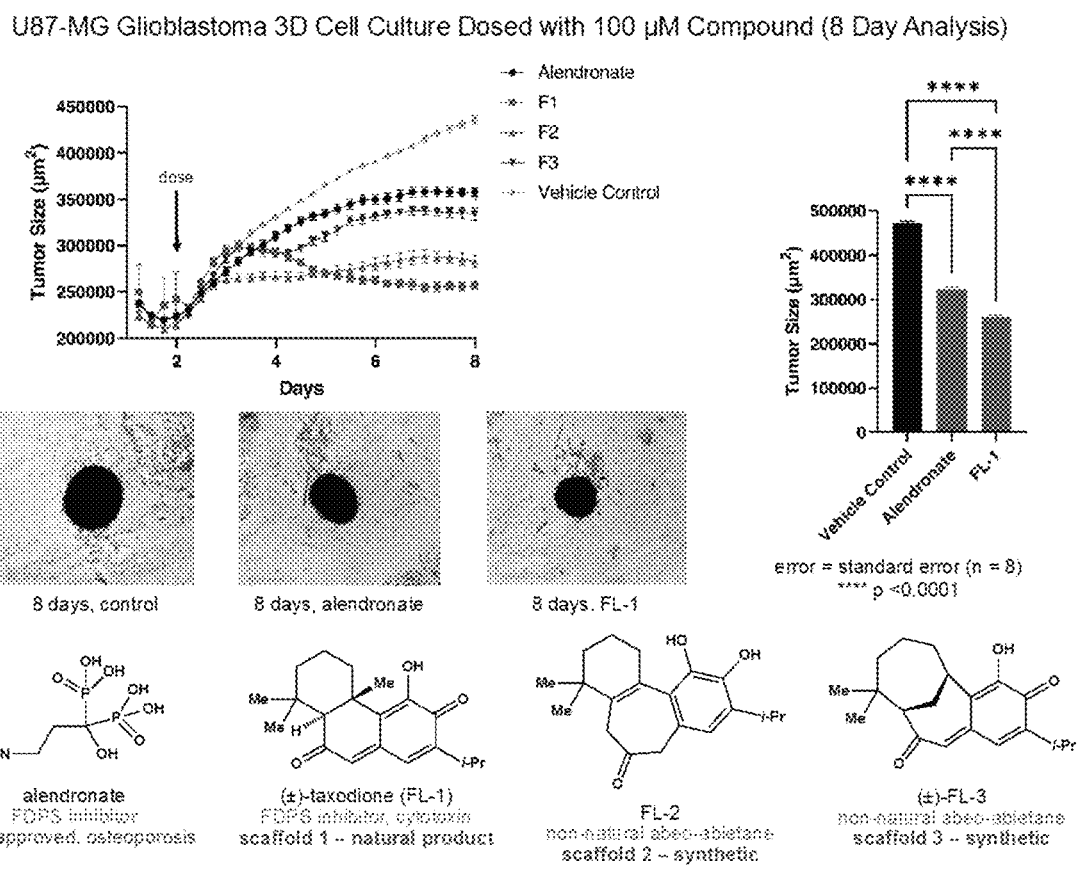
FIG. 6 shows compounds described herein are effective in inhibiting glioblastoma cell growth.

With entry to fully synthetic abietanes in hand, we explored the activity of taxodione (FL-1) and several synthetic analogs (FL-2 and FL-3) in glioblastoma cell culture (FIG. 6). As shown in FIG. 6, all three compounds are superior to alendronate in arresting 3D 'tumor' cell growth. Nevertheless, it is clear that a synthetic entry to bioactive molecules that inhibit glioblastoma cell growth has been established. This is a particularly important application because glioblastoma is an invasive brain cancer with a 5-year mean survival rate of only 5.5%. There are few effective treatments beyond surgery and ionizing radiation. Thus, new therapy modalities are urgently needed.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES (1) Cox-Georgian, D.; Ramadoss, N.; Dona, C.; Basu, C. Therapeutic and medicinal uses of terpenes. *Medicinal Plants* 2019, 333-359.

(2) Newman, D. J.; Cragg, G. M. Natural products as sources of new drugs over the nearly four decades from January 2081 to September 2019. *J. Nat. Prod.* 2020, 83, 770-803.

(3) Gonzales, M. A. Aromatic abietane diterpenoids: Their biological activity and synthesis. *Nat. Prod. Rep.* 2015, 32, 684-704.

(4) Reveglia, P; Cimmino, A.; Masi, M.; Nocera, P.; Berova, N.; Ellestad, G.; Evidente, A. Pimarane diterpenes: Natural source, stereochemical configuration, and biological activity. *Chirality* 2018, 30, 1115-1134.

(5) Zhao, X.; Cacherat, B.; Hu, Q.; Ma, D. Recent advances in the synthesis of ent-Kaurane diterpenoids. *Nat. Prod. Rep.* 2022, 39, 119-138.

(6) (a) Tantillo, D. J. Biosynthesis via carbocations: Theoretical studies on terpene formation. *Nat. Prod. Rep.* 2011, 28, 1035-1053; (b) Hong, Y. J.; Tantillo, D. J. Formation of Beyerene, Kaurene, Trachylobane, and Atiserene diterpenes by rearrangements that avoid secondary carbocations. *J. Am. Chem. Soc.* 2010, 132, 5375-5386.

(7) Dibrell, S. E.; Tao, Y.; Reisman, S. E. Synthesis of complex diterpenes: Strategies guided by oxidation pattern analysis. *Acc. Chem. Res.* 2021, 54, 1360-1373.

(8) Zhang, X.; King-Smith, E.; Dong, L.-B.; Yang, L.-C.; Rudolf, J. D.; Shen, B.; Renata, H. Divergent synthesis of complex diterpenes via a hybrid oxidative approach. *Science* 2020, 369, 799-806.

(9) For reviews, see: Yoder, R. A.; Johnston, J. N. A case study on biomimetic total synthesis: Polyolefin carbocyclizations to terpenes and steroids. *Chem. Rev.* 2005, 105, 4730-4756; (b) Ungarean, C. N.; Southgate, E. H.; Sarlah, D. Enatioselective polyene cyclizations. *Org. Biomol. Chem.* 2016, 14, 5454-5467; (c) Barrett, A. G. M., Ma, T.; Mies, T. Recent developments in polyene cyclization and their applications in natural product synthesis. *Synthesis* 2019, 51, 67-82; (d) Feilner, J. M.; Haut, F.-L.; Magauer, T. Beyond the isoprene pattern: Bifunctional polyene cyclizations. *Chem. Eur. J.* 2021, 27, 7017-7021.

(10) For select examples, see: (a) (c) Ishihara, K.; Nakamura, S.; Yamamoto, H. The first enantioselective biomimetic cyclization of polyprenoids. *J. Am. Chem. Soc.* 1999, 121, 4906-4907; (b) Zhao, Y.-J.; Chng, S.-S.; Loh, T.-P. Lewis Acid-promoted intermolecular acetal-initiated cationic polyene cyclizations. *J. Am. Chem. Soc.* 2007, 129, 492-493.

(11) For select examples, see: (a) Rendler, S.; MacMillan, D. W. C. Enantioselective polyene cyclization via organo-SOMO catalysis. *J. Am. Chem. Soc.* 2010, 132, 5027-5029; (b) Plamondon, S. J.; Warnica, J. M.; Kaldre, D.; Gleason, J. L. Hydrazide-catalyzed polyene cyclization:

Asymmetric organocatalytic synthesis of cis-decalins. *Angew. Chem., Int. Ed.* 2020, 59, 253-258; (c) b) Kutateladze, D. A.; Strassfeld, D. A., Jacobsen, E. N. Enantioselective tail-to-head cyclizaitons catalyzed by dual-hydrogen-bond donors. *J. Am. Chem. Soc.* 2020, 142, 6951-6956.

(12) For select examples, see: (a) Sethofer, S. G.; Mayer, T.; Toste, F. D. Gold(I)-catalyzed enantioselective polycyclization reactions. *J. Am. Chem. Soc.* 2010, 132, 8276-8277; (b) Schaforth, M. A.; Sarlah, D.; Krautwald, S.; Carreira, E. M. Iridium-catalyzed enantioselective polyene cyclization. *J. Am. Chem. Soc.* 2012, 134, 20276-20278; (c) Cochrane, N. A.; Nguyen, H.; Gagne, M. R. Catalytic enantioselective cyclization and C3-fluorination of polyenes. *J. Am. Chem. Soc.* 2013, 135, 628-631.

(13) For representative examples of challenges encountered with 1a, see: (a) Grayfer, T. D.; Retailleau, R.; Dood, R. H.; Dubois, J.; Cariou, K. Chemodivergent, tunable, and selective iodine(III)-mediated bromo-functionalizations of polyprenoids. *Org. Lett.* 2017, 19, 4766-4769; (b) Ishihara, K.; Ishibashi, H.; Yamamoto, H. Enantioselective biomimetic cyclization of homo(polyprenyl)arenes. A new entry to (+)-podpcarpa-8,11,13-triene diterpenoids and (−)-tetracyclic polyprenoid of sedimentary origin. *J. Am. Chem. Soc.* 2001, 123, 1505-1506.

(14) Electronically deactivated polyenes (e.g. 1b and 1c) are challenging substrates for canonical polyene cyclization: (a) Vrubliauskas, D.; Vanderwal, C. D. Cobalt-catalyzed hydrogen-atom transfer induces bicyclizations that tolerate electron-rich and electron deficient intermediate alkenes. *Angew. Chem., Int. Ed.* 2020, 59, 6115-6121. (b) Snyder, S. A.; Treitler, D. S. $Et_2SBr \cdot SbCl_5Br$: An effective reagent for direct bromonium-induced polyene cyclizations. *Angew Chem., Int. Ed.* 2009, 48, 7899-7903.

(15) Buchi, G.; Yang, N. C. Light-catalyzed organic reactions. VI. The isomerization of some dienones. *J. Am. Chem. Soc.* 1957, 79, 2318-2323.

(16) Limura, S.; Overman, L. E.; Paulini, R.; Zakarian, A. Enantioselective total synthesis of guanacastepene N using an uncommon 7-endo Heck cyclization as a pivotal step. *J. Am. Chem. Soc.* 2006, 128, 13095-13101.

(17) A creative polycyclization approach to abietane diterpenes was disclosed during the course of this study: (a) Vrubliauskas, D.; Gross, B, M.; Vanderwal, C. D. Stereocontrolled radical bicyclizations of oxygenated precursors enable short syntheses of oxidized abietane diterpenoids. *J. Am. Chem. Soc.* 2021, 143, 2944-2952; (b) Johnson, L. K.; Niman, S. W.; Vrubliauskas, D.; Vanderwal, C. D. Stereocontrolled synthesis and structural revision of plebeianol A. *Org. Lett.* 2021, 23, 9569-9573.

(18) (a) Naskar, S.; Chowdhury, S. R.; Mondal, S.; Maiti, D. K.; Mishra, S.; Das, I. Visible-light-activated divergent reactivity of dienones: Dimerization in neat conditions and regioselective E to Z isomerization in solvent. *Org. Lett.* 2019, 21, 1578-1582; (b) Livingstone, K.; Tenverge, M.; Pape, F.; Daniliuc, C. G.; Jamieson, C.; Gilmour, R. Photocatalytic E→Z isomerization of β-ionyl derivatives. *Org. let.* 2019, 21, 9677-9680.

(19) (a) de Mayo, P; Stothers, J. B; Yip, R. W. The irradiation of β-ionone. *Can. J. Chem.* 1961, 39, 2135-2137; (b) Ramamurthy, V.; Liu, R. S. H. Sigmatropic hydrogen migration and electrocyclization processes in compounds in the vitamin A series. Photochemistry of polyenes. *J. Org. Chem.* 1976, 41, 1862-1867.

(20) Ma, X.; Xu, Q.; Li, H.; Su, C.; Yu, L.; Zhang, X.; Cao, H.; Han, L.-B. Alcohol-based Michaelis-Arbuzov reaction: An efficient and environmentally-benign method for C—P(O) bond formation. *Green Chem.* 2018, 20, 3408-3413.

(21) The endoperoxide arising from photooxidation of 3 was formed in the presence of oxygen: Borsarelii, C. D.; Mischne, M.; La Venia, A.; Vieyra, F. E. M. UVA Self-photosensitized oxygenation of β-ionone. *Photochem. Photobiol.* 2007, 83, 1313-1318.

(22) (Z)-3a was prepared from (E)-3a using the following procedure: Singh, K.; Staig, S. J.; Weaver, J. D. Facile synthesis of Z-alkenes via uphill catalysis. *J. Am. Chem. Soc.* 2014, 136, 5275-5278.

(23) For a similar example, see: Molloy, J. J; Schafer, M.; Weinhold, M.; Morack, T.; Daniliuc, C. G.; Gilmour, R. Boron-Enabled geometric isomerization of alkenes via selective energy-transfer catalysis. *Science* 2020, 369, 320-306.

(24) Antarafacial [1,5]-hydride shifts are favored in rare cases: Kiefer, E. F.; Tanna, C. H. Alternative electrocyclic pathways. Photolysis and termolysis of dimethylallene dimers. *J. Am. Chem. Soc.* 1969, 91, 4478-4480.

(25) Littke, A. F.; Fu, G. C. A versatile catalyst for Heck reactions of aryl chlorides and aryl bromides under mild conditions. *J. Am. Chem. Soc.* 2001, 123, 6989-7000.

(26) We engineered an inexpensive FEP tubing spindle for the purpose of scale up. See the Supporting Information (SI) for details.

(27) The relative stereochemistry of 5j was confirmed via single crystal X-ray diffraction of a C1 alcohol derivative. See the Supporting Information (SI) for details.

(28) (1) Liu, Y.-L.; Lindert, S.; Zhu, W.; Wang, K.; McCammon, J. A.; Oldfield, E. Taxodione and Arenarone Inhibit Farnesyl Diphosphate Synthase by Binding to the Isopentenyl Diphosphate Site. *Proc. Natl, Acad. Sci., USA* 2014, 111, E2530-E2539; (b) Han, S.; Li, X.; Xia, Y.; Yu, Z.; Cha, N.; Malal, S. R.; Han, X.; Oldfield, E.; Zhang, Y. Farnesyl pyrophosphate synthase as a target for drug development: Discovery of natural-product-derived inhibitors and their activity in pancreatic cancer cells. *J. Med. Chem.* 2019, 62, 10867-10896.

(29) (a) Mori, K.; Matsui, M. Diterpenoid total synthesis XIII: Taxodione, a quinone methide tumor inhibitor. *Tetrahedron* 1970, 26, 3467-3473; (b) Matsumoto, T.; Ohsuga, Y.; Harada, S.; Fukui, K. Synthesis of taxodione, royleanone, cryptojaponol, and methyl 11-hydroxy-12-methoxy-7-oxoabieta-8,11)13-trien-18-oate. *Bull. Chem. Soc. Jpn.* 1977, 50, 266-272; (c) Matsumoto, T.; Usui, S.; Morimoto, T. A convenient synthesis of (±)-taxodione, (±)-ferruginol, and (±)-sugiol. *Bull. Soc. Chem. Jpn.* 1977, 50, 1575-1579; (d) Snitman, D. L.; Himmelsbach, R. J.; Haltwanger, R. C.; Watt, D. S. A synthesis of (±)-cryptojaponol and (±)-taxodione. *Tetrahedron Lett.* 1979, 20, 2477-2480; (e) Stevens, R. V.; Bisacchi, G. S. Benzocyclobutenones as synthons for the synthesis of C-11 oxygenated diterpenoids. Application to the total synthesis of (±)-taxodione. *J. Org. Chem.* 1982, 47, 2396-2399; (f) Johnson, W. S.; Shenvi, A. B.; Boots, S. G. An approach to taxodione involving biomimetic polyene cyclization. *Tetrahedron* 1982, 38, 1379-1404; (g) Poierier, D.; Jean, M.; Burnell, R. H. Alternate syntheses of taxodione. *Synth. Commun.* 1983, 13, 201-205; (h) Burnell, R. H.; Jean, M.; Poirier, D. Synthesis of taxodione. *Can. J. Org. Chem.* 1987, 65, 775-781; (i) Haslinger, E.; Michl, G. Synthesis of (+)-taxodione from (−)-abietic acid. *Tetrahedron Lett.* 1988, 29, 5751-5754; (j) Engler, T. A.; Smapath, U.; Naganathan, S.; Velde, D. V.; Takusagawa, F. A new general synthetic approach to diterpenes:

Application to the synthesis of (±)-taxodione and (±)-royleanone. *J. Org. Chem.* 1989, 54, 5712-5727.

(30) This total synthesis begins from commercial geranyl chloride and 2-isopropylveratrole: Harring, S. R.; Livinghouse, T. A concise biomimetic total synthesis of (±)-taxodione via a $BF_3 \cdot MeNO_2$ promoted cationic cascade annulation. *J. Chem. Soc., Chem. Commun.* 1992, 502-503.

(31) Simmons, E. M.; Sarpong, R. Structure, Biosynthetic Relationships and Chemical Synthesis of the Icetexane Diterpenoids. *Nat. Prod. Rep.* 2009, 26, 1195-1217.

(32) Thommen, C.; Neuburger, M.; Gademann, K. Collective Syntheses of Icetexane Natural Products Based on Biogenic Hypothesis. *Chem. Eur. J.* 2017, 23, 120-127.

(33) (a) Simmons, E. M.; Sarpong, R. Ga(III)—Catalyzed Cycloisomerization Strategy for the Synthesis of Icetexane Diterpenoids: Total Synthesis of (±)-Salviasperanol. *Org. Lett.* 2006, 8, 2883-2886; (b) Majetich, G.; Zou, G.; Grove, J. Total Synthesis of (±)-Salviasperanol. *Org. Lett.* 2008, 10, 85-87.

(34) Yao, M.-L.; Pippin, A. B.; Kabalka, G. W. Deoxygenation of benzylic alcohols using chloroboranes. *Tetrahedron Lett.* 2010, 51, 853-855.

(35) Dueterm R. K.; Pounds, S. Ring-opening reactions of electrophilic cyclopropanes. *J. Org. Chem.* 1982, 47, 3174-3177.

(36) The unpurified mixture of deprotected 13 was concentrated onto $SiO_2$, dissolved in $CHCl_3$, and stirred for 1 h under a balloon of $O_2$. Filtration of the resulting slurry afforded 8 in >95% purity.

(37) In principal, A could arise from the initial Lewis adduct of 11 via consecutive [1,2] alkyl shifts or a net [1,3] alkyl shift involving a non-classical carbocation: Hong, Y. J.; Giner, J.-L.; Tantillo, D. J. Bicyclobutonium ions in biosynthesis—Interconversion of cyclopropyl-containing sterols from orchids. *J. Am. Chem. Soc.* 2015, 137, 2085-2088.

(38) Cossy, J.; Furet, N. Photochemical ring opening of cyclopropyl ketones induced by electron transfer. *Tetrahedron Lett.* 1993, 34, 8107-8110.

(39) For an overview of the cyclocitrinols, see: Wu, J.; Liu, J.; Fan, J.-H.; Xie, Z.-D.; Qin, H.; Li, C.-C. Evolution of routes for asymmetric total synthesis of cyclocitrinol enabled by type II [5+2]cycloaddition. *Chin. J. Chem.* 2021, 39, 1247-1254.

The invention claimed is:

1. A compound having the structure IV or a pharmaceutically acceptable salt or ester thereof

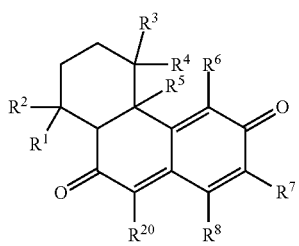

IV wherein $R^1$-$R^6$ are independently hydrogen, a halide, a substituted or unsubstituted alkyl group, an alkoxy group, or a hydroxy group, $R^7$ and $R^8$ are independently hydrogen, a halide, a substituted or unsubstituted alkyl group, or an alkoxy group, $R^{20}$ is an unsubstituted alkyl group, and the compound is not taxodione.

2. The compound of claim 1, wherein $R^1$ and $R^2$ are each an alkyl group.

3. The compound of claim 1, wherein $R^1$ and $R^2$ are each a methyl group.

4. The compound of claim 1, wherein $R^3$ and $R^4$ are each hydrogen.

5. The compound of claim 1, wherein $R^5$ is an alkyl group.

6. The compound of claim 1, wherein $R^5$ is a methyl group.

7. The compound of claim 1, wherein $R^6$ is an alkoxy group.

8. The compound of claim 1, wherein $R^6$ is a methoxy group.

9. The compound of claim 1, wherein $R^6$ is a hydroxy group.

10. The compound of claim 1, wherein $R^7$ is an alkyl group.

11. The compound of claim 1, wherein $R^7$ is an isopropyl group.

12. The compound of claim 1, wherein $R^8$ is hydrogen.

13. A pharmaceutical composition comprising a compound of claim 1.

14. A method of treating cancer in a subject, the method comprising administering to the subject a compound of claim 1.

15. The compound of claim 1, wherein $R^{20}$ is an unsubstituted C1-C24 alkyl group.

16. A compound having the structure IV or a pharmaceutically acceptable salt or ester thereof

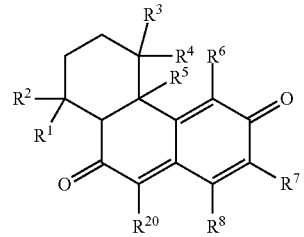

IV wherein $R^1$-$R^5$ are independently hydrogen, a halide, a substituted or unsubstituted alkyl group, an alkoxy group, or a hydroxy group, $R^6$ is a methoxy group, $R^7$, $R^8$, and $R^{20}$ are independently hydrogen, a halide, a substituted or unsubstituted alkyl group, or an alkoxy group, and the compound is not taxodione.

17. The compound of claim 16, wherein $R^1$ and $R^2$ are each an alkyl group.

18. The compound of claim 16, wherein $R^1$ and $R^2$ are each a methyl group.

19. The compound of claim 16, wherein $R^3$ and $R^4$ are each hydrogen.

20. The compound of claim 16, wherein $R^5$ is an alkyl group.

21. The compound of claim 16, wherein $R^5$ is a methyl group.

22. The compound of claim 16, wherein $R^7$ is an alkyl group.

23. The compound of claim 16, wherein $R^7$ is an isopropyl group.

24. The compound of claim 16, wherein $R^8$ is hydrogen and $R^{20}$ is hydrogen or an unsubstituted alkyl group.

25. The compound of claim 16, wherein $R^{20}$ is a C1-C24 alkyl group.

26. A pharmaceutical composition comprising a compound of claim 16.

27. A method of treating cancer in a subject, the method comprising administering to the subject a compound of claim 16.

28. A compound selected from the group consisting of

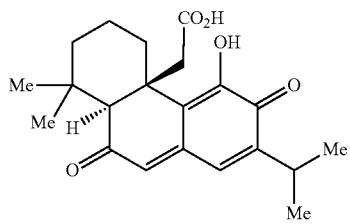

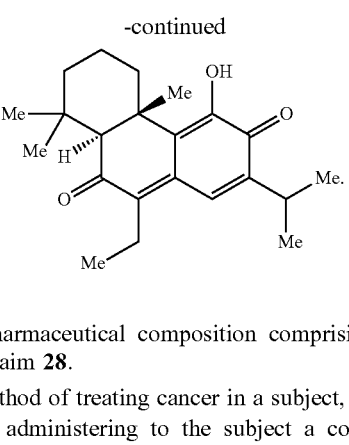

29. A pharmaceutical composition comprising a compound of claim 28.

30. A method of treating cancer in a subject, the method comprising administering to the subject a compound of claim 28.

* * * * *